(12) United States Patent
Zenhausern et al.

(10) Patent No.: US 11,860,160 B2
(45) Date of Patent: Jan. 2, 2024

(54) VERTICAL FLOW MOLECULAR ASSAY APPARATUS

(71) Applicant: Arizona Board of Regents on Behalf of the University of Arizona, Tucson, AZ (US)

(72) Inventors: Frederic Zenhausern, Chandler, AZ (US); Peng Chen, Chandler, AZ (US); Jian Gu, Chandler, AZ (US); Jerome Lacombe, Chandler, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 716 days.

(21) Appl. No.: 17/040,417

(22) PCT Filed: Mar. 29, 2019

(86) PCT No.: PCT/US2019/024879
§ 371 (c)(1),
(2) Date: Sep. 22, 2020

(87) PCT Pub. No.: WO2019/191613
PCT Pub. Date: Oct. 3, 2019

(65) Prior Publication Data
US 2021/0199651 A1 Jul. 1, 2021

Related U.S. Application Data

(60) Provisional application No. 62/650,808, filed on Mar. 30, 2018.

(51) Int. Cl.
*C12Q 1/68* (2018.01)
*G01N 33/543* (2006.01)
*B01L 3/00* (2006.01)

(52) U.S. Cl.
CPC .. *G01N 33/54391* (2021.08); *B01L 3/502715* (2013.01); *B01L 2200/0689* (2013.01);
(Continued)

(58) Field of Classification Search
None
See application file for complete search history.

(56) References Cited

U.S. PATENT DOCUMENTS

| | | |
|---|---|---|
| 4,797,260 A | 1/1989 | Parker |
| 9,086,410 B2 | 7/2015 | Chan et al. |

(Continued)

FOREIGN PATENT DOCUMENTS

| | | |
|---|---|---|
| KR | 10-2017-0076402 | 7/2017 |
| WO | WO 2020/264385 | 12/2020 |
| WO | WO 2020/264388 | 12/2020 |

OTHER PUBLICATIONS

Chinnasamy et al., Point-of-care vertical flow allergen microarray assay: Proof of concept, Clin Chem. Sep. 2014;60(9):1209-16. doi: 10.1373/clinchem.2014.223230. Epub Jul. 8, 2014.*

(Continued)

*Primary Examiner* — Aaron A Priest
(74) *Attorney, Agent, or Firm* — Leydig, Voit & Mayer, Ltd.

(57) ABSTRACT

Provided are vertical flow detection devices and related methods. The devices may comprise a membrane having a first surface and a second surface with a plurality of porous structures extending between the first and second surfaces to form fluid conduits from a first fluid chamber formed by the first surface and a second fluid chamber formed by the second fluid surface. A capture agent is immobilized on and/or in the membrane. A rigid porous membrane support mechanically supports the membrane and to provide a relatively uniform flow across the membrane. Various gas- (Continued)

kets or holder elements are positioned around an outer edge of the membrane to prevent fluid leakage around the membrane. A fluid pump is configured to force a fluid sample flow in a direction from the first fluid chamber to the second fluid chamber.

22 Claims, 50 Drawing Sheets

(52) U.S. Cl.
CPC ... *B01L 2300/0877* (2013.01); *B01L 2300/12* (2013.01); *B01L 2400/0475* (2013.01)

(56) References Cited

U.S. PATENT DOCUMENTS

| | | | |
|---|---|---|---|
| 9,784,733 B1 | 10/2017 | Wang et al. | |
| 10,898,896 B2 | 1/2021 | Zenhausern et al. | |
| 11,221,966 B2 | 1/2022 | Zenhausern et al. | |
| 2006/0088857 A1* | 4/2006 | Attiya | B01L 3/50255 435/6.12 |
| 2007/0160998 A1* | 7/2007 | Van Beuningen | B01L 3/0275 435/6.15 |
| 2007/0224701 A1 | 9/2007 | Rosenstein | |
| 2008/0038718 A1* | 2/2008 | Fischer | C12Q 1/6869 435/283.1 |
| 2008/0318342 A1 | 12/2008 | Durack et al. | |
| 2012/0087831 A1 | 4/2012 | Chan | |
| 2013/0078624 A1 | 3/2013 | Holmes et al. | |
| 2016/0010078 A1* | 1/2016 | Shirai | B01L 3/502761 506/26 |
| 2019/0345431 A1 | 11/2019 | Barrett et al. | |
| 2021/0030347 A1 | 2/2021 | Zenhausern et al. | |
| 2021/0079337 A1 | 3/2021 | Zenhausern et al. | |
| 2022/0001378 A1 | 1/2022 | Zenhausern et al. | |

OTHER PUBLICATIONS

AuCoin (2012) In vivo microbial antigen discovery: finding the "needle in the haystack" Expert Rev. Mol. Diagn. 12, 219-221. doi: 10.1586/erm.12.8.

Berger et al. (2016) "Vertical- flow paper SERS system for therapeutic drug monitoring of flucytosine in serum," Anal. Chim. Acta 949, 59-66. doi:10.1016/j.aca.2016.10.035.

Business Wire (May 9, 2016) "Technavio Announces Top Five Vendors in the Clinical Immunoassay Analyzer Market in the US from 2016 to 2020." Retrieved from: http://www.businesswire.com/news/home/20160509005857/en/Technavio-Announces-Top-Vendors-Clinical-Immunoassay-Analyzer.

Chen et al. (2017) "Development of a Vertical Flow Paper-Based Immunoassay (VFI) for Multiplexing Detection of Tier I Bio-threat Agents," Presentation and abstract, CBD S&T Conference Nov. 18-30, 2017, Long Beach, California.

Chen et al. (Jan. 2019) "Paper-based Vertical Flow Immunoassay (VFI) for Detection of Bio-threat Pathogens," Talanta, 191, 1, 81-88. doi.org: 10.1016/j.talanta.2018.08.043.

Chinnasamy et al. (2014) "Point-of-care vertical flow allergen microarray assay: Proof of concept," Clin. Chem. 60, 9, 1209-1216. doi:10.1373/clinchem.2014.223230.

Chinnasamy, Segerink, Nystrand, Gantelius, Svahn (2014) "A lateral flow paper microarray for rapid allergy point of care diagnostics," Analyst, 139, 2348-2354. doi:10.1039/c3an01806g.

Christopher et al. (1997) "Biological Warfare: a Historical Perspective," JAMA, 278(5):412-417. doi:10.1001/jama.1997. 03550050074036.

Clarke et al. (Jan. 2017) "Development of a SERS-Based Rapid Vertical Flow Assay for Point-of-Care Diagnostics," Anal. Chem. 89, 1405-1410. doi: 10.1021/acs.analchem.6b04710.

Cook et al. (2000) "The characterization of human urine for specimen validity determination in workplace drug testing: a review," J. Anal. Toxicol. 24:579-88.

Cretich et al. (2015) "Flow-through, viral co-infection assay for resource-limited settings," Talanta 132, 315-320. doi: 10.1016/j. talanta.2014.09.027.

Currie et al. (2010) "The Epidemiology and Clinical Spectrum of Melioidosis : 540 Cases from the 20 Year Darwin Prospective Study," PLoS Negl. Trop. Dis. 4(11): e900. doi:10.1371/journal.pntd.0000900.

Dahaner (Oct. 20, 2016) "Dahaner Reports Third Quarter 2016 Results," PR Newswire. Retrieved from: http://investors.danaher.com/2016-10-20-Danaher-Reports-Third-Quarter-2016-Results.

De Jager et al. (2009) "Prerequisites for cytokine measurements in clinical trials with multiplex immunoassays," BMC Immunol. 10:52.

Desmet et al. (2011) "Multiplexed immunoassay for the rapid detection of anti-tumor-associated antigens antibodies," Analyst 136, 2918-2924. doi: 10.1039/c1an15121e.

Devadhasan et al. (May 2021) "Critical Comparison between Large and Mini Vertical Flow Immunoassay Platforms for Yersinia Pestis Detection," Anal. Chem. 93, 27, 9337-9344. https://doi.org/10.1021/acs.analchem.0c05278.

Dimov et al. (2011) "Stand-alone self powered integrated microfluidic blood analysis system (SIMBAS)," Lab Chip 11:845-850.

Eltzov et al. (Jan. 2017) "Colorimetric stack pad immunoassay for bacterial identification," Biosens. Bioelectron. 87, 572-578. doi:10. 1016/j.bios.2016.08.044.

Extended European Search Report dated Mar. 2, 2022 in European Application No. 19776967, 11 pp.

Galligan et al. (2015) "Mesoscale blood cell sedimentation for processing millilitre sample volumes," Lab Chip 15:3274-3277.

Gao et al. (2015) "Fast and sensitive detection of an anthrax biomarker using SERS-based solenoid microfluidic sensor," Biosens. Bioelectron. 72, 230-236. doi:10.1016/j.bios.2015.05.005.

Gong et al. (2013) "Field tested milliliterscale blood filtration device for point-of- care applications," Biomicrofluidics 7:044111.

Grand View Research, Inc. (Feb. 15, 2016) "Paper Diagnostics Market Worth $8.35 Billion by 2022," PR Newswire. Retrieved from: http://www.prnewswire.com/news-releases/paper-diagnostics-marketworth-835-billion-by-2022-grand-view-research-inc-568821271.html.

Hárendarčíková et al. (Nov. 2017) "True lab-in-a-syringe technology for bioassays," Talanta 174, 285-288. doi: 10.1016/j.talanta. 2017.06.017.

He et al. (2012) "Visual detection of gene mutations based on isothermal strand-displacement polymerase reaction and lateral flow strip," Biosens. Bioelectron. 31, 310-315. doi:10.1016/j.bios. 2011.10.037.

Henderson et al. (2002) "Factors influencing the measurement of oestrone sulphate by dipstick particle capture immunoassay," J. Immunol. Methods 270, 77-84. doi:10.1016/S0022-1759(02)00280-6.

Higgins et al. (1999) "Sensitive and rapid identification of biological threat agents," Ann. N. Y. Acad. Sci. 894, 130-148. doi.org:10. 1111/j.1749-6632.1999.tb08056.x.

Houghton et al. (2014) "Development of a Prototype Lateral Flow Immunoassay (LFI) for the Rapid Diagnosis of Melioidosis," PLoS Neglected Trop. Dis. 8(3): e2727. doi.org/10.1371/journal.pntd. 0002727.

Hu et al. (2014) "Advances in paper-based point-of-care diagnostics," Biosens. Bioelectron. 54, 585-597. doi:10.1016/j.bios.2013. 10.075.

Indrasekara et al. (2014) "Gold Nanostar Substrates for SERS-Based Chemical Sensing in the Femtomolar Regime," Nanoscale 6, 8891-8899 DOI: 10.1039/C4NR02513J.

Indrasekara et al. (Feb. 2018) "Manipulation of the Geometry and Modulation of the Optical Response of Surfactant-Free Gold Nanostars: a Systematic Bottom-up Synthesis," ACS Omega 3, 2202-2210.

International Search Report and Written Opinion dated Jun. 19, 2019 in International Application No. PCT/US2019/024879, 8 pp.

Jansen et al. (2014) "Biological warfare, bioterrorism, and biocrime," Clin. Microbiol. Infect. 20, 488-496. doi:10.1111/1469-0691.12699.

(56) References Cited

OTHER PUBLICATIONS

Jiang et al. (2011) "A microfluidic chip for blood plasma separation using electro-osmotic flow control," J Micromech Microengineering 21:085019.

Juncker et al. (2014) "Cross-reactivity in antibody microarrays and multiplexed sandwich assays: Shedding light on the dark side of multiplexing," Curr. Opin. Chem. Biol. 18, 29-37. doi:10.1016/j.cbpa.2013.11.012.

Kim et al. (Jan. 2017) "Microfluidic Pipette Tip for High-Purity and High-Throughput Blood Plasma Separation from Whole Blood," Anal.Chem. 89:1439-1444.

Kuo et al. (2015) "Microfluidic chip for rapid and automatic extraction of plasma from whole human blood," Microsyst. Technol. 21:255-261.

Lacombe et al. (Jun. 2018) "Candidate gene bio dosimetry markers of exposure to external ionizing radiation in human blood: a systematic review," PLoS One; 13(6):e0198851.

Lafleur et al. (2012) "Progress toward multiplexed sample-to-result detection in low resource settings using microfluidic immunoassay cards" Lab Chip 12, 1119-1127. doi:10.1039/c2c20751f.

Lakoff (2008) "The Generic Threat, or how we became unprepared," Cult. Anthropol. 23, 399-428. doi: 10.1525/can.2008.23.3.399.C.

Lenshof et al. (2009) "Acoustic Whole Blood Plasmapheresis Chip for Prostate Specific Antigen Microarray Diagnostics," Anal.Chem. 2009; 81:6030-6037.

Li et al. (2010) "Rapid and Sensitive Detection of Protein Biomarker Using a Portable Fluorescence Biosensor Based on Quantum Dots and a Lateral Flow Test Strip," Anal. Chem. 82, 7008-7014.

Li et al. (2011) "Paper based point-of-care testing disc for multiplex whole cell bacteria analysis," Biosens. Bioelectron. 26, 4342-4348. doi:10.1016/j.bios.2011.04.035.

Limmathurotsakul et al. (2010) "Defining the True Sensitivity of Culture for the Diagnosis of Melioidosis Using Bayesian Latent Class Models," PLoS One 5(8): e12485. doi:10.1371/journal.pone.0012485.

Limmathurotsakul et al. (2010) "Increasing Incidence of Human Melioidosis in Northeast Thailand," Am. J. Trop. Med. Hyg. 82(6): 1113-1117. doi:10.4269/ajtmh.2010.10-0038.

Limmathurotsakul et al. (2016) "Predicted global distribution of Burkholderia pseudomallei and burden of melioidosis," Nat. Microbiol. 1, 15008. doi: 10.1038/nmicrobiol.2015.8.

Liu et al. (2009) "Aptamer-Nanoparticle Strip Biosensor for Sensitive Detection of Cancer Cells," Anal. Chem. 81(24): 10013-10018.

Liu et al. (2015) "A Plasmonic Gold Nanostar Theranostic Probe for In Vivo Tumor Imaging and Photothermal Therapy Theranostics," 5(9): 946- 960 DOI: 10.7150/thno.11974.

Liu et al. (2016) "A high-efficiency superhydrophobic plasma separator," Lab Chip, 16:553-560.

Lu et al. (2010) "Fabrication and characterization of paper-based microfluidics prepared in nitrocellulose membrane by Wax printing," Anal. Chem. 82, 329-335. doi:10.1021/ac9020193.

Lu et al. (2014) "Identification of gene expression biomarkers for predicting radiation exposure," Sci Rep. 4:6293. doi: 10.1038/srep06293.

Lucas et al. (Sep. 2014) "A Translatable Predictor of Human Radiation Exposure," PlosOne, 9, 9, e107897. doi.org/10.1371/journal.pone.0107897.

Mu et al. (2014) "Multiplex microfluidic paper-based immunoassay for the diagnosis of hepatitis C virus infection," Anal. Chem. 86, 5338-5344. doi:10.1021/ac500247f.

Nuti et al. (2011) "Identification of circulating bacterial antigens by in vivo microbial antigen discovery," mBio 2, 4, e00136-11. doi: 10.1128/mBio.00136-11.

Oh et al. (2013) "Vertical flow immunoassay (VFA) biosensor for a rapid one-step immunoassay," Lab Chip 13, 768-772. 27 doi:10.1039/c2lc41016h.

Park et al. (Mar. 2017) "Pressed region integrated 3D paper-based microfluidic device that enables vertical flow multistep assays for the detection of C-reactive protein based on programmed reagent loading," Sensors Actuators B 246, 1049-1055. doi:10.1016/j.snb.2017.02.150.

Parolo et al. (2013) "Paper-based nanobiosensors for diagnostics," Chem Soc Rev 42, 450-457. doi:10.1039/c2cs35255a.

Patel (Mar. 25, 2016) "Paper Diagnostic Tests Could Save Thousands of Lives," Scientific American. Retrieved from: https://www.scientificamerican.com/article/paper-diagnostic-tests-couldsave-thousands-of-lives/.

Pauli et al. (2015) "Lab-in-a-syringe using gold nanoparticles for rapid immunosensing of protein biomarkers," Lab Chip 15, 399-405. doi:10.1039/C4LC01123F.

Perry et al. (1995) "Structural Characterization of the Lipopolysaccharide O Antigens of Burkholderia pseudomallei," Infect. Immun. 63, 3348-3352.

Posthuma-Trumpie et al. (2009) "Lateral flow (immuno)assay: its strengths, weaknesses, opportunities and threats. A literature survey," Anal. Bioanal. Chem. 393, 569-582. doi:10.1007/s00216-008-2287-2.

Ramachandran et al. (2013) "A Rapid, Multiplexed, High-Throughput Flow-Through Membrane Immunoassay: a Convenient Alternative to ELISA," Diagnostics 3, 244-260. doi:10.3390/diagnostics3020244.

Reuterswärd et al. (2015) "An 8 minute colorimetric paper-based reverse phase vertical flow serum microarray for screening of hyper IgE syndrome," Analyst 140, 7327-7334. doi:10.1039/C5AN01013F.

Rivas et al. (2015) "Triple lines gold nanoparticle-based lateral flow assay for enhanced and simultaneous detection of Leishmania DNA and endogenous control," Nano Res. 8, 3704-3714. doi: 10.1007/s12274-015-0870-3.

Robertson et al. (2015) "Rapid diagnostics for melioidosis: a comparative study of a novel lateral flow antigen detection assay," J. Med. Microbiol. 64, 845-848. doi:10.1099/jmm.0.000098.

Rosenberg-Hasson et al. (2014) "Effects of serum and plasma matrices on multiplex immunoassays," Immunol.Res. 58:224-233.

Safenkova et al. (2016) "Multiarray on a test strip (MATS): rapid multiplex immunodetection of priority potato pathogens," Anal. Bioanal. Chem. 408, 6009-6017. doi:10.1007/s00216-016-9463-6.

Schilling et al. (2012) "Fully Enclosed Microfluidic Paper-Based Analytical Devices," Anal. Chem. 84, 3, 1579-1585.

Schlappi et al. (2016) "Flow-through Capture and in Situ Amplification Can Enable Rapid Detection of a Few Single Molecules of Nucleic Acids from Several Milliliters of Solution," Anal. Chem. 88, 7647-7653. doi: 10.1021/acs.analchem.6b01485.

Sirisinha et al. (2000) "Recent developments in laboratory diagnosis of melioidosis," Acta Trop. 74, 235-245.

Smith (Jan. 23, 2017) "Immunoassay Markets: Global Analysis and Opportunity Evaluation-2016-2020," PR Newswire. Retrieved from: http://www.prnewswire.com/news-releases/immunoassay-markets-global-analysis-and-opportunity-evaluation-2016---2020-300395286.html.

Squires et al. (2008) "Making it stick: convection, reaction and diffusion in surface-based biosensors," Nat. Biotechnol. 26, 417-426. doi:10.1038/nbt1388.

Sviridov et al. (2009) "Urine albumin measurement: Effects of urine matrix constituents," Clinica Chimica Acta, 404:140-3.

Tate et al. (2004) "Interferences in immunoassay," The Clinical Biochemist Reviews 2004; 25:105-120.

U.S. Food & Drug Administration (Mar. 19, 2015) "Overview of IVD Regulation," Retrieved from: https://www.fda.gov/MedicalDevices/DeviceRegulationandGuidance/IVDRegulatoryAssistance/ucm123682.htm.

Wang et al. (2016) "Multiplexed Detection of MicroRNA Biomarkers Using SERS-Based Inverse Molecular Sentinel (iMS) Nanoprobes," J. Phys. Chem. C Nanometer Interfaces, 120, 21047-21055 DOI: 10.1021/acs.jpcc.6b03299.

Warren et al. (2014) "Point-of-care diagnostics for noncommunicable diseases using synthetic urinary biomarkers and paper microfluidics," Proc. Natl. Acad. Sci. 111, 3671-3676. doi:10.1073/pnas.1314651111.

Wiersinga et al. (2012) "Melioidosis," N. Engl. J. Med. 367:1035-1044. doi:10.1056/NEJMra1204699.

(56) References Cited

OTHER PUBLICATIONS

Wood et al. (2011) "Assessment of urine solute and matrix effects on the performance of an enzyme-linked immunosorbent assay for measurement of interleukin-6 in dog urine," J. Vet. Diagn. Invest. 23:316-320.

Yetisen et al. (2013) "Paper-based microfluidic point-of-care diagnostic devices," Lab Chip, 13, 2210-2251. doi:10.1039/c3lc50169h.

Yuan et al. (2012) "Gold Nanostars: Surfactant-Free Synthesis, 3D Modelling, and Two-Photon Photoluminescence Imaging," Nanotechnology, 23(7): 075102. DOI: 10.1088/0957-4484/23/7/075102.

Yuan et al. (2012) "TAT Peptide-Functionalized Gold Nanostars: Enhanced Intracellular Delivery and Efficient NIR Photothermal Therapy Using Ultralow Irradiance," J. Am. Chem. Soc., 134, 11358-11361. DOI: 10.1021/ja304180y.

Zimmermann et al. (2005) "Modeling and optimization of high-sensitivity, low-volume microfluidic-based surface immunoassays," Biomed. Microdevices 7, 99-110. doi: 10.1007/s10544-005-1587-y.

\* cited by examiner

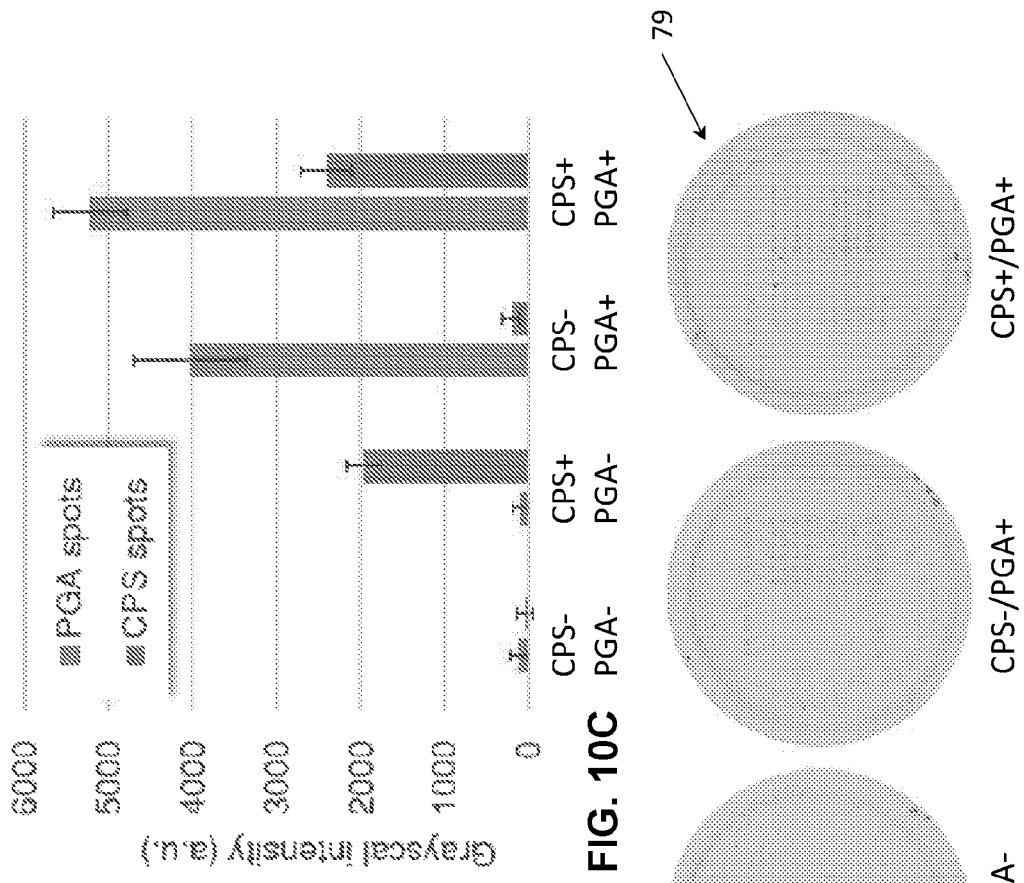
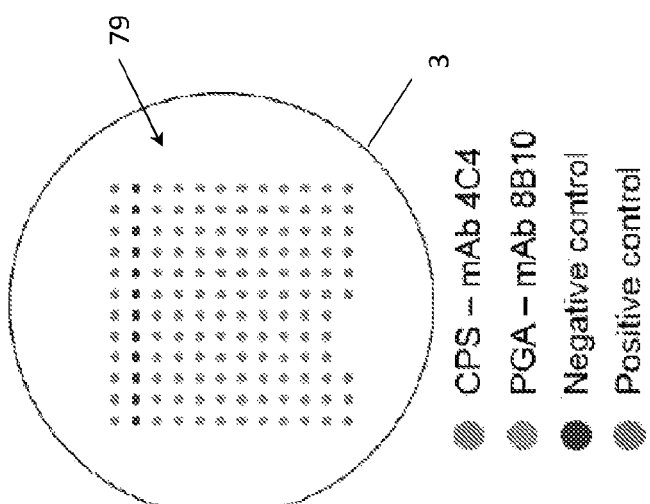
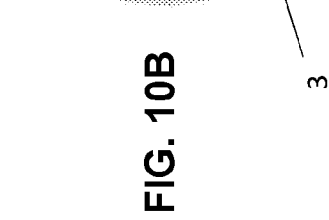
FIG. 10A
FIG. 10C
FIG. 10B

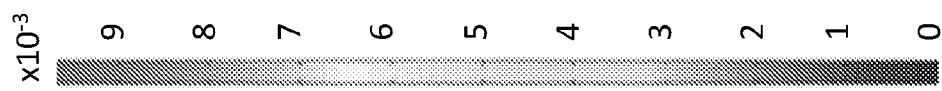
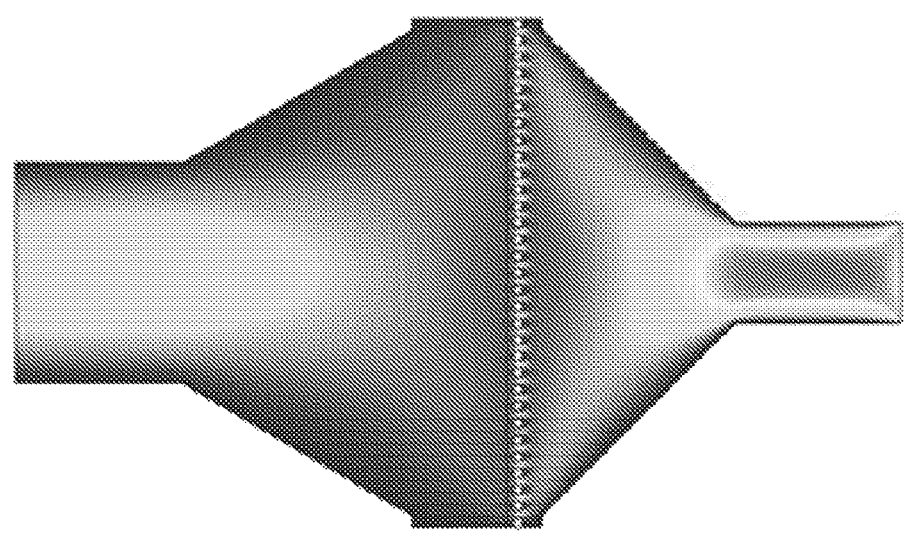
FIG. 11B
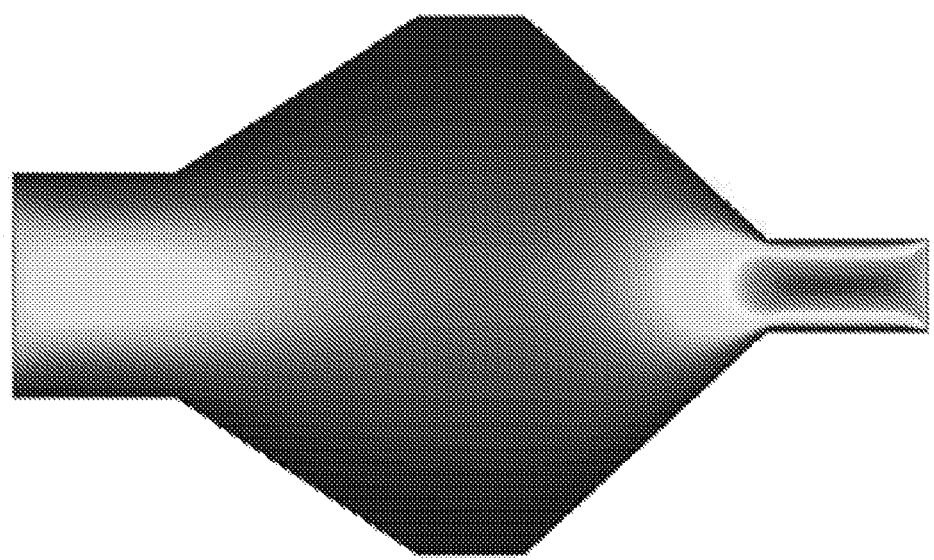
FIG. 11A

Relative Intensity PGS vs. CPA

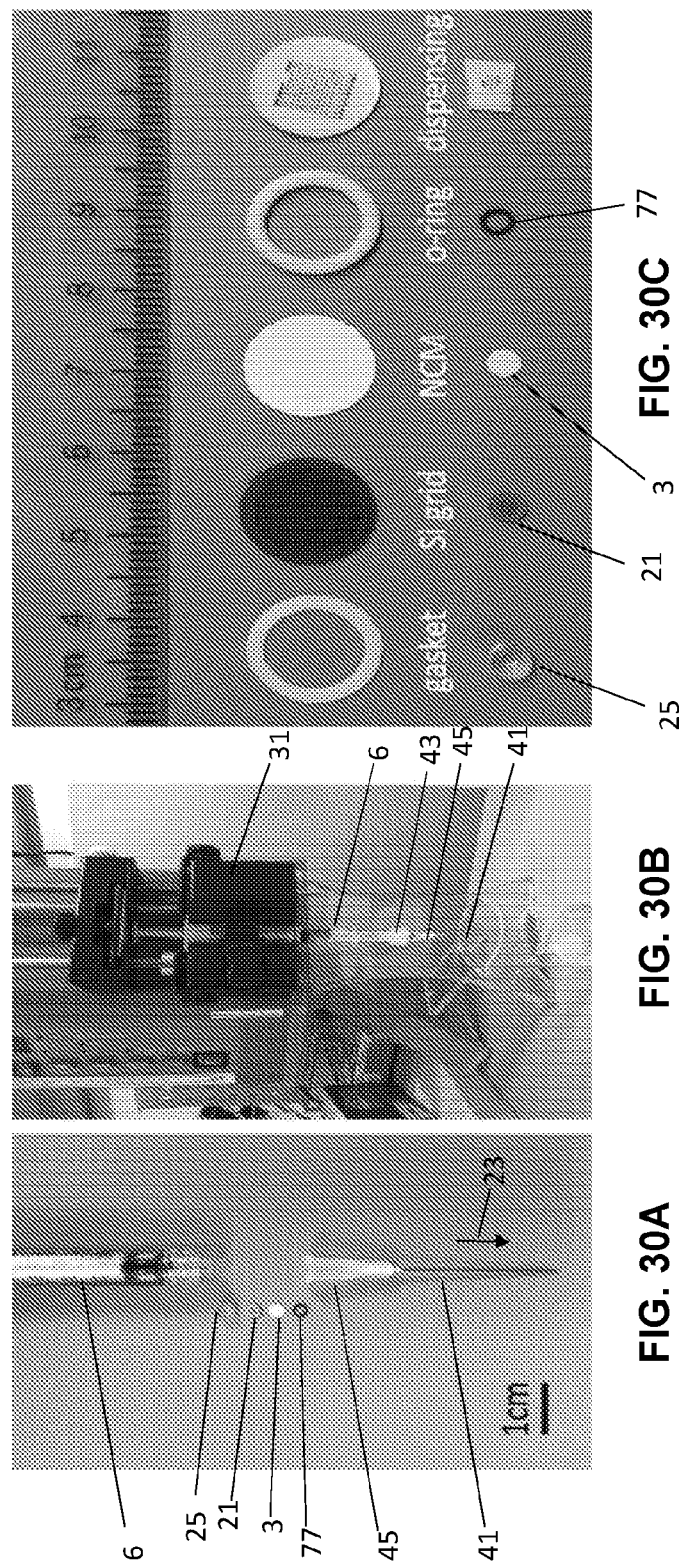

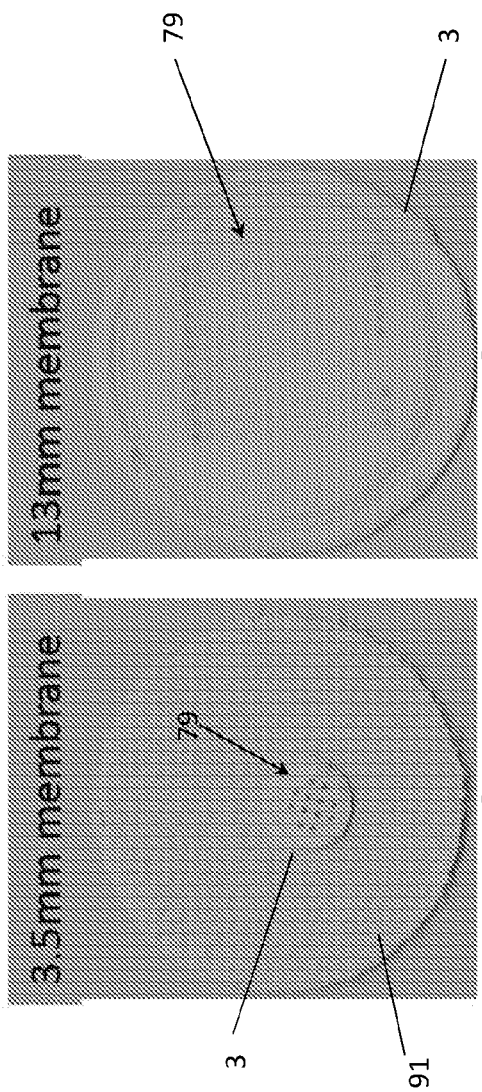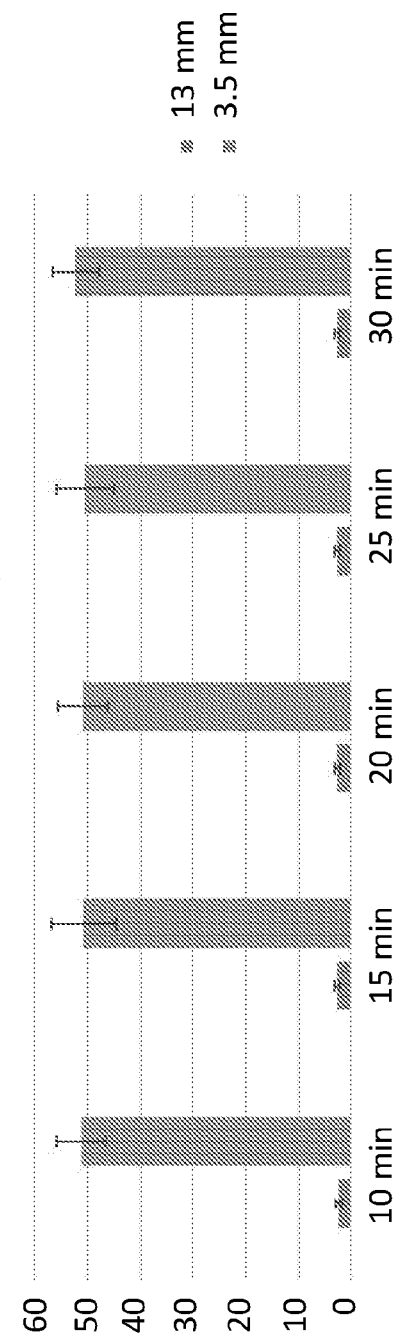

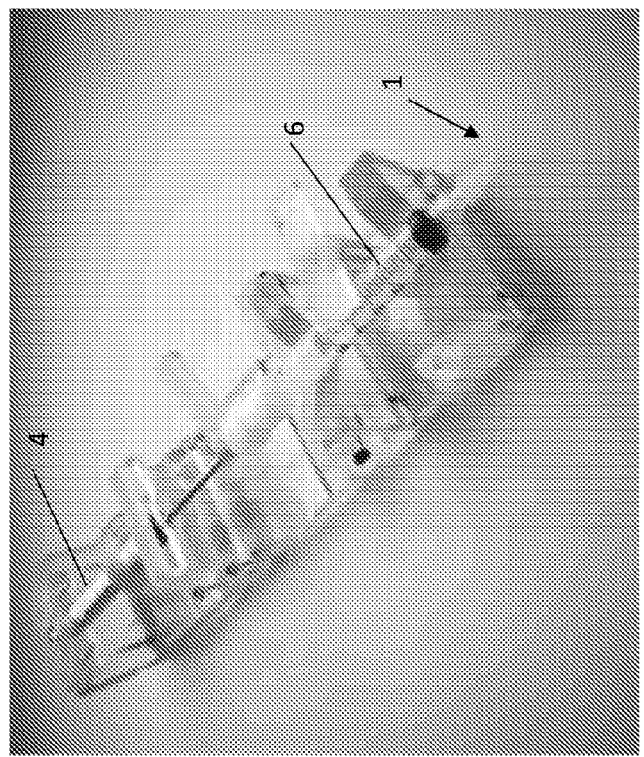
FIG. 44B
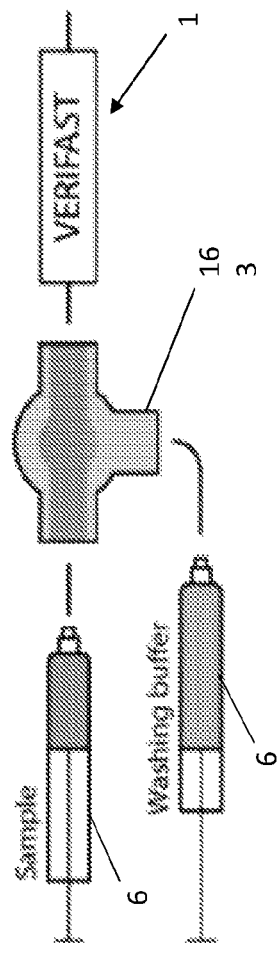 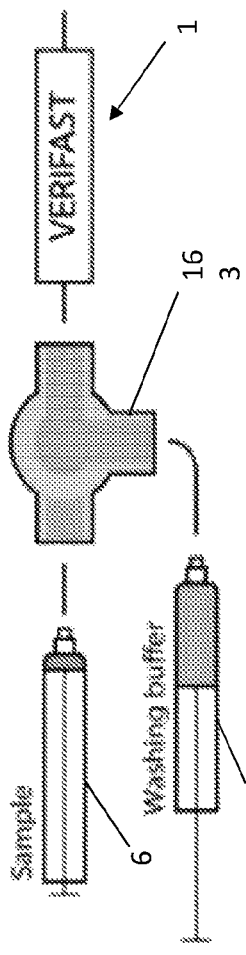
FIG. 44A

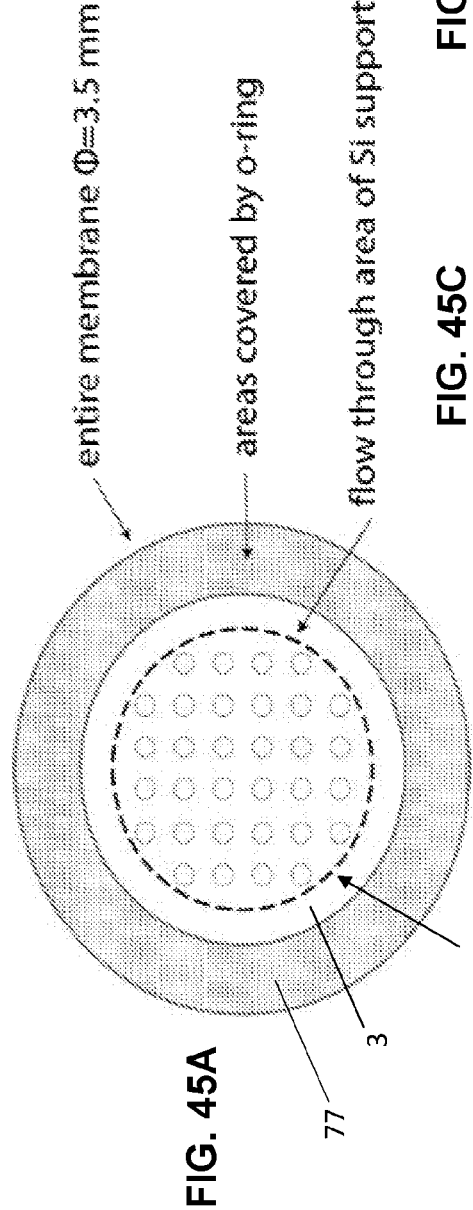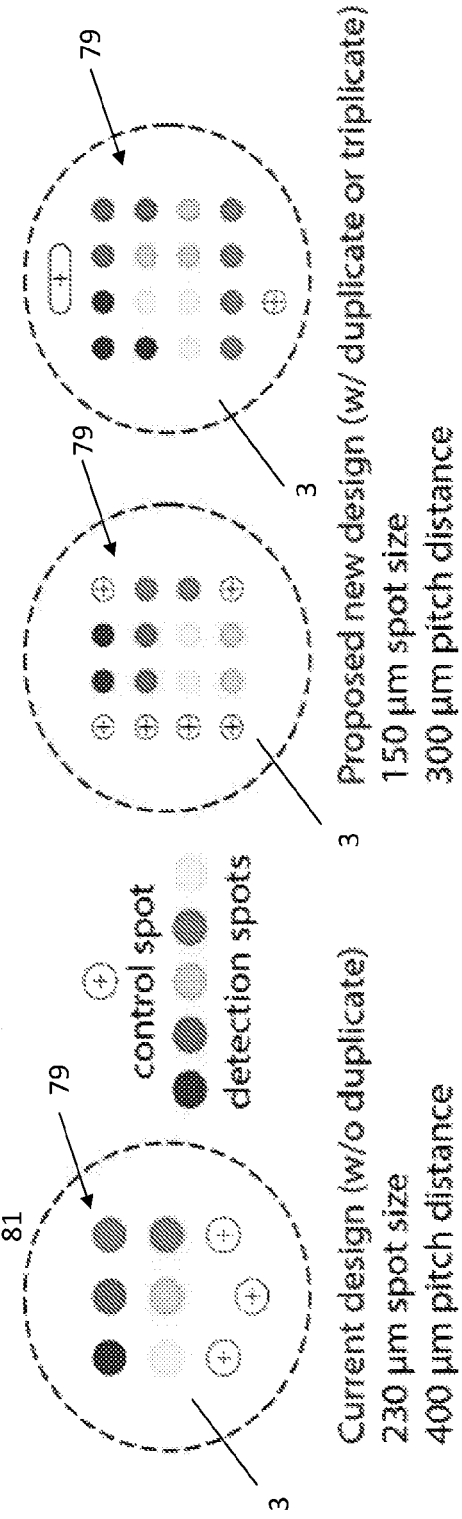
FIG. 45A
FIG. 45B — Current design (w/o duplicate) 230 μm spot size 400 μm pitch distance
FIG. 45C
FIG. 45D — Proposed new design (w/ duplicate or triplicate) 150 μm spot size 300 μm pitch distance

FIG. 47

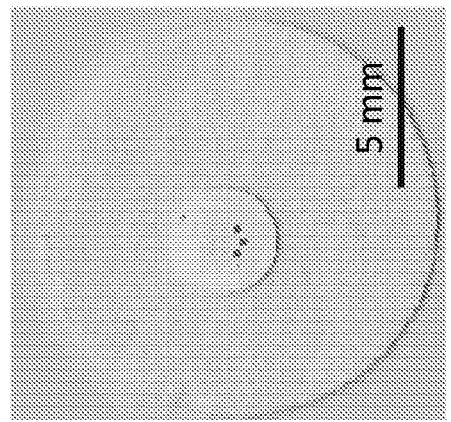
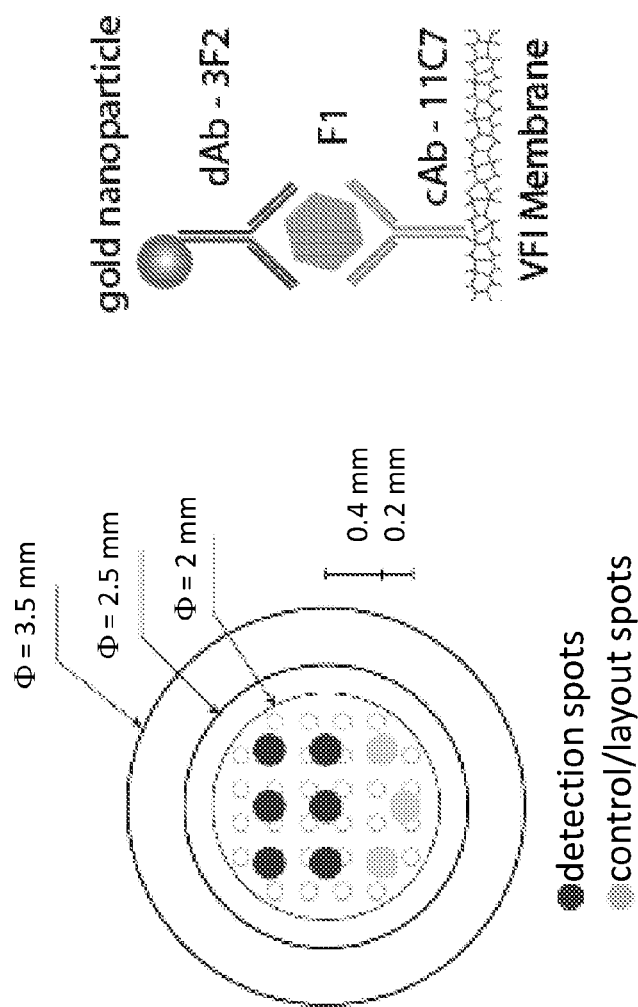
FIG. 48 ian Stage Application filed
VERTICAL FLOW MOLECULAR ASSAY APPARATUS

CROSS-REFERENCE TO RELATED APPLICATIONS

This application is a U.S. National Stage Application filed under 35 U.S.C. § 371 of International Application No. PCT/US2019/024879, filed Mar. 29, 2019, which claims the benefit of U.S. Provisional Application No. 62/650,808, filed on Mar. 30, 2018, which is incorporated by reference herein in its entirety.

STATEMENT REGARDING FEDERALLY SPONSORED RESEARCH OR DEVELOPMENT

This invention was made with United States governmental support under Grant No. HDTRA1-16-C-0026 awarded by the Department of Defense, and Grant No. NNX16A069A awarded by NASA. The government has certain rights in the invention.

BACKGROUND OF INVENTION

There are many instances when biomarkers need to be measured in a point-of-care setting such as cardiovascular disease, cancer prognosis monitoring, infectious disease diagnostics, and biothreat detection. Unfortunately, these biomarkers are at low concentrations and current point-of-care testing solutions are not sensitive enough. Sensitivity can be improved by using smaller pore sizes with a slower flow or novel detection mechanisms such as gold nanoparticles.

The issue with such increase in sensitivity, is that throughput can suffer with slower flow. The devices provided herein address these problems by providing a faster flow for higher sensitivity in a vertical flow configuration device.

SUMMARY OF THE INVENTION

Provided herein are various vertical flow-oriented devices and systems for detecting biomarkers. For example, a vertical flow paper-based immunoassay (VFI) provides a platform adapted for different diagnostic applications. The approach is a simple-to-use design with improved sensitivity and efficiency so that pathogens and toxins are better detected, particularly in resource limited situations.

Provided herein are a range of vertical flow detection devices and methods related thereto. For example, the vertical flow detection device may comprise: a membrane having a first surface and a second surface, wherein the first surface opposibly faces the second surface and the first and second surfaces are separated by a membrane thickness; a plurality of porous structures extending between the first and second surfaces to form fluid conduits from a first fluid chamber formed by the first surface and a second fluid chamber formed by the second fluid surface; a capture agent immobilized on the membrane first surface and/or internally in the membrane between the first and second membrane surfaces; a rigid porous membrane support positioned to mechanically support the membrane and to provide a relatively uniform flow across the membrane first surface exposed to said first fluid chamber during use; a gasket or fluid impermeable material positioned around an outer edge of the membrane; a holder to provide a tight-fit configuration with the membrane and gasket or fluid impermeable material to prevent fluid leakage around the membrane; and a flow device configured to force a fluid sample flow in a direction from the first fluid chamber to the second fluid chamber.

The vertical flow detection device may further comprise a gasket positioned around an outer edge of the rigid support and between the rigid support and the holder.

Any of the vertical flow detection devices may further comprise a detector to detect a target analyte in a fluid sample bound to the capture agent. The devices are compatible with any of a range of detectors. For example, the detector may comprise a scanner or imager configured to scan or image the membrane.

Any of the vertical flow detection devices may have a porous membrane that comprises a material selected from the group consisting of paper, nitrocellulose, polycarbonate and PVDF.

Any of the vertical flow detection devices may have a holder that comprises a standard fitting configured to mount to an imaging system for imaging the membrane without disassembly of the device to provide a complete sample to detection system in a point-of-care setting, wherein the imaging system is optionally a portable imager, scanner, or smartphone. In this aspect, "point-of-care" refers to the ability to obtain a useful image of the membrane in the field and away from conventional labs that would otherwise be required for imaging and attendant diagnostic needs.

Any of the vertical flow detection devices may comprise a plurality of distinct capture agents provided as a spatially discrete array for multiplexed detection of two or more different target analytes.

Any of the instant vertical flow detection devices may be configured to accommodate bi-directional flow, the device further comprising: a top and a bottom diffuser membrane with the membrane provided between the top and bottom diffuser membrane; an additional rigid porous membrane to provide a first rigid porous membrane support and a second rigid porous membrane support, wherein the first rigid porous membrane is adjacent to an exposed surface of the top diffuser membrane and the second rigid porous membrane support is adjacent to an exposed surface of the second diffuser membrane; a first gasket integrated with the first rigid porous membrane support and a second gasket integrated with the second rigid porous membrane support to provide additional support and sealing, including two gaskets for each surface of the rigid supports to provide sealing with the membranes and holder to make sure all fluid passes the center area of the membranes, and, optionally, wherein the gaskets are integrated with the rigid supports. The top and bottom diffuser membranes provide a relatively uniform flow through the membrane, including the membrane first surface having capture agent immobilized thereto.

The vertical flow detection device may further comprise two o-rings, with a first o-ring supported by a top surface of the first rigid porous membrane support and the second o-ring supported by a bottom surface of the second rigid porous membrane support to ensure good sealing between the fluid chambers and the membrane support.

Any of the vertical flow detection devices described herein may have a capture agent that comprises an antibody, and the target analyte specifically binds to the antibody, and a detectable label is connected directly or indirectly to the target analyte. For example, the detection label may be part of a sandwich immunoassay.

Any of the vertical flow detection devices may have a membrane that comprises one or more porous solid state materials, including plastic and polymers, paper, nitrocellulose, cellulose, PVDF, polycarbonate, ceramic, metallic materials, glass (including glass microfibers), and/or anodized aluminum.

Any of the vertical flow detection devices may be described in terms of a characteristic pore size of the membrane, such as a characteristic pore size that is less than 10 µm, less than 1 µm, less than 0.5 µm, or less than or equal to 0.1 µm, including with a lower limit that has a characteristic pore size that is greater than 0, or greater than 0.001 µm, or greater than 0.01 µm or greater than 0.1 µm; and/or by a porosity, such as a porosity of between 10% and 95%, and any subranges thereof. Any of the membranes may have a porous structure that is interconnected or fibrous. Any of the membranes may be described in terms of a thickness, such as an average thickness, including a thickness that is greater than or equal to 1 µm and less than or equal to 1000 µm, and any subranges thereof.

Any of the vertical flow detection devices may have a porous membrane support characterized by a pore size, such as a pore size that is greater than or equal to 1 µm and less than or equal to 1000 µm and spatially arranged to provide a substantially uniform flow rate profile across the membrane.

Any of the vertical flow detection devices may be configured for use with a target analyte that comprises one or more of: DNA, RNA, an antigen, a polypeptide, a protein, or a metal ion.

Any of the vertical flow detection devices may have a plurality of capture agent spots and a capture agent spot size of between 1 µm and 5 mm. The fluid sample flow may be uniformly directed to the capture agent spots. "Uniformly directed" refers to introduction of fluid sample across the membrane in a manner such that there is less than 20% variability in fluid flow speed between different spots. In this manner, issues with non-uniform flow are avoided. To further assess that flow is suitably uniform, positive and/or negative controls can be dispersed over the membrane.

Any of the vertical flow detection devices may be described as having an exposed to flow membrane surface area to receive a fluid flow. The devices may further comprise means for adjusting an exposed to flow membrane surface area, wherein the exposed to flow membrane surface area is selected based on a desired flow-rate and sample volume, with surface area increasing for increasing sample volume. Similarly, for a given amount of fluid delivered to the membrane surface, the flow-rate may be varied by varying the surface area, thereby varying the fluid flux through the membrane (e.g., fluid flux=Q/area, wherein Q is the flow-rate, area is the membrane surface area which can be adjusted, thereby varying fluid flux through the membrane).

Exemplary means for adjusting includes: an adjustable gasket, an impermeable layer covering a portion of the membrane (including by printing of an impermeable material on the membrane, such as wax printing, SU photolithography, or other printing methodology known in the art), and a mask layer positioned over the membrane. By varying the footprint or surface are of the impermeable layer or the mask layer, including by swapping out a layer having a lower surface area that blocks fluid access to the membrane with a higher surface area, the effective fluid flow-rate through the membrane increases.

The vertical flow detection device is compatible with a range of flow-driving components, such as a flow device that is a syringe, a pump, or a passive capillary driven system.

Any of the devices described herein may further comprise a positive control spot on the membrane for validation of the device and any corresponding method.

Any of the vertical flow detection devices described herein may be used to detect an analyte in fluid sample. For example, a method of detecting an analyte in a fluid sample may comprise the steps of: providing any of the vertical flow detection devices described herein; forcing a flow of fluid sample from the first fluid chamber to the second fluid chamber through the plurality of pores in the membrane; binding a target analyte present in the fluid sample to a capture agent; and detecting the target analyte bound to the capture agent with the detector.

The method may accommodate bi-directional flow so that sample can be repeatedly directed in opposite flow directions to improve sample detection and sample usage. In this manner, any of the methods may comprise sequential flowing fluid sample in a direction from the membrane first surface to the membrane second surface, after a desired time, switching the flow direction to an opposite direction from the membrane second surface to the membrane first surface. Any number of flow direction sequential switches may be used, such as greater than or equal to 2, between 2 and 10, between 3 and 7, or any sub-ranges thereof.

The forcing step may comprise pumping of the fluid sample by generating a higher pressure in the first fluid chamber relative to a lower pressure in the second fluid chamber.

The forcing step may comprise pumping of the fluid sample by generating a higher pressure in the first fluid chamber relative to a lower pressure in the second fluid chamber and subsequently generating a higher pressure in the second fluid chamber relative to a lower pressure in the first fluid chamber, thereby providing controlled bi-directional flow, including in a sequential manner, to further increase sensitivity by maximizing the likelihood of an analyte being successfully captured by the capture agent.

The pumping may generates a flow speed in a direction perpendicular to the membrane that is between 0.1 mm/s and 10 mm/s.

The flow rate (including fluid flux or fluid speed) may be selected to generate a shear stress through the pore that is less than a maximum shear stress corresponding to detachment of a bound target analyte from the capture agent.

Any of the methods may further comprise the step of detecting at least one additional target analyte with at least one additional different capture agent, thereby providing multiplex detection.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 10A is a schematic diagram showing design of a microarray of a VFI membrane of the disclosed device for CPS and PGA multiplexing VFI with detection of CPS and PGA on the same membrane. FIG. 10B are scanned images of the four membranes with different samples (CPS−/PGA−, CPS+/PGA−, CPS−/PGA+, CPS+/PGA+) for the design of FIG. 10A. Detection spots showed positive signals only when the corresponding antigen was present in the sample. FIG. 10C is a plot of histograms of the multiplexing membranes of FIG. 10B.

FIGS. 11A-11E show the results of in-silico experiments of the fluid and pressure inside the filter holder of the device of FIG. 2.

FIGS. 30A-30C depicts conceptual work to reduce the size of the membrane.

FIGS. 31A-31C are depict experiment setup and gray scale intensity results for testing of the 3.5 mm membrane setup with the CPS (5 ng/mL) assay at 0.5 mL/min flow.

FIGS. 44A and 44B depict designs of an actuator and gas syringe for pushing liquid through the membrane.

FIGS. 45A-45D illustrate example aspects of membrane array printing.

FIG. 47 is a plot of signal intensity for 25 ng/ml LcrV spiked into either buffer or serum.

FIG. 48 is a summary of a layout of a VFI assay for detection of a biothreat (plague) as assessed by detection of F1 antigen. The left panel illustrates a substrate having detection spots (illustrated by six spots toward top) and control/layout spots (illustrated by three spots below the detection spots). The middle panel illustrates the configuration of the detection spots, with an antibody specific for the target (e.g., F1, in this example associated with plague), a detection label corresponding to a gold nanoparticle antibody. The right panel is a photograph of the resultant F1 detection VFI assay.

FIG. 51 summarizes processing steps for the detection of nucleic acid.

FIG. 52 illustrates detection of nucleic acids in a vertical flow paper-based platform (VFP). The top panel illustrates a process to obtain nucleic acids that can be introduced to the VFP assay. The bottom panel illustrates a general configuration of the components connected to the membrane, including capture antibody (e.g., anti-biotin mAb) having an accessible 5' Biotin-modified primer to selectively bind a target sequence of a target gene, including a target gene that has been amplified. A detection antibody (e.g., gold labeled anti-FITC mAb) can selectively bind to the target gene that has been captured by the capture antibody.

FIG. 53 is a plot of colorimetric intensity for positive (RNA-containing) samples and negative (buffer solution only) and demonstrates the systems and processes have high specificity for nucleic acids, in this example CDKN1A amplicon diluted in 1 mL buffer solution. The negative sample is the buffer solution without the amplicon. Reverse: biotin; Forward: FITC FIG. 54 is a plot of colorimetric intensity for samples without HIST1H3D and without CDKN1A (Hist−/CDK−), with only CDKN1A amplicon (Hist−/CDK+) and with only HIST1H3D amplicon (Hist+/CDK−). CDKN1A: Reverse: biotin; HIST1H3D: Revers: digoxigenin (DIG).

FIG. 55 top panel is a summary of an assay where cells are irradiated with radiation and compared to non-irradiated cells. The bottom left panel is the result using agarose gel electrophoresis and indicates that the agarose technique cannot reliably differentiate between non-exposed cells and cells exposed to 5 Gy radiation. The bottom right panel illustrates the instant vertical flow systems are capable of distinguishing between cells that have been irradiated (5 Gy—higher colorimetic intensity values) than non-irridiated cells (0 Gy—the lighter bars on the left side of the pair and having lower colorimetric intensity).

DETAILED DESCRIPTION OF THE INVENTION

In general, the terms and phrases used herein have their art-recognized meaning, which can be found by reference to standard texts, journal references and contexts known to those skilled in the art. Where applicable in the following description, definitions of specific terms and phrases are provided to clarify their specific use in the context of the invention.

Example 1: Paper-Based Vertical Flow Immunoassay (VFI) for Diagnosis of Bio-Threat Pathogens During the last century, in parallel to progress made in basic and applied microbiology, there has been concerning advances made toward the weaponization of biological agents and biotoxins (Jansen et al., 2014; L W et al., 1997). Currently, there are nearly seventy biological agents listed by the U.S. Department of Health and Human Services as potential threats to public health and national security. Exposure to these agents can cause a variety of human and animal diseases (Higgins et al., 1999; Lakoff, 2008). *Burkholderia pseudomallei*, a soil and water dwelling bacterium that causes the deadly disease melioidosis in human and animals, is considered a high priority biological threat because of its potential to be weaponized and ability to produce fatal diseases. Recently, the total number of melioidosis cases worldwide has been estimated to be 165,000 of which 89,000 people die (Limmathurotsakul et al., 2016). Melioidosis can be very challenging to diagnose and treat, as current diagnostic method often lack the required sensitivity. Melioidosis has broad clinical manifestations that range from mild infection of the skin and soft tissues to organ abscesses (Wiersinga et al., 2012), and is one of the most common sources of community-acquired sepsis in many tropical and subtropical regions of southeast Asia and northern Australia (Limmathurotsakul et al., 2016). Infections vary from mild disease to overwhelming septicemia within 24 to 48 hours after symptom onset, and untreated cases of melioidosis have a fatality rate as high as 90% (Limmathurotsakul et al., 2010b). Early diagnosis and treatment are key factors in improving disease management and lowering the mortality rate of infected patients (Currie et al., 2010).

Despite several advances in immunological and molecular approaches to detect *B. pseudomallei* (Sirisinha et al., 2000), culturing of *B. pseudomallei* from clinical samples (e.g. blood, urine, pus, sputum, etc.) remains the gold-standard for melioidosis diagnosis. However, laboratory culture is very time-consuming and often challenging due to the low levels of bacteria present in many clinical samples. Culture and other molecular diagnostic approaches, including PCR, require sophisticated equipment and highly-skilled personnel that are often unavailable in resource-restricted regions. These difficulties can lead to the infection being misdiagnosed and grossly underreported in these areas (Limmathurotsakul et al., 2010b). Moreover, recent statistical studies have found that the culture method is not a reliable gold standard for diagnosis of melioidosis infection due to low sensitivity (Limmathurotsakul et al., 2010a). For these reasons, there is a crucial need for a simple, rapid, point-of-care (POC) diagnostic tool that can quickly and accurately detect bio-threat agents such as *B. pseudomallei* from clinical samples.

With the advancement of nanotechnology and bio-sensing technology, paper materials have been utilized for biomedical applications (Hu et al., 2014; Parolo and Arben Merkogi, 2013; Warren et al., 2014; Yetisen et al., 2013). Paper based devices have been reported to detect proteins (Li et al., 2010), nucleic acids (He et al., 2012), and cellular activities (Liu et al., 2009). A majority of the reported paper devices are designed in a lateral flow immunoassay (LFI) format where the fluid flow is parallel to the surface of the paper. This format typically consists of several paper segments joined together with a backing layer (Yetisen et al., 2013) and the testing fluid is transported through these segments by the capillary force of the paper. The main benefits of LFI include low cost, rapid results, flexibility and ease of use. However, in order to achieve an adequate flow rate, the pore size of the paper materials are limited to several micrometres and above, which could hinder the biomolecule capturing and thus the assay's sensitivity.

In addition, sample volume constraint and the difficulties of multiplexing are other hurdles that confront LFI development. Several LFI prototypes for multiplexing detection have been reported using a paper device with branched geometry (Li et al., 2011; Mu et al., 2014), multiple testing lines (Rivas et al., 2015), and microarray (Helene and Svahn, 2014; Lafleur et al., 2012; Safenkova et al., 2016). Overall, the number of integrated assays is still limited and they require careful design of the membrane geometry and microarray layout to prevent cross-contamination so that the upstream reactions do not affect the downstream reactions.

One approach to improving upon the LFI platform is the use of vertical flow-through devices. This alternative format is similar in that it is a membrane based immunoassay, however, fluids are applied vertically to the surface of the paper rather than parallel (Desmet et al., 2011; Oh et al., 2013; Pauli et al., 2015). One design simply replaces the conventional lateral flow segments in a stacking manner, and allowing the liquid to diffuse from the bottom to the top layers (Eltzov and Marks, 2017; Herendarcikove et al., 2017; Park and Park, 2017). Another method is to push the assay reagents through one single membrane in steps, and allow for the targets to react with the reagents on the membrane. A vertical flow allergen microarray assay was built with to detect IgE activities in human serum samples with allergen components (Chinnasamy et al., 2014; Reuterswsrd et al., 2015). Similarly, an immunofiltration assay for simultaneous detection of HIV p24 and hepatitis B virus antigens was recently reported (Cretich et al., 2015). Another vertical flow platform was developed using 96-well vacuum plate to draw reagents through a nitrocellulose membrane to detect IgM specific to the lipopolysaccharides (LPS) derived from *Salmonella typhi* (Ramachandran et al., 2013). Recent efforts have been made to investigate the possibilities of coupling the vertical flow assay with more advanced readout technologies, such as the surface-enhanced Raman spectroscopy (SERS), toward higher sensitivity (Berger et al., 2016; Clarke et al., 2017).

This example presents a paper-based vertical flow immunoassay (VFI) device for the detection of bio-threat pathogens. *B. pseudomallei*, the causative agent of melioidosis, was used as the model bacterium. Previous studies have validated the capsular polysaccharide (CPS), a polymer of 1, 3-linked 2-O-acetyl-6-deoxy-b-D-manno-heptopyranose residues, as a diagnostic biomarker for *B. pseudomallei* (AuCoin, 2012; Nuti et al., 2011). It has also been shown that CPS can be successfully detected via LFI (Houghton et al., 2014; Robertson et al., 2015). It is clear that some melioidosis patients have low levels of CPS that are undetectable by the CPS LFI. In this example, VFI parameters were optimized in order to develop a POC assay with improved sensitivity and both simplex and multiplex detection capabilities of biothreat pathogens.

There are a number of important parameters that needed to be considered in order to optimize the VFI platform of the disclosed device. The VFI membrane area is large, but the sensing spots with surface reagents can be reduced in size by depositing small volumes of reagents. This allows for multiplexed detection by incorporating different assays on the same membrane creating a spatially independent spot microarray. Previous work reported that increasing the sample volume could improve the sensitivity of flow-through immuno-sensors (Pauli et al., 2015). However, the effect of sample flow rate has not been studied with the vertical flow devices. Flow rate is an important factor as it impacts the time needed to perform such assays, and point-of-care devices by definition are rapid. In the VFI platform of the disclosed device, this example demonstrates that increasing the sample flow rate directly increases the sample volume per unit area, thus improving the VFI-based assay's sensitivity. Lastly, the flow path of VFI device was dramatically reduced to only the thickness of the membrane compared to a flow path of several centimetres in the LFIs. This allowed for the utilization of membranes with submicron pore sizes. Results demonstrate that use of nanopore membranes can significantly improve the sensitivity of the VFI's assay.

Analysis of paper-based immuno-biosensor: FIG. 1A illustrates the principle of a paper-based immuno-biosensor in the vertical flow format, as used in the disclosed vertical flow detection device 1. The porous structures 11 of membrane 3 were approximated as bundled tubes to help estimate the transport process, as shown in FIG. 1B. In a porous material 24 with pore radius d, a liquid flows through the membrane 3 with a flow 23 velocity of $\vec{\mu}$, and a sensing length of $L_s$, which is the detectable thickness 9 of the membrane 3. The sensing area (also the imaging surface) is the top surface $A_v$, e.g., first surface 5, which is a circular shape with radius $R_m$; a second surface is on the bottom (no observable) side of the membrane separated by membrane thickness 9. FIG. 1C illustrates an internal surface of the porous structure 11 is coated with capture antibody, e.g., capture agent 19, with a surface concentration of γ. The diffusivity of the target is D, and the antigen-antibody pair has an association constant of $k_{on}$, and mass transfer coefficient $k_c$.

There are two critical dimensionless numbers in the VFI system (Schlappi et al., 2016; Squires et al., 2008; Zimmermann et al., 2005). The first one is the Damköhler numbers ($D_a$), which characterizes the relation between adsorption rate and transport rate.

$$D_a = \frac{\text{adsorption rate}}{\text{transport rate}} = \frac{k_{on} \cdot \gamma}{k_c} \tag{1}$$

The second one is the Péclet number ($P_e$), which can be used to compare convection rate and diffusion rate.

$$P_e = \frac{\text{convection rate}}{\text{diffusion rate}} = \frac{u/L_s}{D/d^2} \tag{2}$$

Figures 1A, 1B, 1C:
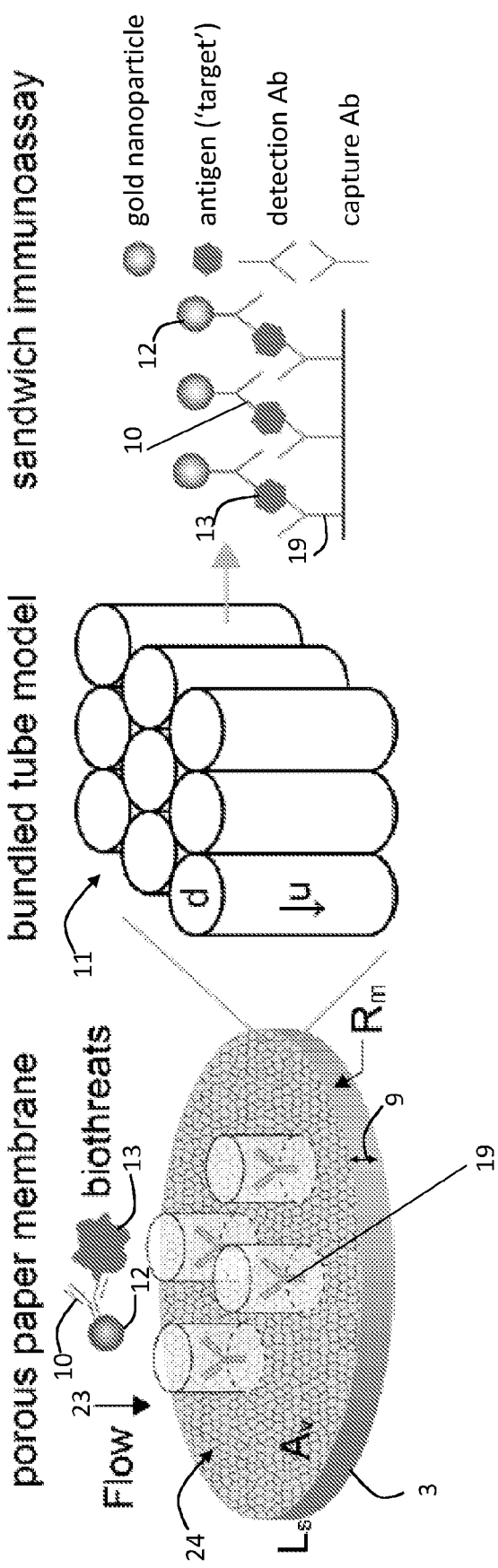
FIG. 1A is a schematic diagram of a paper-based immunoassay in a vertical flow format. As the sample is pushed through the porous membrane, the targets interacts with the components on the membrane, such as reacting with components that are reagents of the targets.
FIG. 1B is a schematic diagram of the internal surface of the porous structures of the paper membrane, approximated as cylinders.
FIG. 1C is a schematic diagram of the design of the sandwich assay to detect the biothreats. The detection antibody labelled with gold nanoparticles generates colorimetric signals as system readout.

To capture target antigen 13 with low concentration, two conditions are desired: (1) Efficient capture assay ($D_a \gg 1$), in which the rate of the antigen 13 binding to the capture antibody 19 is faster than the rate of antigen 13 molecules transport to the pore wall of, e.g., porous structure 11. High flow speed 23 increases the transport rate $K_c$, decreases $D_a$, and reduces the capture efficiency. However, this can be counterbalanced by using an assay with fast binding kinetics. In this example, the focus was on low concentration antigen 13 detection with high capture antibody density, thus assuming the capture is fast enough to ensure $D_a \gg 1$. (2) Non-diffusion-limited assay ($P_e < 1$), allows for all delivered antigens 13 to diffuse to the pore wall before they are convected through the sensing area. Previous simulation showed that keeping $P_e < 1$ ensures >90% capture efficiency (Schlappi et al., 2016). Setting $P_e < 1$ in Equation (2) provides the following constraint on the volumetric flow rate (Q):

$$Q < \frac{\Phi D L_s A_v}{d^2} \qquad (3)$$

Here $\phi$ is the porosity of the membrane 3. According to Equation (3), decreasing the membrane 3 pore size is an effective way to increase the maximum flow 23 rate Q to allow more antigen 13 to be detected by the sensor. Based on the theoretical analyses, it was determined a VFI design for device 1 with high flow 23 speed and small membrane 3 pore size could improve the assay sensitivity.

Figures 2A, 2B, 2C:
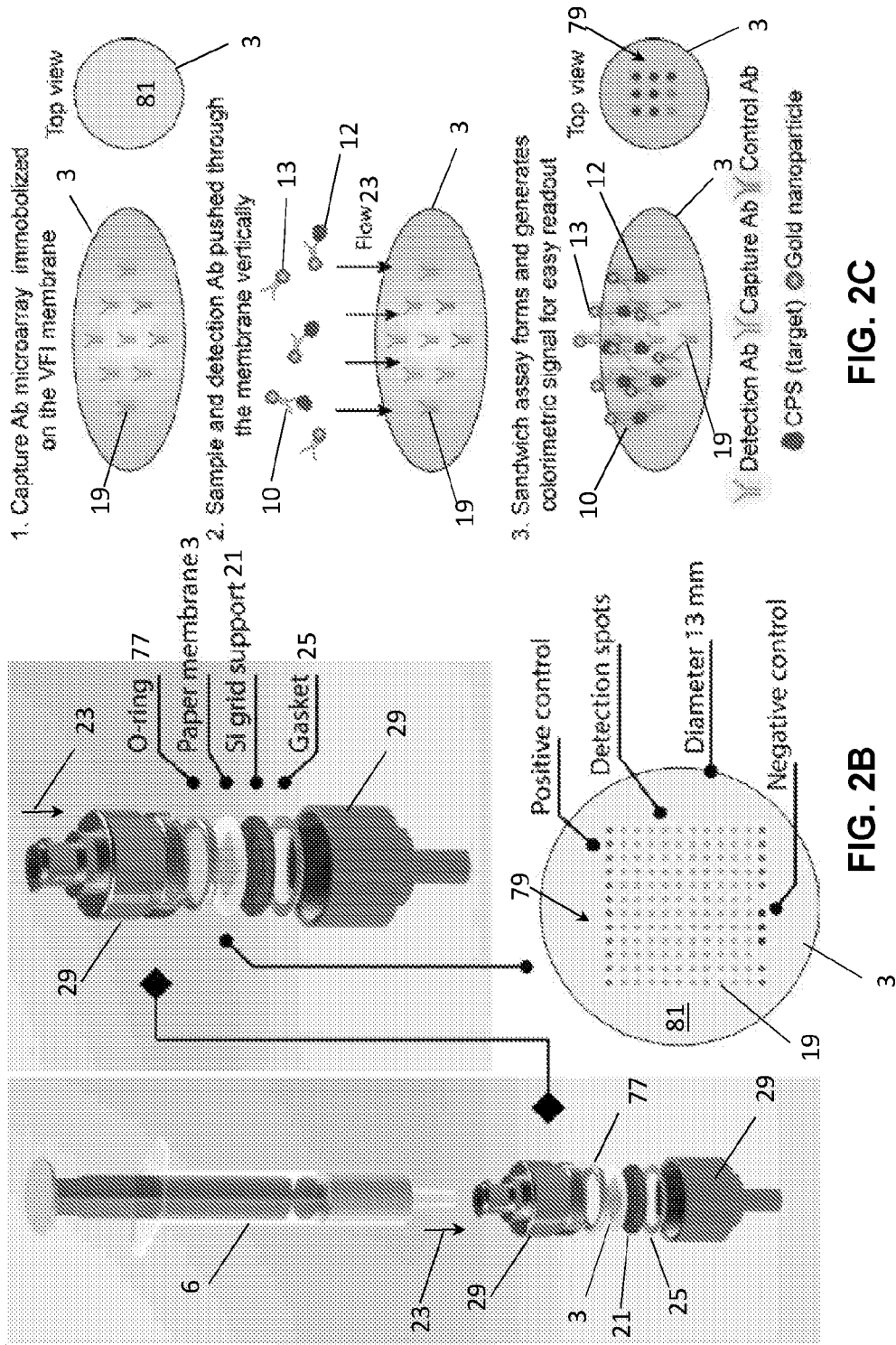
FIG. 2A is a schematic diagram of a scheme of a VFI device and its operation principle. The platform can be based on an 0=13 mm nitrocellulose membrane encapsulated in a stainless steel filter holder with supporting grid and sealing gaskets.
FIG. 2B is a schematic diagram of a layout of capture agent microarray of a VFI device, including detection spots (mAb 4C4), positive control spot (goat anti-mouse IgM+IgG+IgA), and negative control spot (1×PBS).
FIG. 2C is a schematic diagram illustrating operation principles of a VFI device platform.

MATERIALS AND METHODS: Construction of the VFI platform: As shown in FIG. 2A, the VFI platform of device 1 comprises a 13 mm diameter nitrocellulose membrane 3 (the actual flow through area is 10 mm diameter) encapsulated in a stainless steel filter holder 29 (Swinny Filter Holder 13 mm, Millipore, MA, USA) together with supporting and sealing components, e.g., support 21 and holder 29. A polytetrafluoroethylene (PTFE) gasket 25 and o-ring 77 are placed below and on top of the paper membrane 3 respectively to seal the liquid pathway and prevent leakage. A syringe 6 and pump 31 (FIG. 30B) (New Era Pump Systems, Inc., NY, USA) can push the samples and reagents vertically through the paper membrane 3 at a controlled flow 23 rate.

In previous vertical flow systems, where a commercial stainless steel membrane support was used, large signal variation was reported in membranes with pore size larger than 0.1 µm (Chinnasamy et al., 2014). It was suspected the variation came in part from the flexibility of the stainless steel support. Therefore, the support 21 is fabricated with silicon, which has a higher Young's modulus than stainless steel, using deep etching method. The silicon grid mechanically supported the membrane 3 against the flow 23 with less deformation, thus reducing the signal variation. Accordingly, any of the devices provided herein may use a support formed of a material having a higher Young's modulus than that of stainless steel, including a silicon grid.

The VFI in device 1 can be made using nitrocellulose membrane 3 because of its high protein-binding capability (Lu et al., 2010) and availability in a range of small pore sizes. Four nitrocellulose membranes, Amersham Protran 0.1 µm NC, 0.2 µm NC, 0.45 µm NC, and Whatman AE98 (pore size 5 µm) (GE Healthcare Life Sciences, PA, USA), are tested and compared. The membranes are cut into 13 mm diameter disks using a $CO_2$ laser (VersaLaser 2.30, Universal Laser Systems, AZ, USA). The capture antibody microarray is dispensed onto the paper disks using a micro solenoid robotic dispenser (AD1520 micro-dispenser with BioJet Elite, Biodot, CA, USA) with a droplet volume of 1 nanolitre creating a circular spot with 220 µm diameter.

*Burkholderia pseudomallei* detection microarray: Detection of the *B. pseudomallei* is based on a sandwich immunoassay targeting the CPS, a capsular antigen 13 that is shed by the bacterium during infection (Nuti et al., 2011). Capture antibody 19 is immobilized on the paper membrane 3 as an array of capture agent spots 79 using the Biodot micro-dispenser. FIG. 2B shows the layout of the *B. pseudomallei* detection microarray that comprises 120 replicated detection spots 79, 3 negative control spots 79, and 19 positive control spots 79. In the detection spots 79, CPS specific mAb 4C4 (10 mg/mL) is deposited with one 1 nL droplet per spot 79. In positive control spots 79, goat anti-mouse IgM+IgG+IgA (1 mg/mL) (SouthernBiotech, Birmingham, AL, USA) is deposited with three 1 nL droplets per spot 79. In negative control spots 79, 1×PBS is deposited with one 1 nL droplet per spot 79. The dispensed membrane 3 is stored at room temperature in an aluminium pouch with silica desiccant until use. The detailed processes of bacterial isolation and culture, biomarker discovery, and monoclonal antibody affinity characterization were introduced in a previous report (Nuti et al., 2011).

VFI operation workflow: CPS is a linear polymer composed of repeating saccharide units (Perry et al., 1995). As a result, the repeating epitope binding sites allow for the same antibody to be used for capture and detection of CPS. In the VFI workflow shown in FIG. 2C, CPS-specific mAb 4C4 was immobilized on the paper membrane 3 as the capture antibody array and 4C4-labeled gold nanoparticle 12 (4C4-GNP) was used as the detection agent. The 4C4-GNP 12 stock solution was prepared through passive absorption of mAb 4C4 to 40 nm diameter colloidal gold. After washing to remove free antibody, the 4C4-GNP 12 solution was concentrated to an OD=9 at 540 nm, which equals to a concentration of 1.5 nM. As the CPS and 4C4-GNP 12 were pushed through the membrane 3, the antigen 13-antibody 10 complex bound to the capture agent 19 antibody spot 79 array, forming the sandwich assay. After the experiment, the membrane 3 was scanned with a regular table-top scanner to extract the colorimetric signals generated by the gold nanoparticles 12 as shown in the "Top View" in FIG. 2C. The VFI test procedure can be completed in less than 30 min.

Detailed experimental procedure included flowing 1 mL of 1×PBS (phosphate buffered saline, Gibco, MA, USA) through the membrane 3 for equilibration of the membrane 3. The membrane 3 was then treated by flowing blocking buffer (10 mM borate buffer containing 2.5% Triton X-100, pH=8) to block the membrane 3 and prevent non-specific binding. CPS spiked assay buffer solution (0.1 M PB buffer containing 0.1% Triton X-100 and 0.1% BSA, pH=7.2) were pushed using syringe 6 flow device (e.g., pump 31) through the membrane 3 at a controlled flow 23 rate and duration. Two reaction schemes, namely sequential and premixing protocol are tested.

Sequential protocol: The CPS spiked assay buffer solution was pushed through the membrane 3 to allow the CPS to bind to the capture antibody agent 19 on the membrane 3. The 4C4-GNP 12 solution was then pushed through the membrane 3. During the second step, the 4C4-GNP 12 bound to the CPS that was already captured and bound to the capture antibody agent 19 on the membrane 3.

Premixing protocol: The CPS spiked assay buffer solution was pre-mixed with the 4C4-GNP 12 for 10 min. This premixing step provides additional time for the 4C4-GNP 12 to bind the free CPS in solution. This mixture was then pushed by syringe 3 through the membrane 3 to allow capture of the CPS-4C4-GNP 12 complex by the capture antibody 19 on the membrane 3.

After the sample was processed, the membrane 3 was washed by flowing 1.5 mL blank assay buffer through the membrane 3 to remove non-specific or loosely bound proteins and excess 4C4-GNP 12. The VFI device 1 was dismantled and the membrane 3 was placed on a filter paper (Whatman qualitative filter paper, Grade 1, GE Healthcare Life Sciences, PA, USA) for 5 min as a fast drying step before it was scanned using a table-top scanner. The entire VFI test process was finished in less than 30 min.

1×PBS is from ThermoFisher. Bovine serum albumin (BSA), Triton X-100, PB buffer, boric acid, and sodium tetraborate is from Sigma Aldrich. All the chemicals used are of analytical grade and are applied without any further purification or modification.

Image processing and data analysis: After the drying process, the VFI membrane 3 was scanned with a consumer-grade table-top scanner (CanonScan 9000F II) and Scan IJ Utility (default software for the CanonScan), with 48 bits RGB settings and 2400-dpi resolution exported into an uncompressed TIFF file format. The 48 bits RGB image was then converted to 16 bits grayscale image using the built-in function rgb2gray of Matlab (Mathworks, MA, USA). The resulting image was imported into ImageJ, where the spots 79 were analysed using a microarray grid to extract the mean grayscale values from the spots 79 with subtracted local background. Data processing and analysis were performed using Excel 2016 (Microsoft, WA, USA).

VFI Reaction Scheme

Our initial in silico theoretical analyses indicates a porous membrane based immuno-sensor that incorporates membranes with smaller pore size and high sample flow speed provides better sensitivity than traditional LFI. The following experimental results verify the theoretical findings and characterize the effects of the membrane pore size and sample flow speed on the limit-of-detection (LOD) of the VFI with a B. pseudomallei assay.

Figure 3B:
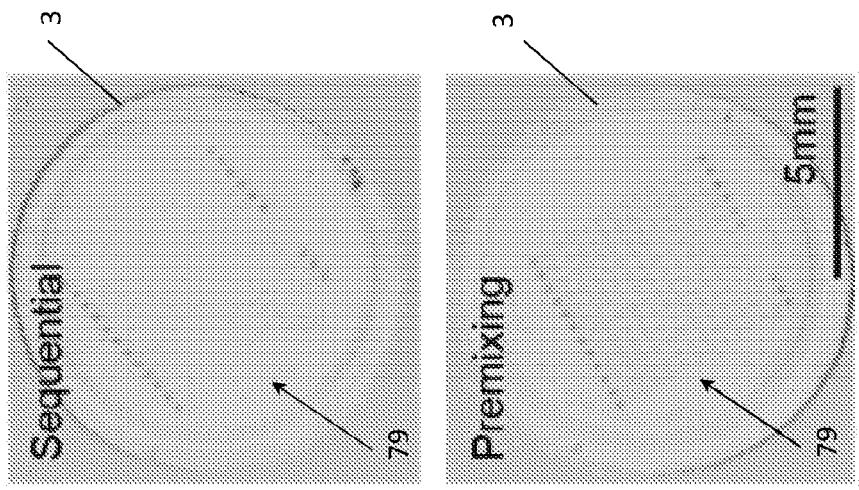
FIG. 3B are two membranes processed with the two different disclosed procedures of FIG. 3A.
Figure 3A:
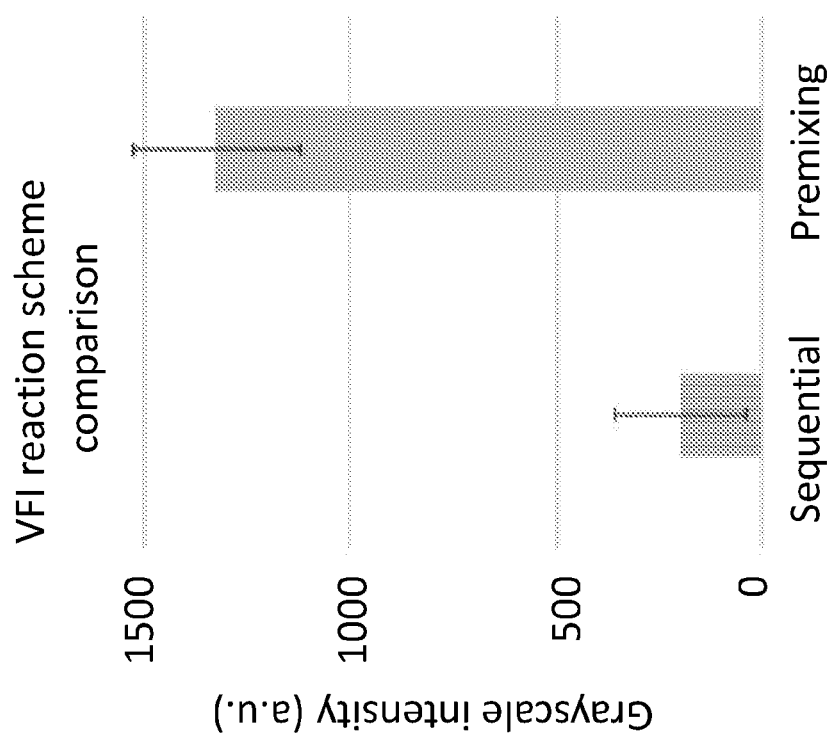
FIG. 3A is a plot comparing VFI sequential vs. premixing procedures. The grayscale intensity of the detection spots from the premixing procedure is 6.5 times higher than that of the sequential procedure.

Initially the experiments that are performed compared the two VFI reaction schemes, i.e. sequential and premixing. The sequential approach relied on the capture of CPS by the capture antibody agent 19 microarray of spots 79, followed by binding of the 4C4-GNP 12 to the captured CPS as the 4C4-GNP 12 solution was pushed by syringe 6 through the membrane 3. The premixing approach gave the antigen 13 (CPS) and detection antibody 10 particle (4C4-GNP 12) additional time for interaction and binding before being pushed through and captured by the capture antibody agent 19 microarray of spots 79. Both approaches used a 0.2 µm pore size nitrocellulose membrane 3, 1 ng/mL CPS spiked into 1 mL assay buffer solution, and a10 µL of the OD=9 (540 nm) 4C4-GNP 12. As shown in FIG. 3B, the premixing protocol yielded detection spots 79 (the centre array) with stronger signals than the sequential protocol. The relative intensity was increased by 6.5 times as shown in FIG. 3A. In the example, the improved sensitivity of the premixing approach is believed to be attributable to the increase in binding time between CPS and 4C4-GNP 12 and better efficiency of the liquid reaction when compared to the surface reaction. All subsequent experiments were performed using the premixing method.

Figure 4:
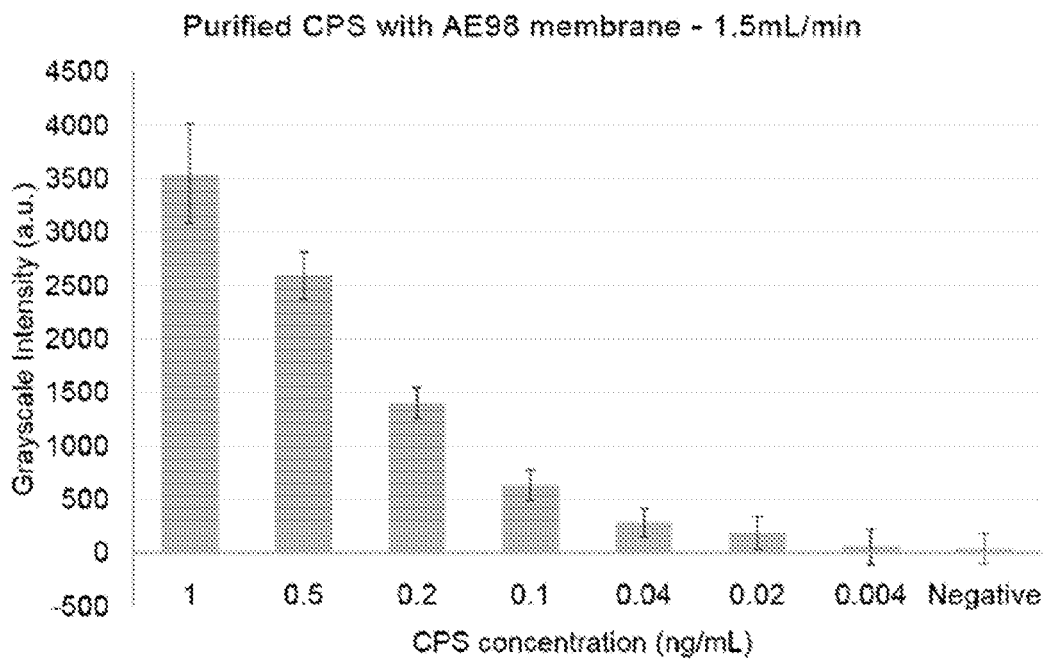
FIG. 4 is a plot of grayscale intensities for purified CPA with an AE98 membrane. CPS limit-of-detection (LOD) for a VFI device with 5 μm pore size nitrocellulose membrane (Whatman AE98) at a flow rate of 1.5 mL/min is determined to be about or slightly lower than 0.1 ng/mL.

VFI with membrane of 5 µm pore size: After selecting the reaction scheme, experiments were performed using a nitrocellulose membrane 3 of 5 µm pore size (Whatman AE98, GE Healthcare). This membrane 3 has a similar pore size to the nitrocellulose membrane 3 used in the CPS LFI protocol type (10 µm pore size, Whatman FF120 hp, GE Healthcare) but without the backing layer (Houghton et al., 2014). The premixed sample solution was pushed by syringe 6 through the membrane 3 at a volumetric flow 23 rate of 1.5 mL/min for 10 min, a flow 23 rate comparable to that of an LFI. Purified CPS was tested on the VFI to determine the LOD under this condition. Dilutions of CPS (1, 0.5, 0.2, 0.1, 0.04, 0.02, and 0.004 ng/mL) were prepared in the assay buffer and applied to the VFI membrane 3. 15 µL of the 4C4-GNP 12 solution was added to the sample and mixed for 10 min before the flow-through step. The LOD was defined as the concentration that generated a signal that was greater than 3 times the standard deviation (SD) above the background signal. As shown in FIG. 4, the LOD was determined to be at or slightly lower than 0.1 ng/mL.

Figure 5:
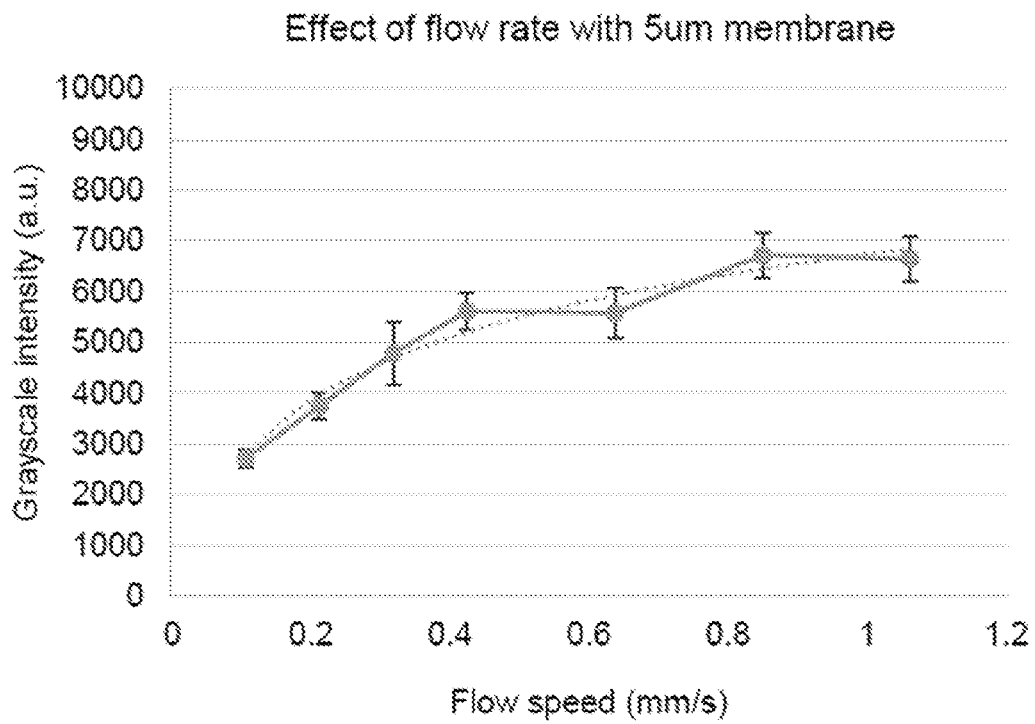
FIG. 5 is a plot showing the effect of the sample flow rate on the analytical signal with the 5 μm pore size nitrocellulose membrane (Whatman AE98). As the flow rate increases, signals from the detection and positive control spots improve.

Effect of flow speed for membrane of 5 µm pore size: Next, the effect of flow 23 speed on the sensitivity of the assay was studied. It was suspected that a faster flow 23 speed would deliver more antigen 13 to the membrane 3 sensor, which could improve the sensitivity. The VFI system was tested using 1 ng/mL CPS spiked in assay buffer with different flow 23 speeds using a constant assay time of 10 min with the AE98 membrane 3. The volume of the 4C4-GNP 12 stock solution added to the CPS sample was adjusted to keep the final concentration of GNP 12 constant. According to the results shown in FIG. 5, as the flow 23 speed (equals to volume flow 23 rate divided by the surface area 81 of the membrane 3) increased, signals from both the detection and positive control spots 79 were increased.

Figure 6:
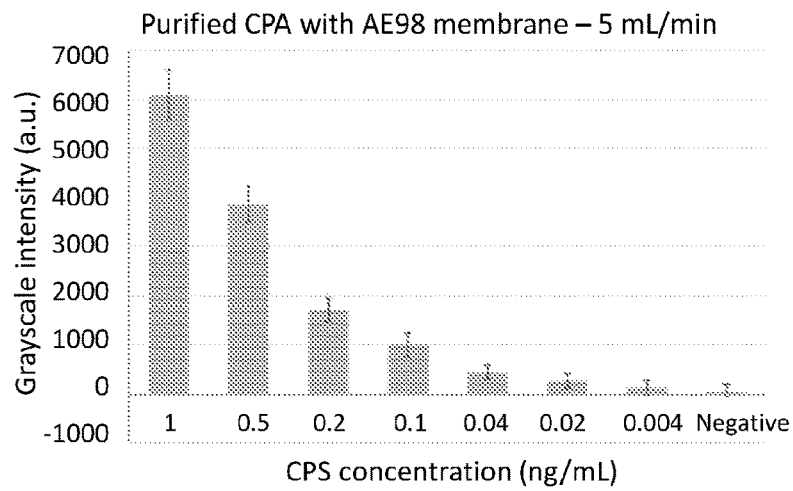
FIG. 6 is a plot of grayscale intensity by membrane pore size for determination of LOD of a VFI device with 5 μm pore size nitrocellulose membrane (Whatman AE98) at a flow rate of 5 mL/min.

Knowing that increasing the sample flow 23 speed could improve the sensitivity, the LOD of the VFI device 1 was tested again with a higher flow 23 rate of 5 mL/min. Dilutions of purified CPS (1, 0.5, 0.2, 0.1, 0.04, 0.02, and 0.004 ng/mL) were prepared in the assay buffer and applied to the VFI membrane 3. 50 µL 4C4-GNP 12 solution was added to the CPS sample and mixed for 10 min. As shown in FIG. 6, the LOD was determined to be at or slightly lower than 0.04 ng/mL.

Figure 7:
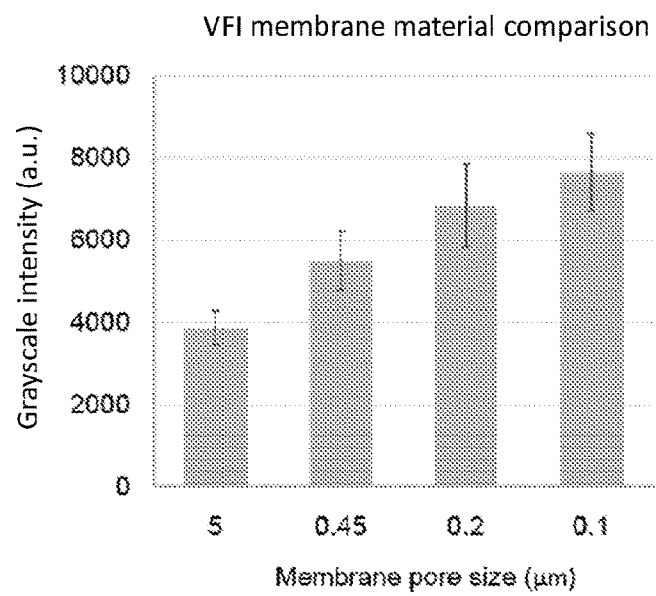
FIG. 7 is a plot of VFI membrane material comparison with the CPS assay. As the membrane pore size decreases, the signals are enhanced.

VFI membrane pore size effect: Four nitrocellulose membranes 3 with different pore sizes (0.1 µm, 0.2 µm, 0.45 µm, and 5 µm) were tested to determine the effect of membrane 3 pore size on the sensitivity of the CPS VFI. 0.1 µm is the smallest pore size of commercially available nitrocellulose membrane. One filter paper (Whatman qualitative filter paper, Grade 1, effective pore size 11 µm) was also tested, but failed in the capture antibody immobilization step. 1 ng/mL CPS spiked in assay buffer solution was used throughout as the testing sample. Samples were processed with a flow 23 rate of 1.5 mL/min and 10 min assay time. Results from using different nitrocellulose membranes 3 are shown in FIG. 7. A decrease in the pore size of the nitrocellulose membrane resulted in enhancement of the signals for the detection spots 79. The signal from the 0.1 µm membrane 3 was twice as strong as that observed for the 5 µm membrane 3.

Effect of flow speed for membrane of 0.1 µm pore size: In the example, the effect of flow 23 speed was tested using the 0.1 µm membrane, which showed the best signal among the different pore size membranes 3. Assay buffer solution spiked with 1 ng/mL CPS was pushed through the membrane 3 with flow 23 rates of 0.5, 1, 1.5, 2, 3, 4, 5 mL/min for a constant time of 10 min. According to the results shown in FIG. 8, increased signal intensity at higher flow 23 rate was observed. An increase in sensitivity with higher flow 23 rate was also observed with the 5 µm pore size membrane 3, but overall signal was stronger with the 0.1 µm pore membrane 3. There was no significant change in the background levels with the change in pore size of the membrane 3.

Figure 8:
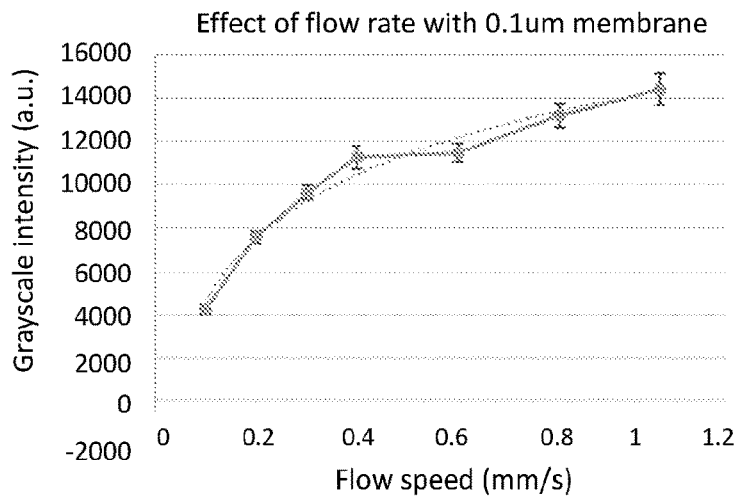
FIG. 8 shows the effect of the sample flow speed (e.g., sample flux through the membrane) on signal intensity with a 0.1 μm pore size membrane.
Figure 9A:
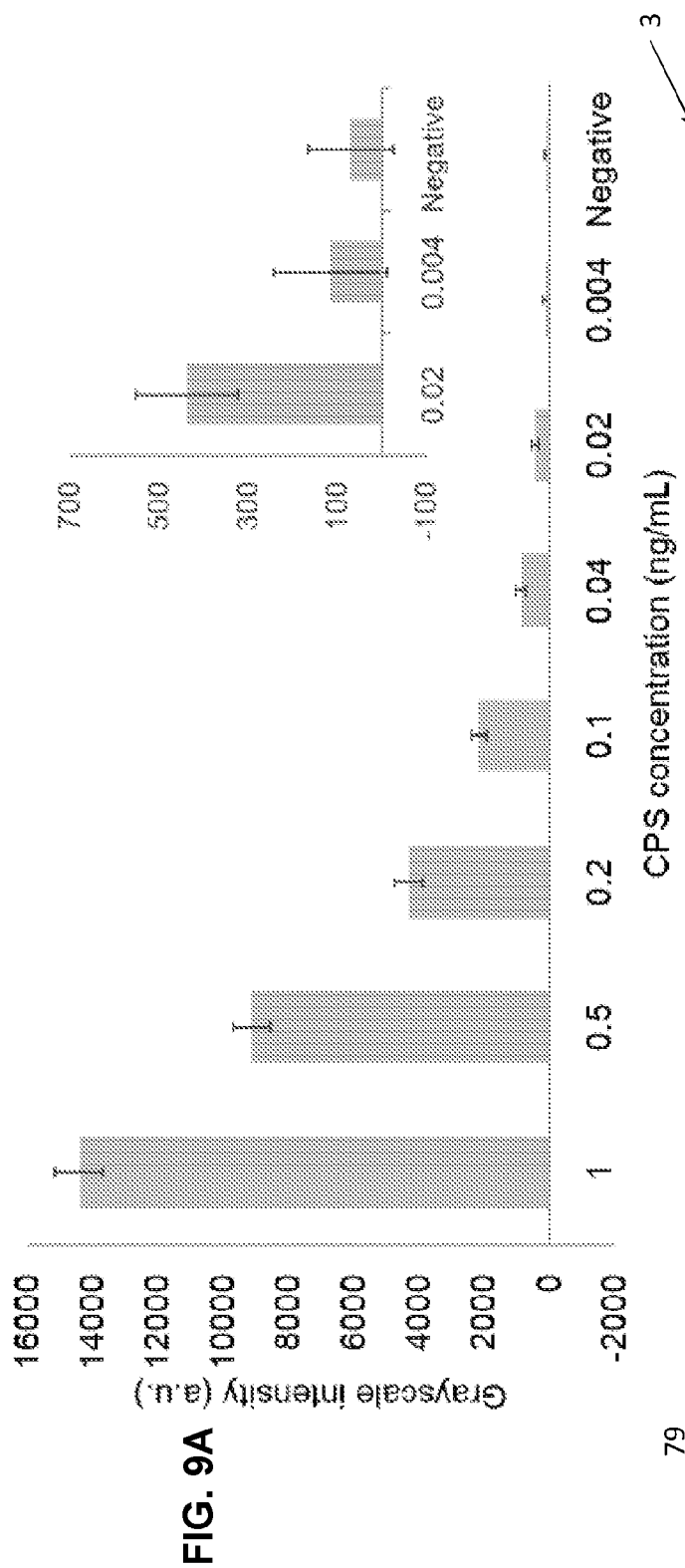
FIG. 9A is a plot for the determination of the LOD of the VFI with 0.1 μm pore size nitrocellulose membrane at the flow rate of 5 mL/min. Purified CPS is diluted in assay buffer, mixed with 4C4-GNP and applied to the VFI membrane. The LOD is determined to be at or lower than 0.02 ng/mL.
Figure 9B:
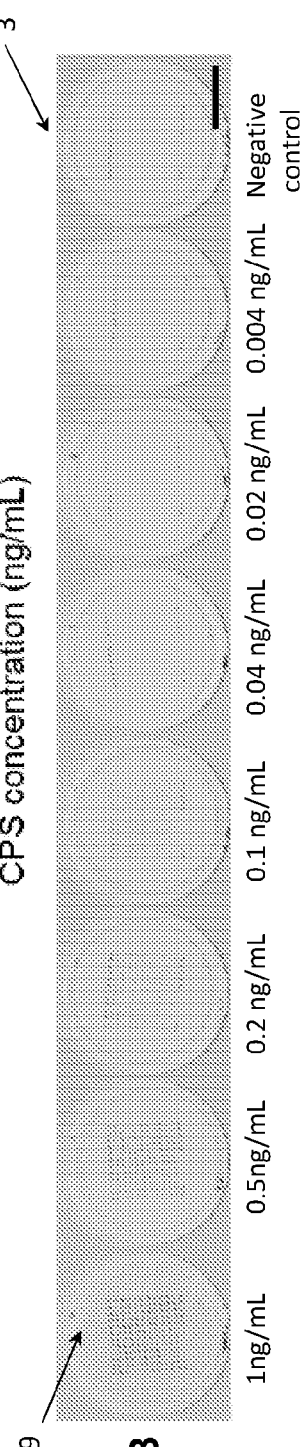
FIG. 9B shows scanned images of the membranes associated with the results of FIG. 9A.

LOD of optimized VFI system: The effects of the two critical factors, i.e. membrane pore size and sample flow speed, were proven individually through experiments with spiked samples and showed good agreement with the theoretical model. Using the knowledge gained from the flow 23 rate and membrane 3 pore size studies, the best performing flow 23 rate and membrane 3 conditions were integrated to determine the LOD of the VFI device 1 at optimal conditions, i.e., smallest membrane 3 pore size and highest flow 23 rate. The 0.1 µm pore size membrane 3 was selected and applied the sample at the highest flow 23 rate of 5 mL/min. Dilutions of purified CPS (1, 0.5, 0.2, 0.1, 0.04, 0.02, and 0.004 ng/mL) were prepared in the assay buffer and mixed with 50 µL 4C4-GNP 12 solution for 10 min and then passed through the VFI membrane 3 using syringe 6. The scanned images of the membranes 3 are shown in FIG. 8, together with the signals extracted from each membrane 3. The LOD was determined to be at or slightly lower than 0.02 ng/mL.

VFI for multiplexing detection of bio-threat pathogens—proof of concept: With the ability to accommodate a microarray of spots 79 utilizing different capture antibody agents 19, VFI is inherently suitable for multiplex biomarker detection. For biothreat detection, a proof-of-concept experiment was performed using the VFI device 1 platform to detect two targets simultaneously—CPS and PGA (a biomarker for the bacterium *Bacillus anthracis*, which is the causative agent of anthrax) (Gao et al., 2015). The design of the multiplexing VFI membrane 3 is shown in FIG. 10A. The detection microarray was divided into two parts. Half was coated with mAb 4C4 targeting CPS, and the other half was coated with mAb 8B10 targeting PGA. Goat anti-mouse IgM+IgG+IgA and 1×PBS were also dispensed onto the same membrane 3 as a positive and negative control. Four samples with different antigen 13 contents (CPS negative/PGA negative, 1 ng/mL CPS/PGA negative, CPS negative/1 ng/mL PGA, and 1 ng/mL CPS/1 ng/mL PGA) were processed with the VFI membrane 3 of 0.1 µm pore size at a flow rate of 1 mL/min and 10 min assay time. FIG. 10B shows the scanned images of the four membranes 3. FIG. 10C shows the signal intensities from the four membranes 3. Detection spots 79 showed positive signals only when the corresponding antigen 13 was present in the sample. This experiment demonstrated that the VFI device 1 platform was able to detect multiple biothreat agents simultaneously. Unlike LFI, the detection spots 79 were spatially separate and reactions were independent from each other in the VFI device 1, making the VFI especially suitable for large-scale multiplexing detection. However, there is still chance for cross-reactivity or non-specific binding to occur (Juncker et al., 2014), which may require further characterization of the premixing condition and buffer solution. This experiment demonstrates that the VFI platform was able to detect multiple bio-threat agents simultaneously. Unlike LFI, the detection spots are spatially separate and reactions are independent from each other in the VFI system, making the VFI devices provided herein especially suitable for larger-scale multiplexing detection.

Figure 11C:
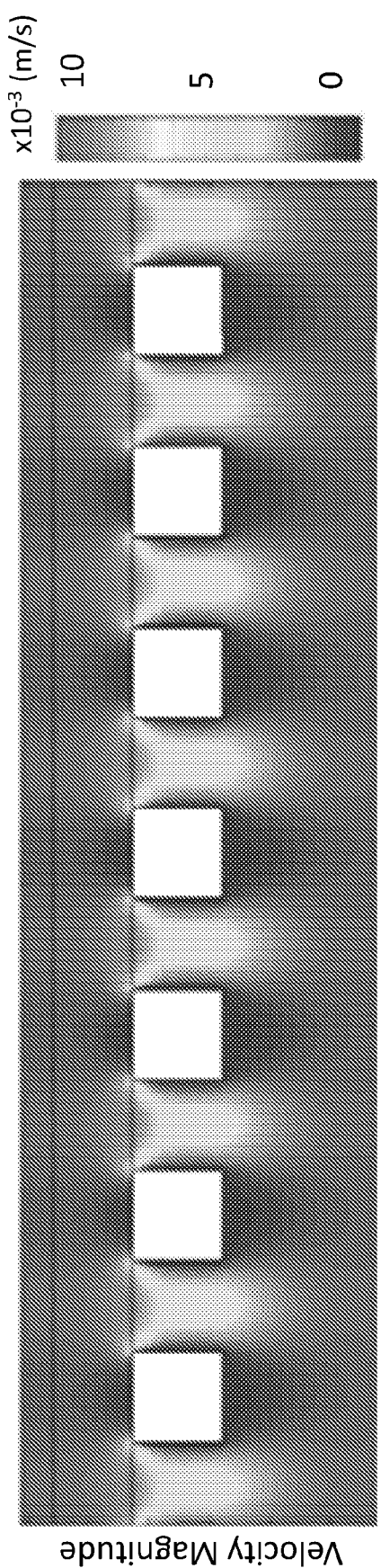
Figure 11D:
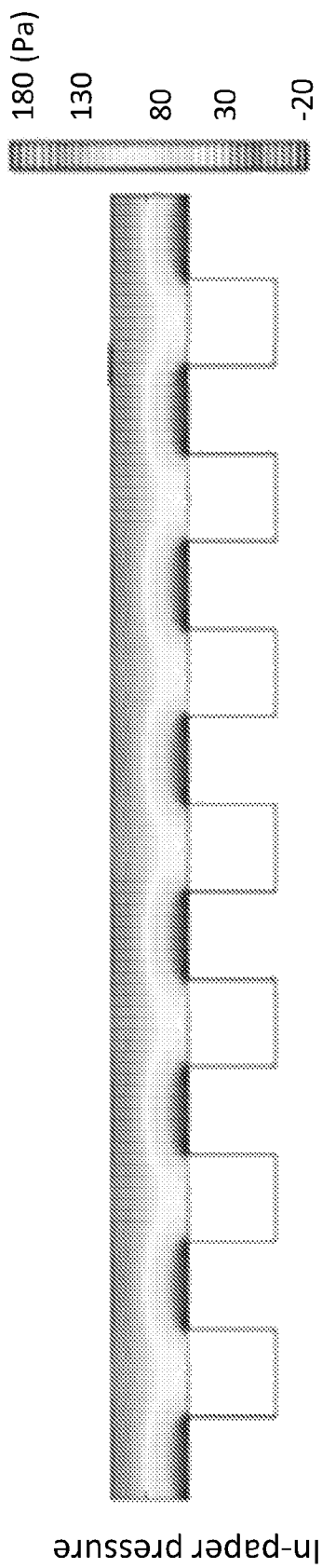
Figure 11E:
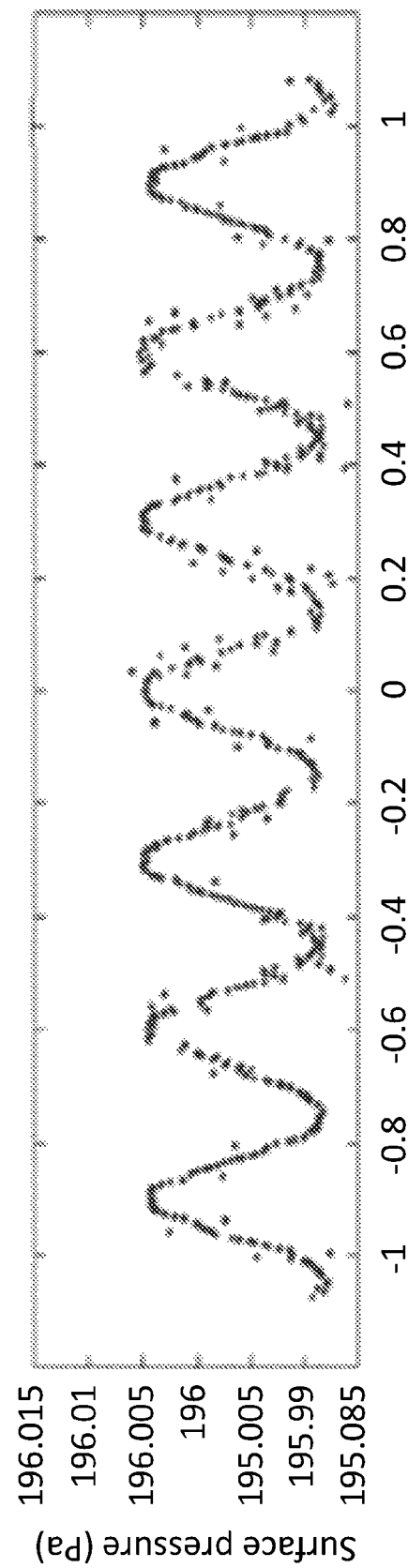

VFI fluidic simulation: To investigate the flow uniformity across the membrane 3, fluid simulation was performed using FEM software COMSOL Multiphysics 5.0 (CONSOL, Inc., Los Angeles, CA, USA). The simulation was started with the stainless steel holder 29 chamber, without any paper membrane 3 or Si grid support 21. Due to the nature of the fluid dynamics, the velocity was significantly higher in the central part of the holder 29 chamber, as shown in FIG. 11A. Upon implementation of the support 21 (modelled as non-deformable solid structure with multiple openings) and the paper membrane 3 (modelled as a porous thin film) into the model, the liquid flow profile was changed significantly. As shown in FIG. 11B, the support 21 and the membrane 3 evened out the fluid flow 23 across the flow chamber. FIG. 11C shows a zoom-in view of the flow 23 magnitude profile across the membrane 3. The velocity is higher on top of the hollow part of the Si grid support 21 than that on top of the solid part. This variation of velocity translates into the variation of pressure with the paper membrane 3, as shown in FIGS. 11D and 11E. However, the pressure on the top surface 5 of the paper membrane 3, which is the most critical part as the imaging plane, the pressure variance is within 1%. Therefore, the flow 23 and pressure across the membrane 3 can be considered uniform.

DISCUSSION: In this example, the detection of biothreat pathogens is based on a sandwich immunoassay that has been integrated into a nano-porous nitrocellulose membrane 3, which generates colorimetric signals as readout. The VFI device 1 technology provides a simple, miniaturized, and rapid (sample-to-answer time under 30 min) platform for bio-threat pathogen detection.

When testing the effect of the flow rate in a flow-through device 1, a common experimentation scheme is to keep the sample volume constant and change the flow rate (Zimmermann et al., 2005). This is effective in pursuing an assay with high processing speed with limited sample volume. However, in real world applications, especially when dealing with abundant sample such as urine or environment water, sample volume is no longer a constraint. Therefore the experiments in this example were performed with a constant assay time of 10 min and varied the flow 23 rate, and equivalently the sample volume, to compare the VFI's detection sensitivity. The 10 min assay time was selected to match the time needed for a LFI test. The effect of flow 23 speed was tested with two types of membrane 3 (with pore size of 5 µm and 0.1 µm). In both cases, the signals from the detection spots 79 were enhanced as the flow 23 rate increased. The porous structures 23 of the membrane 3 were modelled as bundled nanotubes, and this relation between flow 23 speed and signal intensity can be explained with the classical model for flow through surface immunosensors (Squires et al., 2008). As the flow 23 rate increased, the thickness of the depletion zone, in which the target antigen 13 can be captured by the surface antibody capture agent 19, was reduced. However, the increased flow 23 rate also delivered more samples to the membrane 3, which counterbalanced the loss of binding due to the reduced depletion zone thickness.

Due to the design of the disclosed VFI device 1, only the sample that was pushed through the regions with immobilized capture antibody agent 1 could be detected. The rest of the sample that went through the other regions was wasted. Therefore, it was the sample volume per unit area rather than the total sample volume that determined the amount of sample being delivered to the detection region. The higher the sample volume per unit area, the larger the amount of target antigens 13 that could be captured by the capture antibody agent 19. Table 1 summarizes the key features of some previous immuno-filtration devices. The disclosed VsI device 1 has a much higher sample volume per unit area compared with previous work. As a result, the sensitivity of the VFI was improved.

TABLE 1

Key feature comparison between the presented VFI and previous reported immune filtration devices. Because of the high sample volume per unit area in the disclosed VFI device 1, a better sensitivity was achieved.

| Reference | Membrane size (mm²) | Sample volume (μL) | Sample volume per unit area (μL/mm²) | Sensitivity |
|---|---|---|---|---|
| VFI | 78.5 | 50000 | 636.94 | 0.02 ng/mL |
| (Hárendarčiková et al., 2017) | 70.85 | 2000 | 28.23 | NA |
| (Pauli et al., 2015) | 63.59 | 5000 | 78.63 | 1.0 ng/mL |
| (Berger et al., 2016) | 25 | 10 | 0.51 | 10 μg/mL |
| (Clarke et al., 2017) | 63.59 | 120 | 1.89 | 53.1 μg/mL |
| (Cretich et al., 2015) | 132.67 | 1500 | 11.31 | 0.42 ng/mL |
| (Chinnasamy et al., 2014) | 132.67 | 1000 | 7.54 | 1 ng/mL |
| (Oh et al., 2013) | 0.20 | 16 | 81.53 | 0.01 μg/mL |
| (Reutersward et al., 2015) | 132.67 | 10000 | 75.38 | 1.9 μg/mL |

The average CV across the membrane 3 was calculated to be 10%. It is comparable to previously developed system (Chinnasamy et al., 2014). Fluidic simulation was conducted to investigate the flow 23 profile inside the filter paper holder and confirmed the uniformity across membrane 3, as shown in FIG. 11. Notably, any high CV values (CV>0.85) when using a Si support 21 were not observed, even with the larger-pore membranes 3, which was reported in previous literature (Chinnasamy et al., 2014). It is possible that the Si grid support 21 that was fabricated in the example has a higher Young's modulus than the commercially available stainless steel grid. It was less susceptible to deformation, and thereby preventing inhomogeneous flow 23 from happening.

As predicted based on the theoretical model and later demonstrated through the experiments of the example, the advantage of VFI arises primarily from two factors—the samples volume per unit area and the membrane 3 pore size. Traditional LFI is relying on capillary force to transport the liquid through a long membrane (~40 mm), which posts limitations on the membrane 3 pore size. A common range of the LFI membrane pore size is 3~12 μm (Posthuma-Trumpie et al., 2009). However, VFI has a short membrane 3 flow 23 path (~130 μm) that allows for membranes 3 with submicron pore size to be used. Smaller pore size offers a higher protein loading capacity that creates more binding-sites inside the porous structures 11. The smaller pore size also reduces the required diffusion distance for an antigen 13 to be captured by the antibody capture agent 19 on the membrane surface. It has been shown that reducing the membrane pore size in the LFI system can also be an effective way to increase the assay sensitivity (Henderson and Stewart, 2002). Based on these reasons, the nitrocellulose membrane 3 with 0.1 μm pore size was selected in the example as the optimized substrate for the CPS assay. However, 0.2 μm and 0.45 μm options remain open for applications where the target antigen 13 is bigger than CPS.

One of the major hurdles preventing getting even better sensitivity was the low 4C4-GNP 12 concentration. The current VFI requires a large total sample volume to achieve high sample volume per unit area. Using a large sample volume in turn would require a sizable amount of labelled nanoparticles 12 to increase the binding efficiency. To solve this problem, one potential solution is to reduce the total volume of the sample while maintaining the high sample volume per unit. One approach to this would be developing a miniaturized VFI device 1 with smaller surface area 81.

This example describes the development and optimization of a prototype of the disclosed paper-based Vertical Flow Immunoassay (VFI) device 1 for the rapid diagnosis of bio-threat pathogens. *Burkholderia pseudomallei*, the causative agent of melioidosis, was used as a model bacterium target and a sandwich assay was developed to detect the capsular polysaccharide (CPS) as the diagnostic biomarker. The VFI device 1 incorporates at least 120 detection spots 79 that can potentially be distinct from each other, an assay time of less than 30 min, and gold nanoparticle 12 mediated colorimetric readout that is amendable to regular table-top scanner. The effects of sample flow 23 rate and membrane 3 pore size on the performance of the disclosed VFI device 1 were investigated. The results of the example agreed well with the theoretical analysis showing that high flow 23 speed through a nanopore membrane 3 was the key to achieving higher sensitivity. A deep-etched silicon grid support 21 was used instead of the commercial stainless steel support, which helped prevent large signal variation with membranes 3 of larger pore size. Two reaction schemes were compared—the premixing method where the sample and antibody-labelled nanoparticle 12 were mixed in advance proved to be more effective. A limit-of-detection (LOD) of 0.02 ng/mL was demonstrated with purified CPS. The multiplexing biothreat detection with CPS and PGA using the VFI device 1 platform was also demonstrated. The disclosed VFI device 1 offers a valuable approach to detect and reduce the bio-threat agents in a variety of resource-limited or clinical conditions.

See, e.g., Chen et al. "Paper-based Vertical Flow Immunoassay (VFI) for detection of bio-threat pathogens" Talanta 191(1): 81-88 (January 2019—available online Aug. 17, 2018) and supporting supplementary materials, all of which is hereby incorporated by reference.

Example 2: Design Rules for Vertical Paper-Based Immuno-Diagnostic System (VPI-DS)

This example addresses uniformity and PGA array printing, Purified and conjugated mAb for PGA, and development of mAbs for LPS, LcrV and F1, determine the effect of pH and ionic strength by LFI and tests of LcrV and F1 LFI. VPI assay using the disclosed device 1 was also evaluated for CPS and automatic image analysis software.

Figures 12A, 12B, 12C:
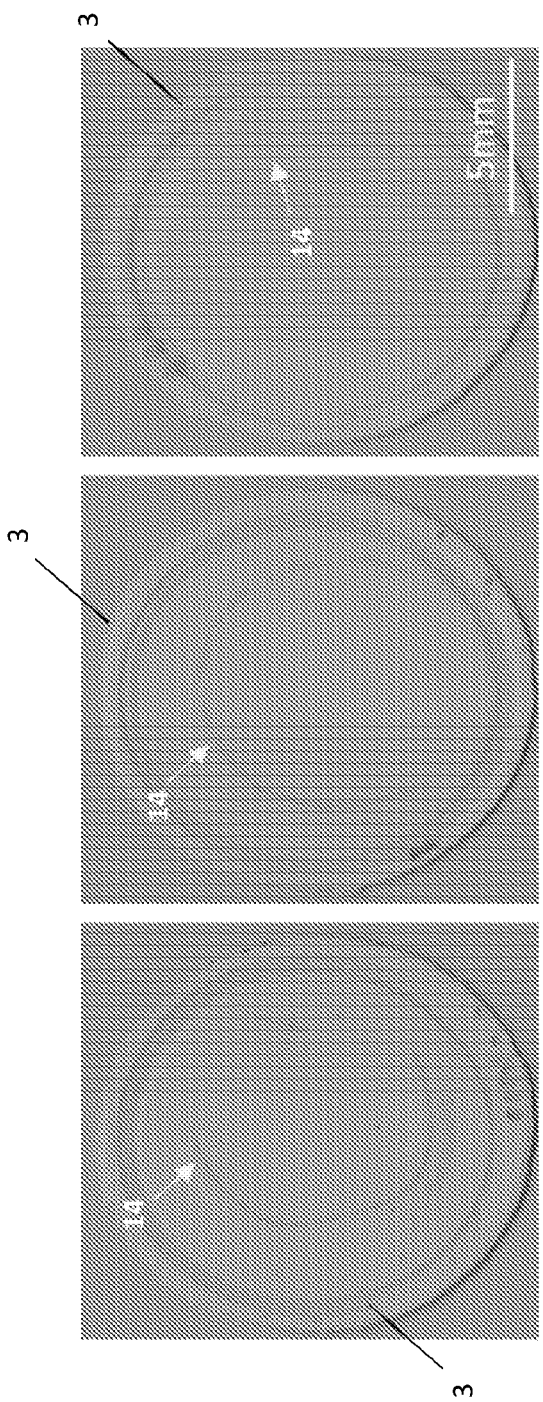
FIGS. 12A-12C are images of membranes exhibiting staining issues due to wrinkling issues.

TSignal variation across membranes: Several approaches were taken to solve the issue of the nitrocellulose membrane 3 wrinkle after the screening experiment. FIGS. 12A-12C depict images of membranes 3 exhibiting these issues to varying extents.

Issue: In most of the processed samples, a dark circular stain 14 can be seen on the nitrocellulose membrane 3 after the screening experiment. It is due to the wrinkle of the membrane 3 after liquid runs through, and the wrinkle generates uneven paper surface, which then imaged as the dark stain 14. The stain 14 is problematic because it might change the gray-scale intensity of the detection spots 79 and the background and lead to false detection results.

Figures 13A, 13B, 13C:
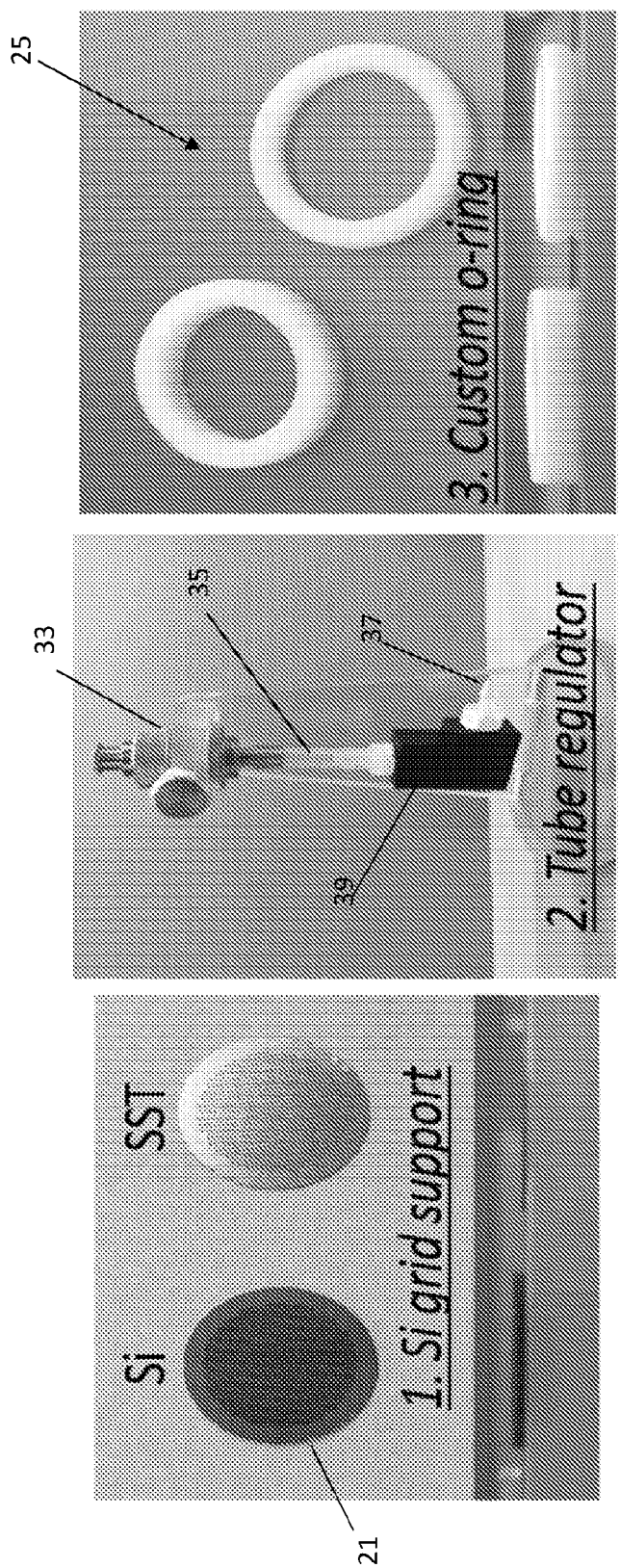
FIGS. 13A-13C are images of approaches taken to address the membrane staining and wrinkle issues.

FIGS. 13A-13C depict several failed approaches to solve this issue, including: 1) Use the Si grid support 21 instead of the stainless steel grid as the membrane 3 support. We tried to take advantage of the high stiffness of Si to maintain the shape of the membrane 3 better (FIG. 13A). 2) Tube regulator 33. We elongated the vertical tubing 35 connected to the outlet 37 of the screening chamber 39 to guarantee the liquid runs through the membrane 3 vertically (FIG. 13B). 3)

Customized O-ring 77. We fabricated our own o-ring 77 with a flat surface to apply more uniform force on the membrane 3 (FIG. 13C).

Figure 14:
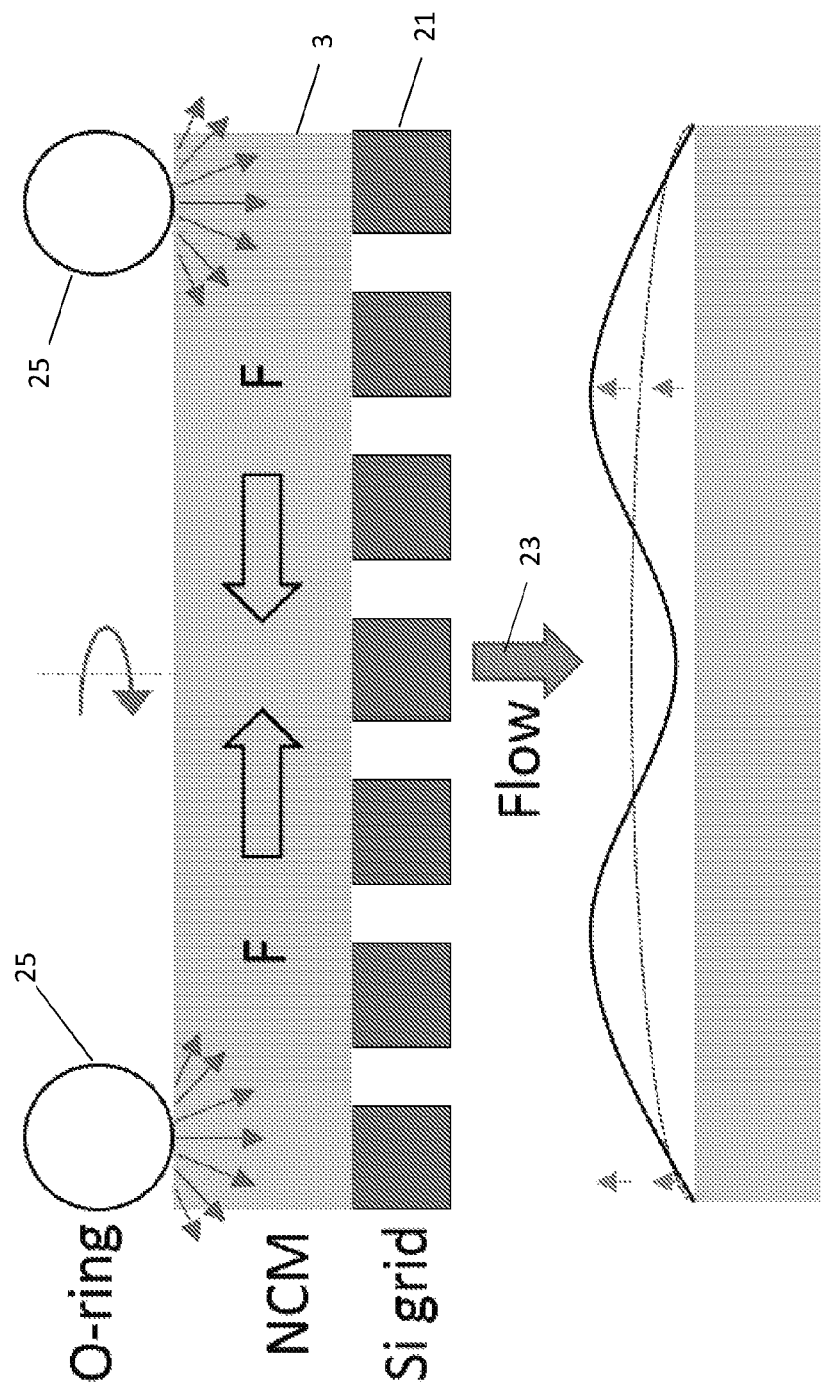
FIG. 14 is a schematic diagram illustrating the proposed reasoning behind the wrinkle of the membrane.

FIG. 14 is a schematic diagram illustrating the proposed reasoning behind the wrinkle: As we assemble the screening chamber 39, the force (clamping and twisting force) applied on the membrane 3 is higher at the edge of the membrane 3, which forms the membrane 3 into a dome shape. As the liquid runs through, higher pressure is applied at the center, and thus generates the wrinkle.

Figure 15B:
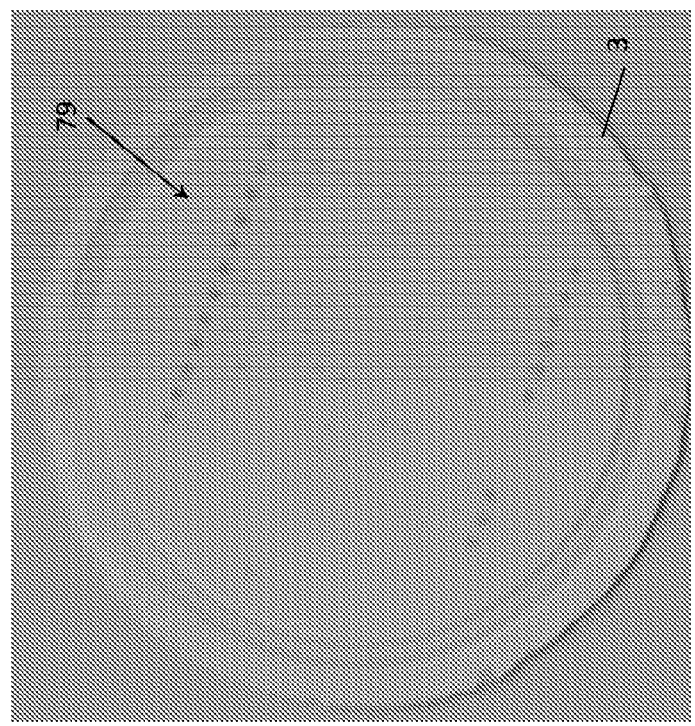
FIGS. 15A and 15B are images illustrating a solution to the membrane wrinkle and staining issue by pre-wetting the membrane with PBS before assembling the screening chamber.
Figure 15A:
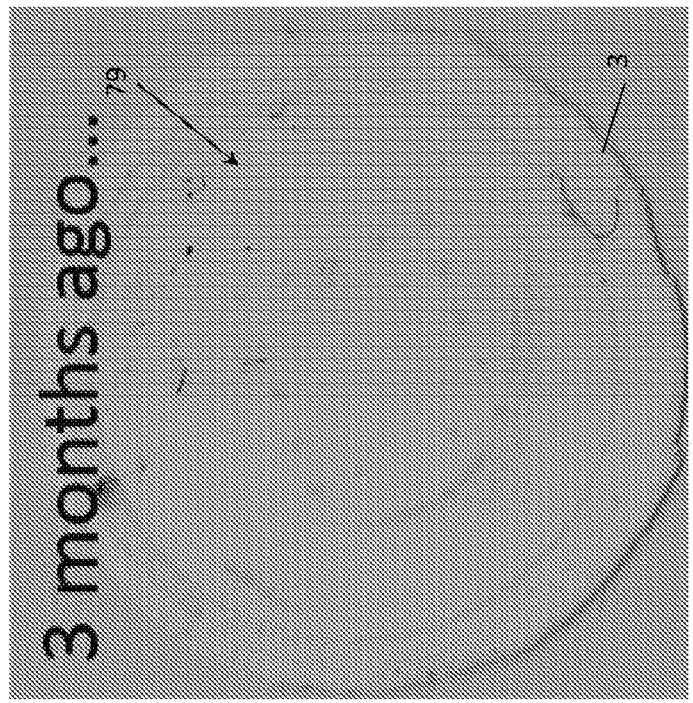

FIGS. 15A and 15B illustrate a solution to the membrane 3 wrinkle and staining issue. Final solution: pre-wet the membrane 3 with PBS even before assembling the screening chamber. So far, we have solved the problem with the air bubbles and the membrane 3 wrinkle. The quality is largely improved (as can be seen in the comparison of FIG. 15B to FIG. 15A).

Signal uniformity study: One of the concerns with the VFI is that the variation of the liquid flow 23 across the membrane 3 might introduce signal non-uniformity. We have presented in silico results of the pressure applied on the membrane 3, which appears to be consistent and relatively uniform across the membrane 3. Analysis is performed with some of the samples to study the signal uniformity.

We use the 10 min sample from the drying time experiment as an example. Even though variation can be seen among the many detection spots 79 in the array, no clear pattern can be observed as has been reported in previous publications. The variation appears random. With the current device 1, the signal variation is about 15%, which is a significant improvement compared to values reported in the literature. The dispensing process, which is mostly determined by the accuracy of the dispenser itself, has more than 10% variation according to the vendor specifications.

Figure 16B:
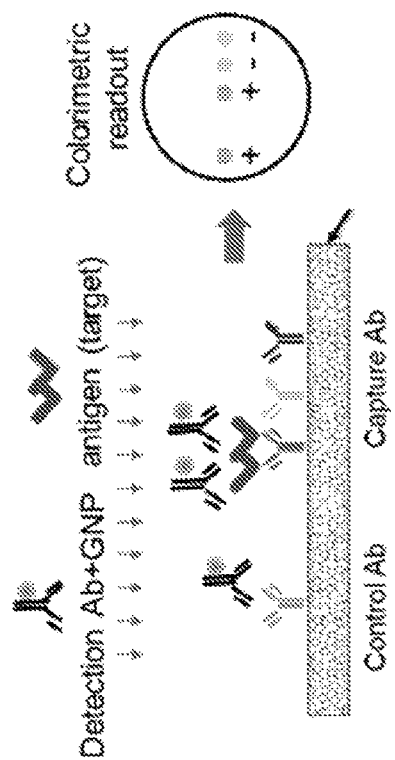
FIGS. 16A-16C is a schematic illustration of advantages of the vertical flow configuration for diagnostics, including of biological targets via antibody-antigen capture.
Figure 16C:
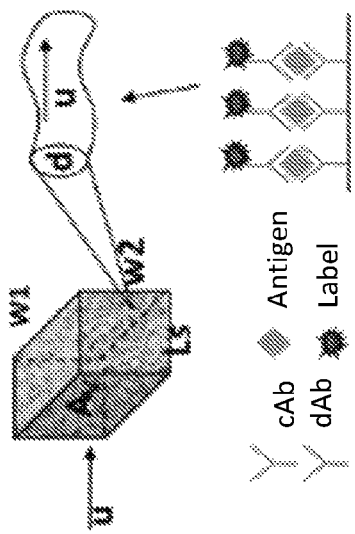
Figure 16A:
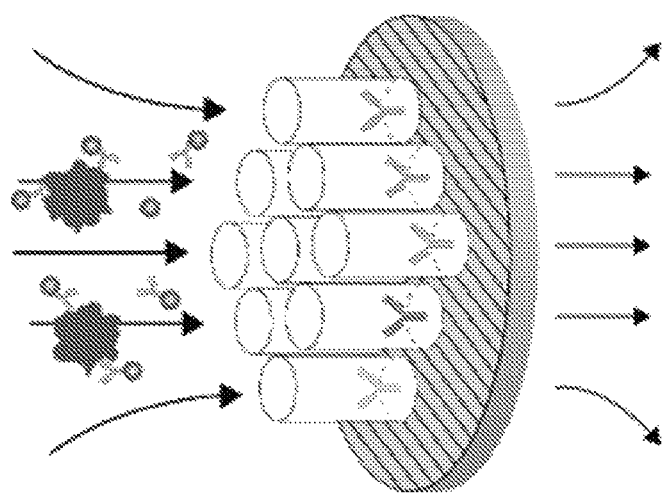

The systems and methods provided herein facilitate signal detection and sensitivity that is much improved over lateral flow systems. For example, FIG. 16A illustrates a membrane with different capture agents (e.g., antibodies in this example) on the surface, schematically modelled as hollow tubes to reflect the cross-sectional area of flow associated with each capture antibody. FIG. 16B is a close-up of a cross section, illustrating four different capture antibodies: one control and three different capture, with a corresponding colorimetric read-out. FIG. 16C illustrates a model based on flow speed (μ), sensing length ($L_s$), membrane pore size (d) and diffusivity (D). The diffusion time ($t_{dif}$) and resident time ($t_{res}$), are calculated as:

$$t_{dif}=d^2/(4D)$$

$$t_{res}=L_s/\mu$$

In this manner, the nanopores of the vertical flow systems (VFI) provided herein allows for better target capture under high flow speed. In addition, the VFI has a short flow path, on the order of 100 μm or less, compared to typically 40 mm or more in lateral flow systems (LFI).

Figure 17:
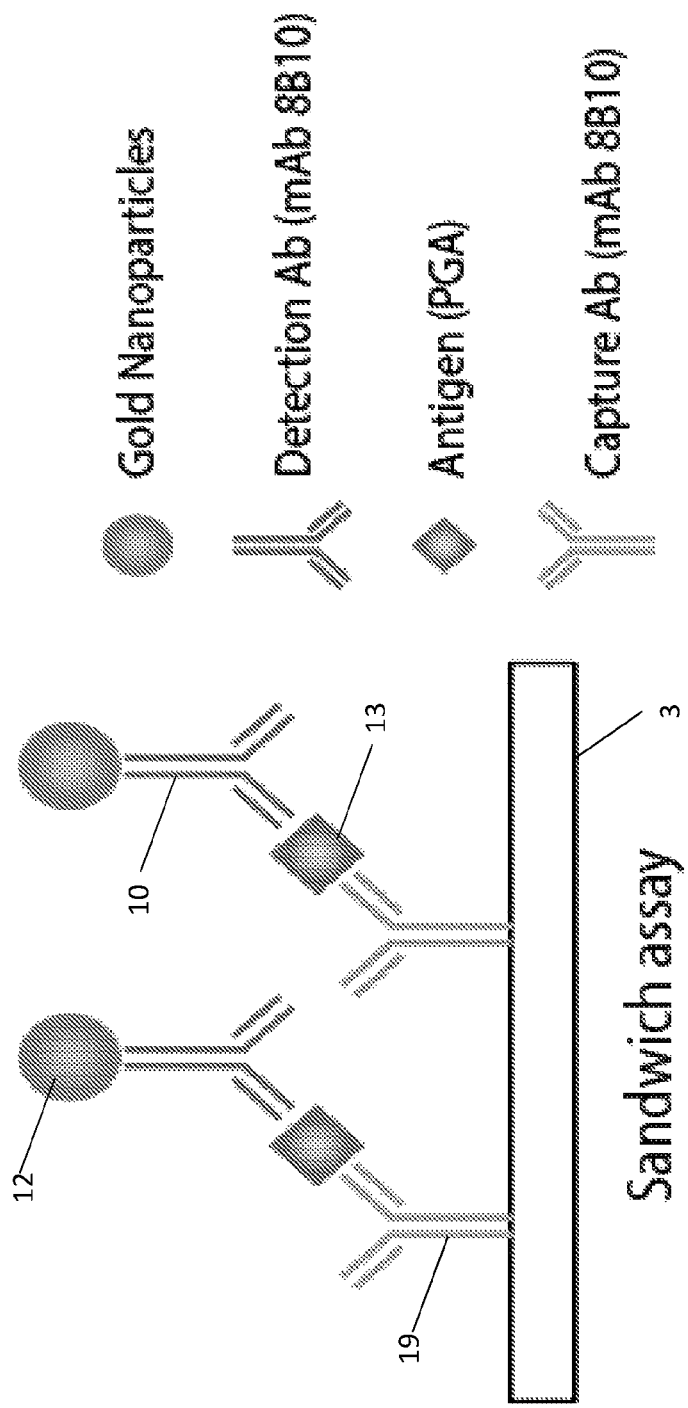
FIG. 17 is a schematic diagram of a sandwich assay.
Figure 18A:
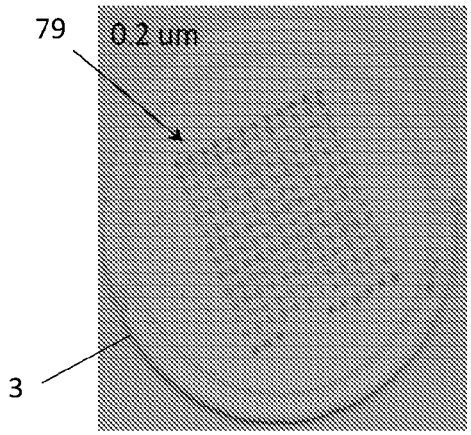
FIGS. 18A-18D depict membrane assay results for the assay set of FIG. 17.
Figure 18B:
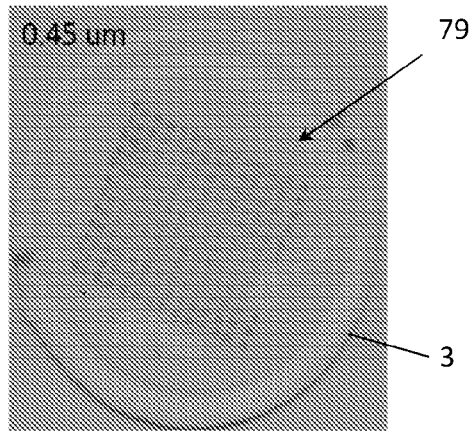

PGA assay dispensing and VFI testing: Other than the CPS assay, we started some of the early work with the PGA assay. The sandwich for the PGA is provided below. The capture antibody (8B10) agent 19 and detection antibody 10 (8B10-GNP) are used in this assay, as shown in FIG. 17. With the same recipe, we are able to dispense the 8B10 capture antibody (8B10) agent 19 onto the nitrocellulose membrane 3 using Biodot dispenser, as shown in FIGS. 18A and 18B.

Figure 18C:
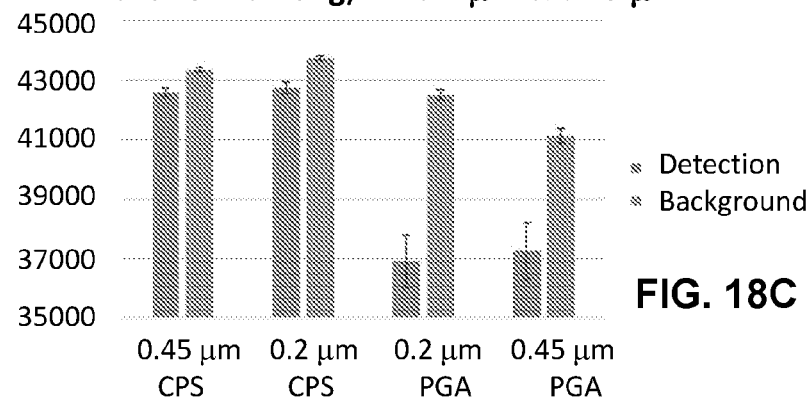
Figure 18D:
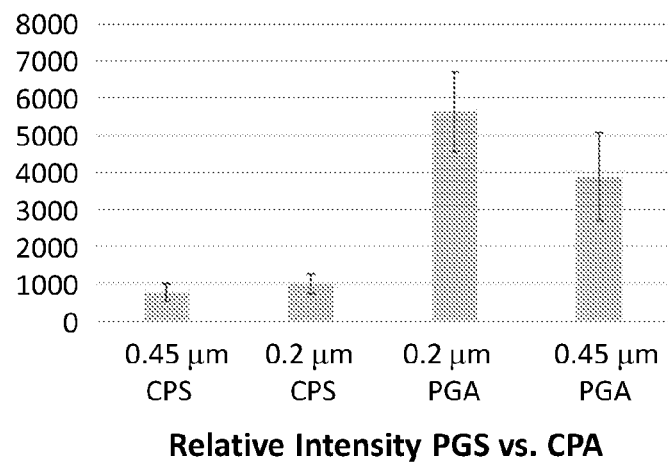

Conceptual experiments test the 8B10 sandwich assay at a concentration of 5 ng/mL. The results are shown in FIGS. 18C and 18D. The sandwich assay works on both the 0.2 μm and 0.45 μm membrane 3. The results of 5 ng/mL CPS and 5 ng/mL CPS are provided side by side, the PGA assay actually shows even stronger signal. We expect this assay to be more sensitive.

Development and purification of mAbs: Production and purification of Bacillus anthracis PGA mAbs: The B. anthracis poly gamma D-glutamic acid (PGA) specific mAb, 8B10, is purified using recombinant Protein A affinity chromatography. The purified mAb was also conjugated to 40 nm colloidal gold. Both the unlabeled and labeled mAb along with purified PGA are provided as part of the second antibody-antigen pair to be optimized in the vertical flow assay format.

Production and purification of Franciscella tularensis LPS mAbs: The hybridoma cell line producing the F. tularensis LPS reactive mAb, 1A4, is grown in tissue culture Integra flasks. One round of purification using recombinant Protein A affinity chromatography provides a yield of 40 mg of antibody. However, it has been found that the cell line is unstable under high-density Integra culture conditions. In response, a new set of mice are immunized with F. tularensis LPS in order to isolate a larger library of high affinity monoclonal antibodies to LPS. Serum titers from 6 weeks post-immunization indicated multiple mice have high levels of LPS specific antibodies. After additional boosting with Ft LPS, splenocytes is isolated for production of hybridomas.

Production, purification and characterization of Y. pestis LcrV and F1 mAbs: LcrV monoclonal antibodies: SPR analysis was performed on all eight purified LcrV monoclonal antibodies to determine mAb binding kinetics and affinity to purified recombinant LcrV (Table 2, below). The association rate constant (ka) and disassociation rate constant (kd) was determined for each mAb and used to calculate the equilibrium dissociation constant or "affinity" (KD=kd/ka). Alternatively, affinity was also calculated using a steady state equilibrium model (SSKD). A tenfold higher association rate (ka) was observed for mAb 8F10 when compared to all the other LcrV monoclonal antibodies. Monoclonal antibody 6F10 exhibited the slowest dissociation rate amongst the eight antibodies tested. Overall, mAb 8F10 performed the best in the SPR analysis and had the highest binding affinity.

LcrV mAbs were used in an antigen 13 capture ELISA format to determine the best antibody pairs for LFI production. All eight LcrV mAbs were HRP-conjugated and used to detect rLcrV, which was captured by unlabeled LcrV antibody in in an ELISA format. The limit of detection (LOD in ng/ml) for each antibody pair was calculated (Table 3, below).

F1 monoclonal antibodies: A library of twelve monoclonal antibodies F1 antibodies were generated and purified using recombinant Protein A affinity chromatography. Screening strategy for the 12 purified F1 mAbs was changed (from the LcrV strategy) to conserve purified antigens 13 and ELISA workload. All twelve F1 mAbs were gold labeled and wet tested in prototype LFIs and top eight mAb candidates were selected for further screening with SPR analysis and antigen 13 capture ELISAs. No significant differences in binding kinetics or affinity were observed between the F1 mAbs with the exception mAb 11C7, which had a ten-fold higher association rate when compared to the other antibodies (Table 4, below). All eight F1 mAbs were HRP-conjugated and tested in an antigen 13 capture ELISA format using recombinant F1. The limit of detection for each antibody pair was determined using a cutoff of 5 times the background level (Table 5).

Purification of biomarkers: Biomarkers (LPS, PGA, F1) are purchased commercially.

Effects of pH and ionic strength by LFI (CPS): Initial experiments comparing effects of pH and ionic conditions on mAb binding reactivity showed that a direct comparison could not be made between surface plasmon resonance (SPR) and lateral flow immunoassay (LFI) results. It was decided that this line of testing would proceed using only the LFI format, as this immunoassay format is most similar to the vertical flow assay being developed. In order to investigate the effect of ionic conditions on background and sensitivity of the 4C4 lateral flow immunoassay, LFIs were performed using phosphate buffered saline (pH 7.4) at different ionic strengths with or without surfactant P20. Significant background was observed at NaCl salt concentration below 100 mM (ionic concentration: 0.125 mol/L). Increase in salt concentration up to 300 mM (ionic concentration: 0.325 mol/L) did not produce any significant change in LFI performance (Table 1, below). These results indicate that using PBS with an ionic concentration above 0.325 mol/L might reduce false positive results in our LFIs. To complete the testing of ionic conditions, we plan to test 4C4 LFIs at higher ionic conditions and possibly test buffers that may be more compatible with the vertical flow assay format of the disclosed device 1.

Development of *Y. pestis* LcrV and F1 LFI prototypes: Since the majority of LcrV mAbs performed well in the antigen 13 capture ELISA, all LcrV mAbs were gold conjugated and sprayed as test lines onto nitrocellulose for evaluation as the detector and/or capture antibody in the LFI platform. Initial testing of all LcrV LFI prototypes has been completed and there are several promising candidates with a visual limit of detection between 1-10 ng/ml (FIG. 19).

Figure 20:
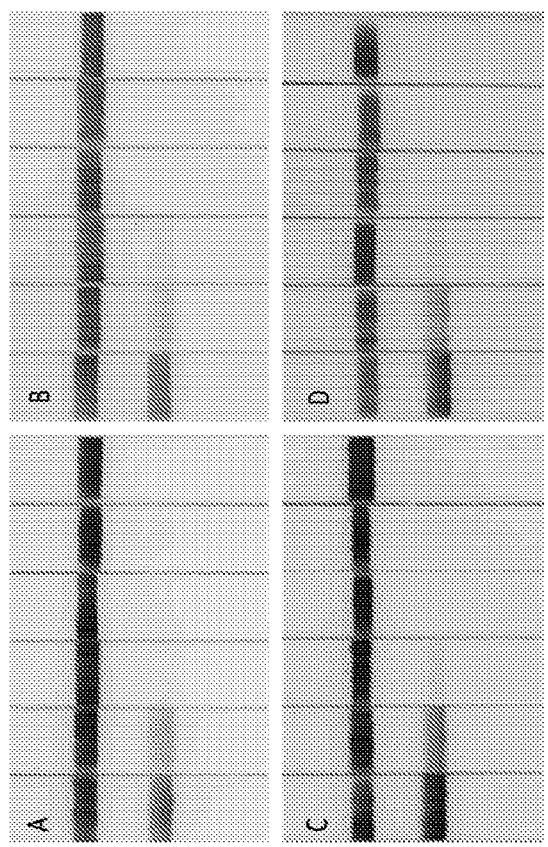
FIG. 20 depicts results of F1 antibodies testing in LFI format.

The eight F1 antibodies with highest reactivity in ELISA were selected for similar testing in LFI format (FIG. 20). Several prototypes have a visual limit of detection at 1-10 ng/ml with recombinant F1.

Initial testing was conducted using rLcrV or rF1 spiked into buffer. Current efforts are now focused on optimizing the LFI prototypes for use with human serum as the matrix.

Figure 19:
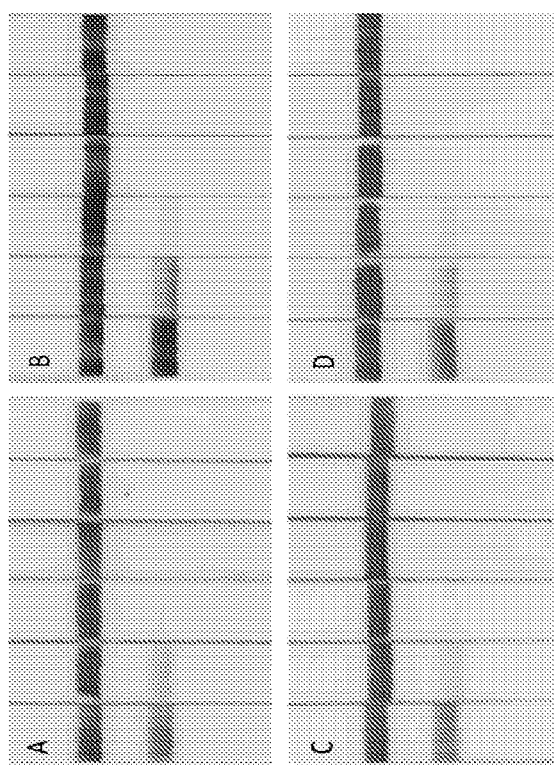
FIG. 19 depicts results of initial testing of LcrV LFI prototype testing.

As shown in FIG. 19, lateral flow immunoassays (LFIs) (A) 8F7:6F10, (B) 8F10:2B2, (C) 8F10:6E5, (D) 8F10:6F10 were tested with varying concentrations of rLcrV: from left to right: 1 ug/mL, 100 ng/mL, 10 ng/mL, 1 ng/mL, 500 pg/mL and negative control. Images were recorded after 20 min.

As shown in FIG. 20, lateral flow immunoassays (LFIs) (A) 4E5:3F2, (B) 10D9:3F2, (C) 11C7:3F2, (D) 11C7:15C4 were tested with varying concentrations of recombinant F1: from left to right: 1 ug/mL, 100 ng/mL, 10 ng/mL, 1 ng/mL, 500 pg/mL and negative control. Images were recorded after 20 min.

VPI CPS Optimization: Different parameters are tested individually first to get a working range. Then a DOE screening by DSD is conducted to select critical parameters, then a full factorial experiment will be done for the critical parameters for final optimization.

Figure 21:
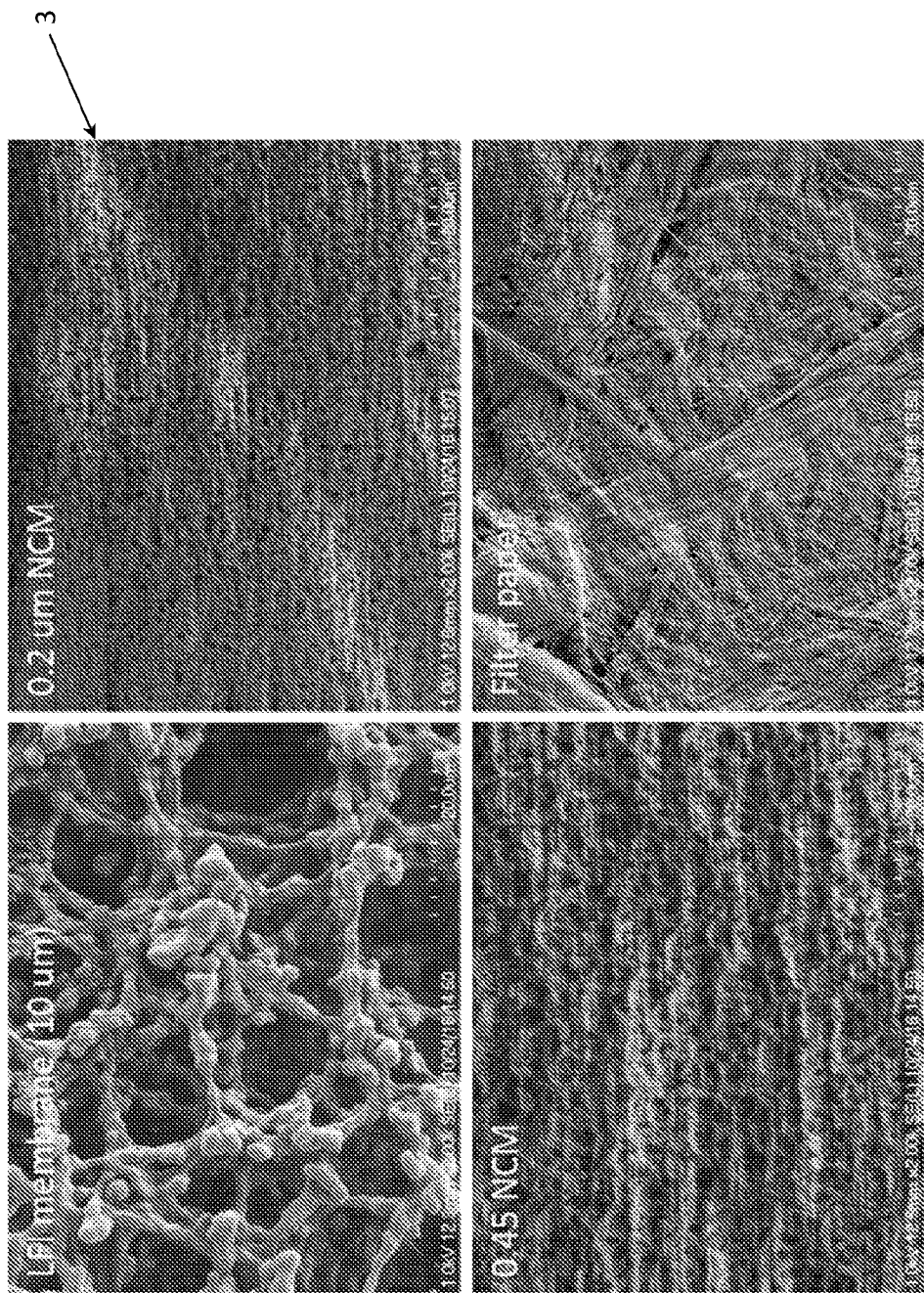
FIG. 21 shows examples of membranes used for material optimization and comparison.

Membrane material comparison and optimization: FIG. 21 shows examples of membranes 3 used for the optimization and comparison for this example. One of the advantages of the vertical flow 23 system in the disclosed device 1 is that the liquid transport does not rely on the porous structure 11 of the nitrocellulose membrane 3, which allows for membrane 3 materials with much smaller pore size. Such membranes 3 with small pore sizes have much higher loading capacity to bind more capture antibody agent 19. The diffusion range is also largely reduced to facilitate the antibody-antigen binding.

We first examined the two types of vertical flow nitrocellulose membranes 3 with 0.2 μm and 0.45 μm pore size, the typical lateral flow membrane (10 μm pore size), and the filter paper with SEM (the results with 2K magnification can be seen above). One can imagine that with such finer porous structure 11 the detection efficiency can be significantly improved.

We then tested six different materials in the VFI system of the disclosed device 1 with the CPS assay. The 8 μm and 12 μm nitrocellulose membranes 3 were selected to resemble the lateral flow membrane as they the closest provided by the same vendor.

| Material | NCM | NCM | NCM | NCM | NCM | Filter |
|---|---|---|---|---|---|---|
| Pore size (μm) | 0.1 | 0.2 | 0.45 | 8 | 12 | 11 |

Figure 22:
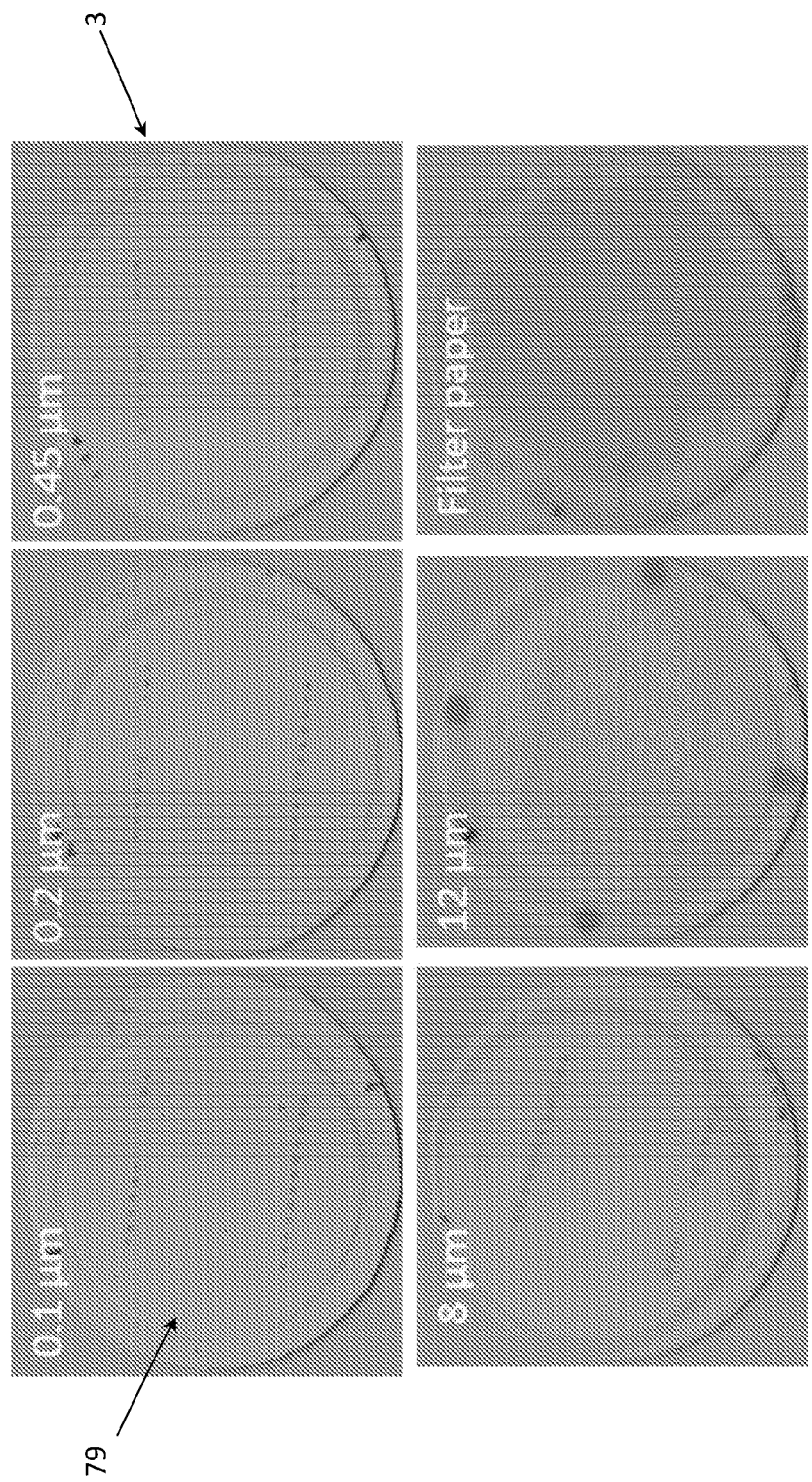
FIG. 22 contains images off testing for six different membrane materials in the VFI system with the CPS assay.

The results with 1 mL of CPS at the concentration of 5 ng/mL at the screening speed of 1 mL/min can be seen in FIG. 22. In all of the nitrocellulose membrane 3 samples, the positive control spots 79 (top and bottom rows of FIG. 22) can be clearly seen, and the detection spots 79 (the center array) have various intensities. However, on the filter paper, the dispensed microarray was smeared, and no signal can be observed from either the detections or the control spots.

Figure 23A:
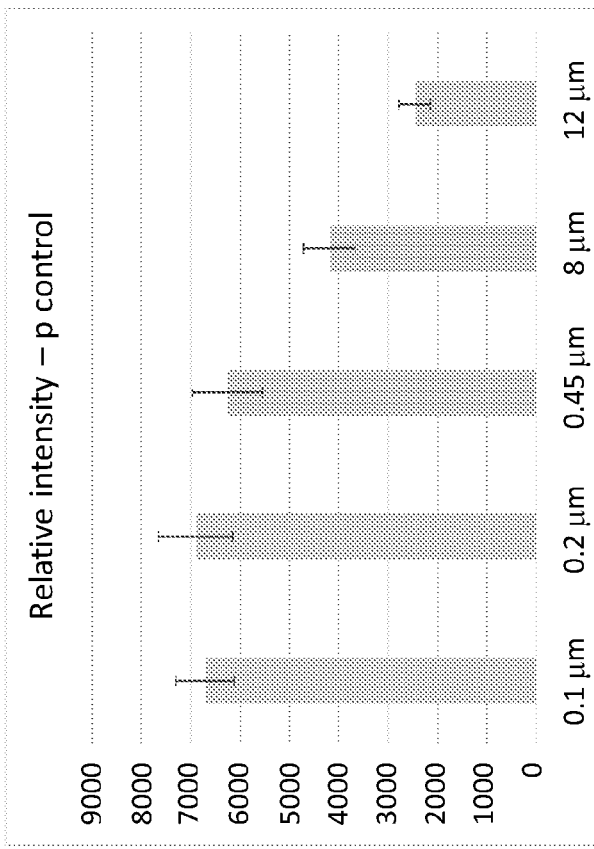
FIGS. 23A and 23B are plots of gray scale intensity for the assay of FIG. 22.
Figure 23B:
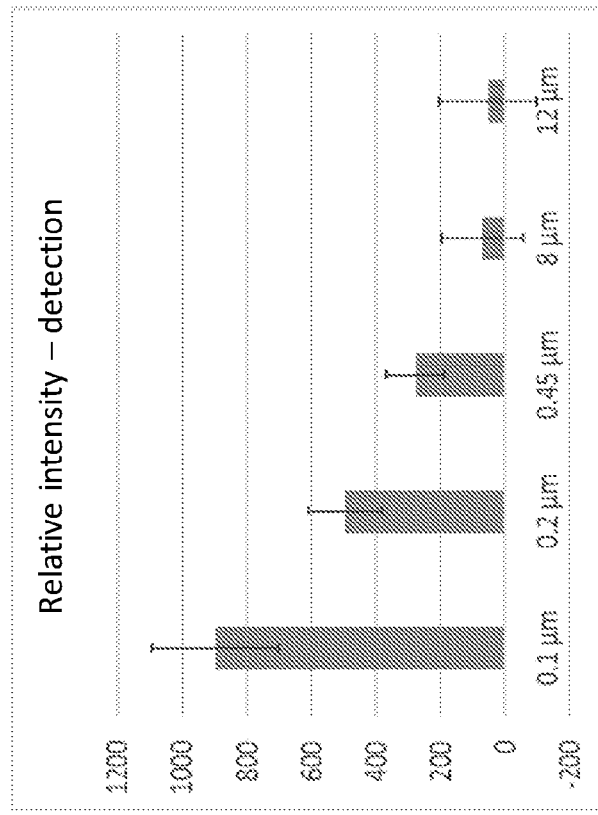

Now we look at the gray scale intensity we acquired from the images (FIGS. 23A and 23B). Please note that we are using 16 bit gray sclae scanning, so the range of the values should be between 1 to 65535. We can see that as the pore size goes smaller, the signals get enhanced. Especially for the detection spots 79, the signal from the 0.1 um membrane 3 is 16 times stronger than the 12 um membrane 3. The results strongly support our theory that by choosing a nitrocellulose material with much smaller pore size, the detection sensitivty can be significantly improved.

Drying time study: One of the many advantages of the VFI system of the disclosed device 1 is that it allows for processing of large volume of samples (mL level) which is impossible for lateral flow testing strip (L level) at high speed. However, it still requires a certain amount of drying time before scanning the membranes 3 for image analysis and signal extraction.

Figure 24:
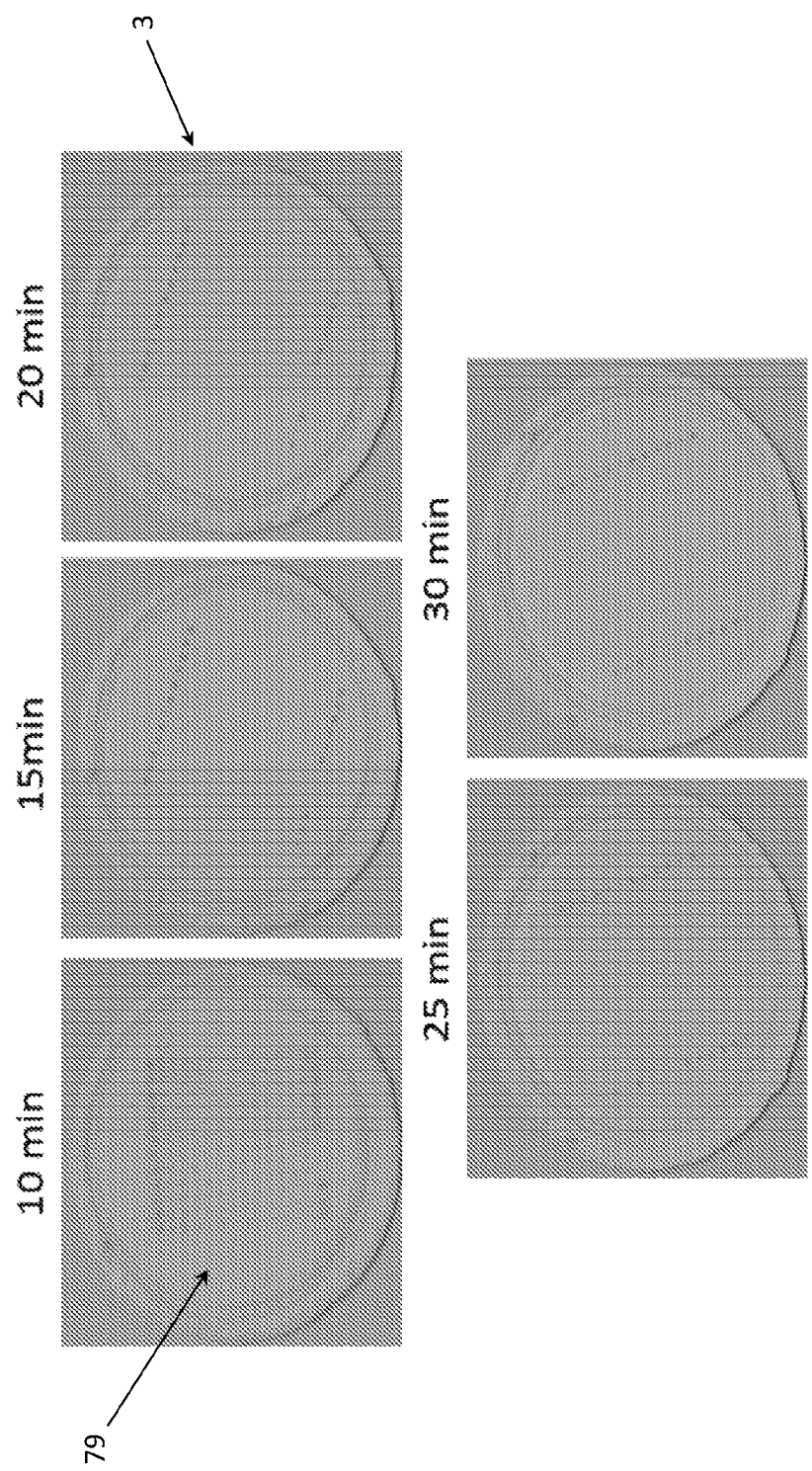
FIG. 24 contains images of a membrane drying time study for the assay of FIG. 22.

We studied the effect of the drying time (10-30 mins), which is the time between taking the membranes 3 out of the liquid and scanning the image. The scanned images are shown in FIG. 24.

Figure 25A:
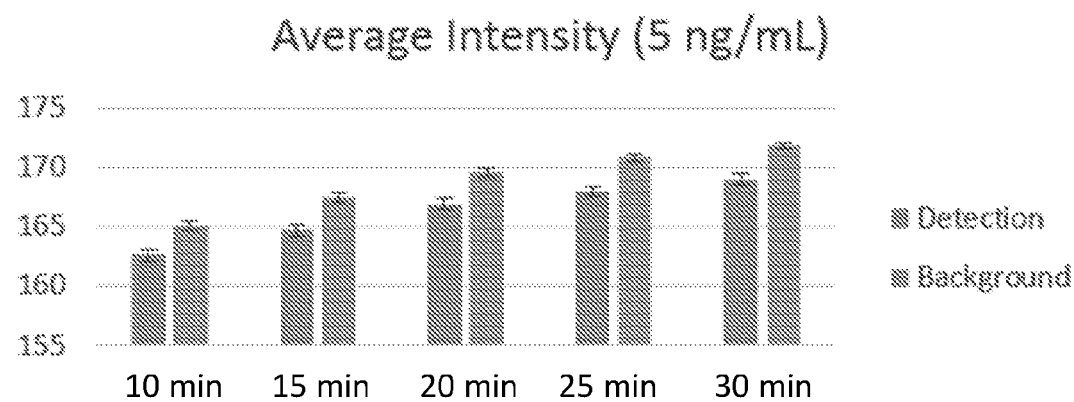
FIGS. 25A and 25B are plots of gray scale intensity for the drying time study of FIG. 24.
Figure 25B:
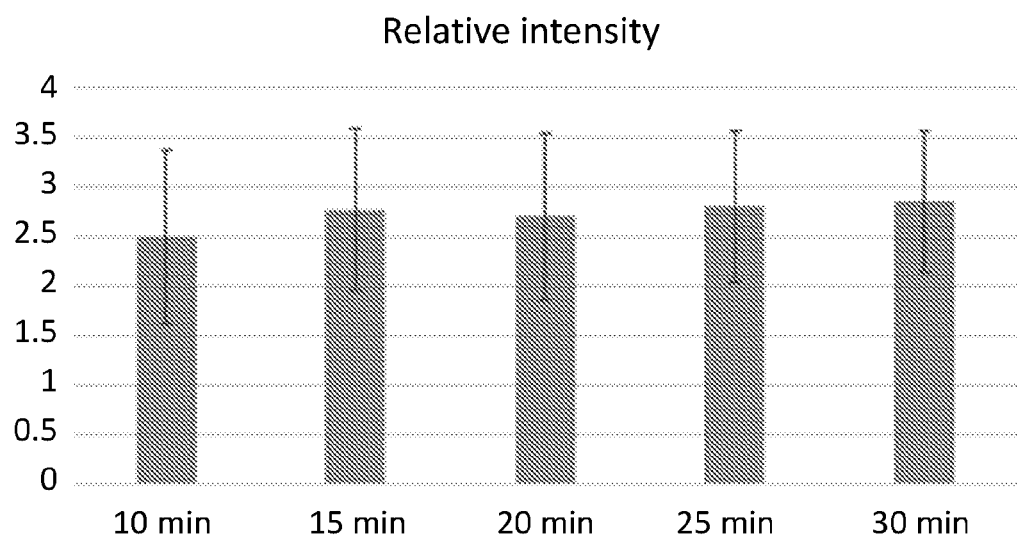

The gray scale intensity of the detection spots 79 can be seen in FIGS. 25A and 25B. As the drying time increases, the absolute intensity (raw intensity) of the detection spots 79 and background both go up. It can be explained that as the excessive water in the membrane 3 evaporates, the reflective index of the membrane 3 changes, and the membrane 3 appears lighter in color. In contrast, the relative intensity (detection spots 79 subtract the background) does not change much as the drying time goes up. Therefore, we can select the shortest drying time of 10 mins and keep the entire testing time as short as possible. Noted is that the drying time can be further reduced by using a drying pad 91 (FIG. 31A), or similar active drying mechanism.

Detection antibody 10 study: As an important part of the sandwich assay, the binding between the detection Ab 10 and the captured antigen 13 largely determines the intensity of the final signal. Since the CPS is a multivalent target, as the concentration of the detection Ab 10 increases, more nanoparticle 12 binds to the antigen 13. Hence the signal is enhanced. However, as it reaches and surpasses the saturation point, further increases of the detection Ab 10 concentration only increases the background. Therefore, it is important to characterize and find the optimum concentration of the detection antibody 10.

Figure 26:
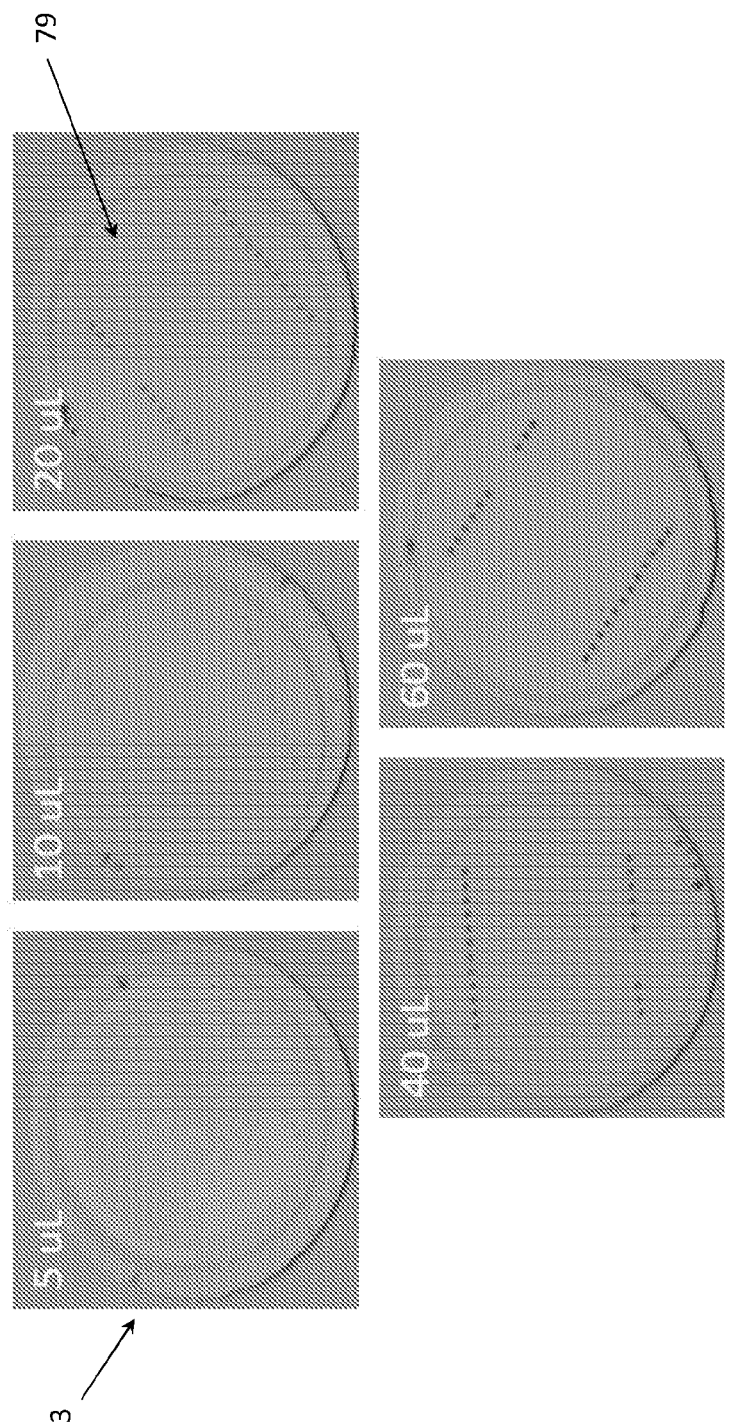
FIG. 26 contains images of membranes for an antibody concentration study for the assay of FIG. 22.
Figure 27A:
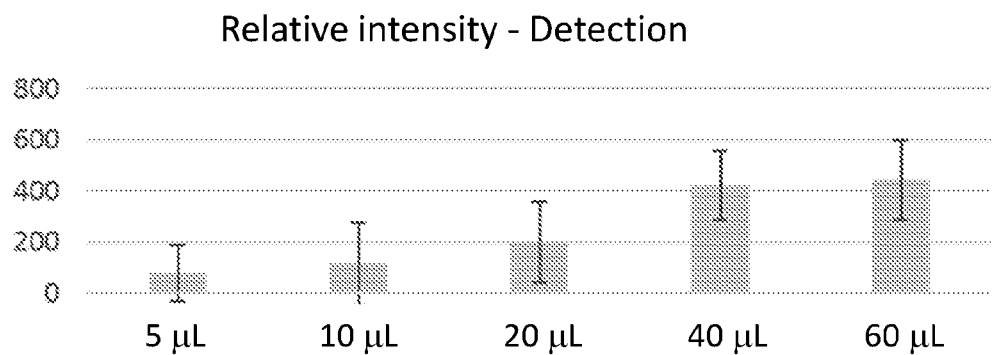
FIGS. 27A and 27B are plots of gray scale intensity for the antibody concentration study of FIG. 26.
Figure 27B:
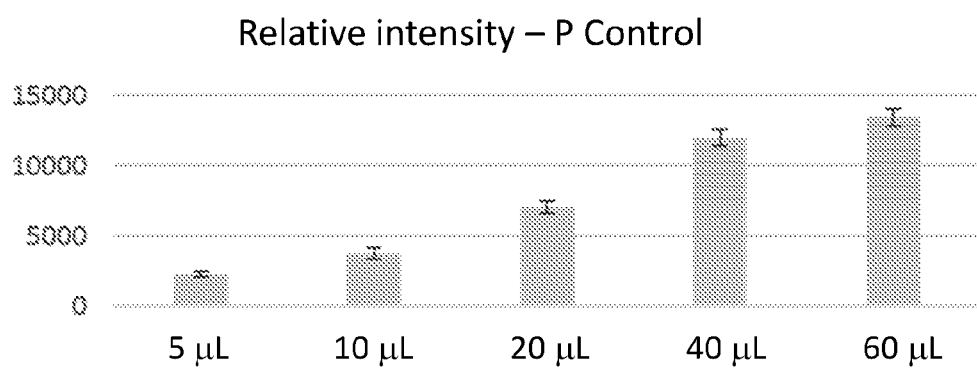

Here, we use 1 mL CPS 1 ng/mL spiked in buffer solution as the sample solution, and test different amount of detection Ab 10 from 5 μL to 60 μL. The results can be seen in FIG. 26. As shown in FIGS. 27A and 27B, the detection Ab 10 concentration increases, the intensity of the detection spots 79 and the positive control spots 79 are both enhanced.

The values of the detection spots 79 and positive control spots 79 show the same rule that as the concentration of the detection Ab 10 increases, both signals get improved. Noted is that the difference between 40 μL ad 60 μL is much smaller than that between 20 μL and 40 μL. It indicates that the sandwich assay might reach the saturation point with about 40-60 μL detection antibody 10.

Sample volume and capture antibody agent 19 concentration study: The capture antibody captures the antigen 13 as the screening sample go through the membrane 3. As one can expect, the more capture antibody agent 19 dispensed on the membrane 3, the more antigen 13 be captured. It also has a saturation point, beyond this point adding more capture antibody agent 19 does not further increase the amount of antigen 13 captured. We can certainly dispense capture antibody agent 19 solution with different concentration, but the dispenser has its limitations on the viscosity of the dispensing liquid. Therefore, we choose to dispense multiple droplets of the capture antibody agent 19 solution to increase the amount of capture antibody agent 19 on the membrane 3.

The capability of processing samples on mL level is another advantage of the VFI system of the disclosed device 1. The sample volume determines the actual amount of antigen 13 passing through the detection spots 79. Increasing the sample volume compensates for a decrease of the target concentration, and thus improves the system sensitivity of the disclosed device 1.

Figure 28:
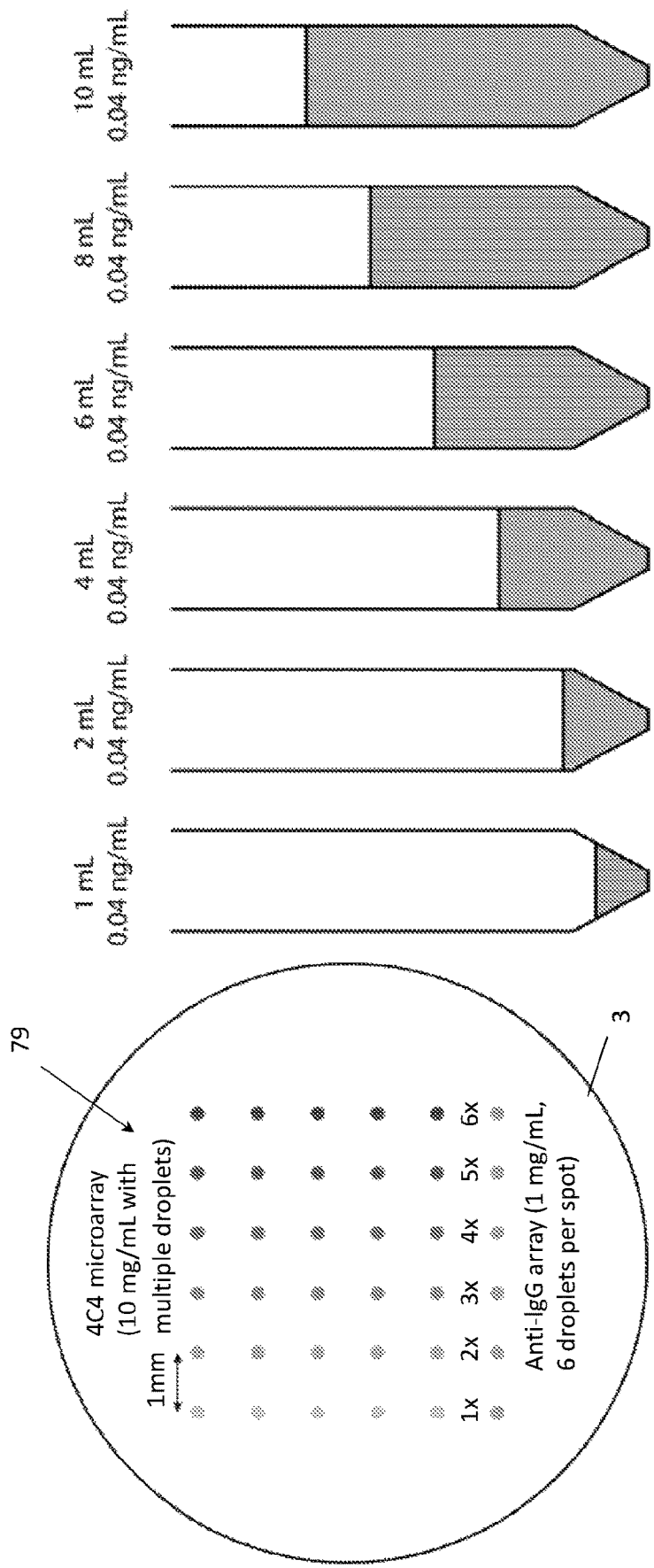
FIG. 28 is a schematic diagram of a experiments to test antigen concentration and sample volume for the CPS assay.

We designed the experiments shown in FIG. 28 to test these two factors at the same time. The microarray (on the left) has 6 rows of detection spots 79. Each row was dispensed with different number of droplets (1-6 droplets, the concentration of the capture antibody agent 19 solution is 10 mg/mL), so that the amount of capture antibody agent 19 was different among the rows. We prepared six screening samples of different volume (1 mL to 10 mL), but with the same CPS concentration of 0.04 ng/mL. The samples were screened at the flow 23 speed of 1 mL/min.

Figure 29:
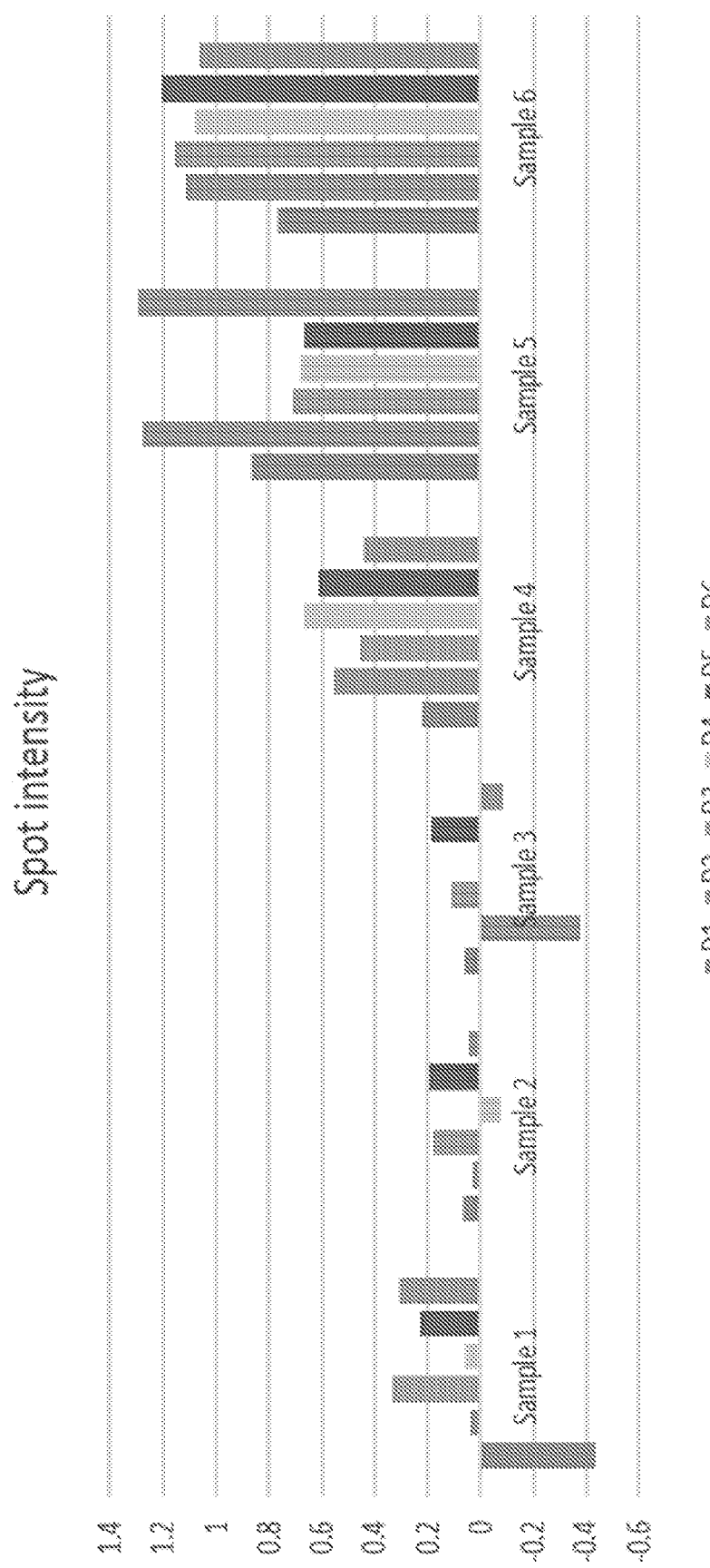
FIG. 29 is a plot of gray scale intensity for the antigen concentration and sample volume study of FIG. 28.

The results can be seen in FIG. 29. As the sample volume increases, the signal intensity increases. 10 mL sample show significantly higher signal than the 1 mL sample. However, within the same sample, the result does not vary much among the spots 79 of different capture antibody agent 19 concentration. It indicates that even single droplet of the 10 mg/mL 4C4 capture antibody agent 19 is more than enough to capture all the antigen 13 passing through.

With the single parameter studies above, it helps to identify the important factors and the range of interest.

3.5 mm membrane 3 system development for the disclosed device 1: We now identified the sample per unit area is a dominant factor in the VFI system. There are two methods to increase it 1) increase the total sample volume, and 2) reduce the size of the membrane 3. The first method is relatively straightforward and does not require any modification of the experiment apparatus. It is especially suitable for bio samples typically with large volume such as urine. However, it does require a much longer time to process the sample. We also tried some conceptual work to reduce the size of the membrane 3, as shown in FIGS. 30A-30C.

Compared with the standard 13 mm membrane 3, we fabricated a smaller version with diameter of only 3.5 mm. It is small enough to fit into the space inside a needle 41 (FIG. 30A). We also fabricated smaller version of the gasket 25, the Si grid support 21, o-ring 77 (FIG. 30C), and an adaptor 43 to assemble them into the needle chamber 45 (FIG. 30B). Theoretically, it can be operated without the syringe 6 pump 31 and be highly portable.

FIGS. 31A, 31B and 31C depict experiment setup and gray scale intensity results for testing of the 3.5 mm membrane 3 setup with the CPS (5 ng/mL) assay at the flow 23 speed of 0.5 mL/min. The results plotted in FIG. 31C show significantly stronger signal (up to 20 times) compared with that from the standard 13 mm disk membrane 3. Such smaller embodiments of the disclosed device 1 can be especially useful for applications in which the sample volume is small and requires ultra-high sensitivity.

Completed the design of a new VFI device 1 that involves six design factors: The most important main effects driving the relative grayscale intensity were the antigen 13 concentration and detection antibody 10 concentration. There were also two significant two-way interaction effects involving the antigen 13 concentration, along with a significant quadratic effect involving the antigen 13 concentration.

Additional design parameters are membrane 3 pore size, buffer pH and buffer ionic strength. Examples of relevant design parameters are: 1. Membrane 3 pore size (0.1-0.45 μm); 2. Antigen 13 Concentration (0.5-1.5 ng/mL); 3. Detection Ab 10 Concentration (note that the range has not been determined yet; the current saturation point is 60 μL); 4. Flow 23 Rate (0.5-1.5 mL/min); 5. Buffer pH (6.5-8.5); 6. Ionic Strength (0.1-0.5).

The goal is to identify ideal values of all of these design factors that will produce the largest relative grayscale intensity with the disclosed device 1.

Based on the evidence for curvature in the response surface, a definitive screening design (DSD) is again appropriate. A DSD can accommodate six design factors in a relatively small amount of runs (17 total) and will enable an estimate of second-order effects without additional runs. The 17 run design table with randomized run orders is shown below:

|    | Membrane Thickness | Antigen Concentration | Detection Ab Concentration | Flow Rate | Buffer pH | Buffer Ionic Strength |
|----|---|---|---|---|---|---|
| 1  | 0  | −1 | −1 | −1 | −1 | −1 |
| 2  | −1 | −1 | 1  | −1 | 1  | 1  |
| 3  | 1  | −1 | 1  | −1 | −1 | 0  |
| 4  | 1  | 1  | −1 | 1  | −1 | −1 |
| 5  | 1  | 1  | 1  | −1 | 1  | −1 |
| 6  | 0  | 1  | 1  | 1  | 1  | 1  |
| 7  | 0  | 0  | 0  | 0  | 0  | 0  |
| 8  | −1 | −1 | −1 | 1  | −1 | 1  |
| 9  | 1  | 1  | −1 | −1 | 0  | 1  |
| 10 | 1  | −1 | −1 | 0  | 1  | 1  |
| 11 | 1  | 0  | 1  | 1  | −1 | 1  |
| 12 | −1 | 1  | −1 | 1  | 1  | 0  |
| 13 | −1 | 1  | 1  | 0  | −1 | −1 |
| 14 | −1 | 1  | 0  | −1 | −1 | 1  |

-continued

| | Membrane Thickness | Antigen Concentration | Detection Ab Concentration | Flow Rate | Buffer pH | Buffer Ionic Strength |
|---|---|---|---|---|---|---|
| 15 | 1 | −1 | 0 | 1 | 1 | −1 |
| 16 | −1 | 0 | −1 | −1 | 1 | −1 |
| 17 | −1 | −1 | 1 | 1 | 0 | −1 |

Automatic image analysis software: To minimize the impact of the observer, an objective observation and analysis software system is needed. The software will analyze the image of the membranes 3 to locate the test area and measure the values for each of the test spots 79. The programming environment is LabVIEW.

Figure 32:
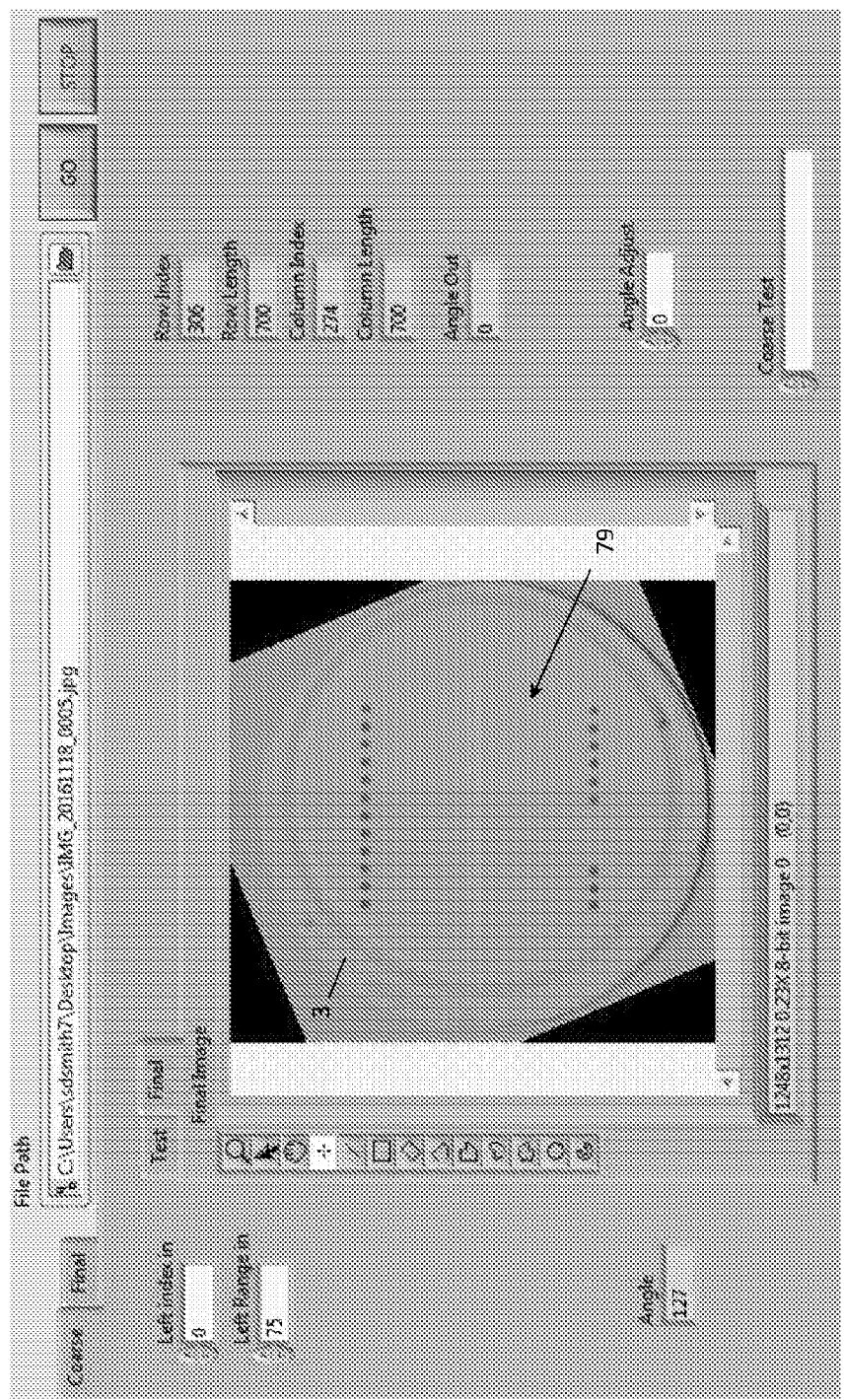
FIG. 32 depicts a window for coarse adjustment in image analysis software.
Figure 33:
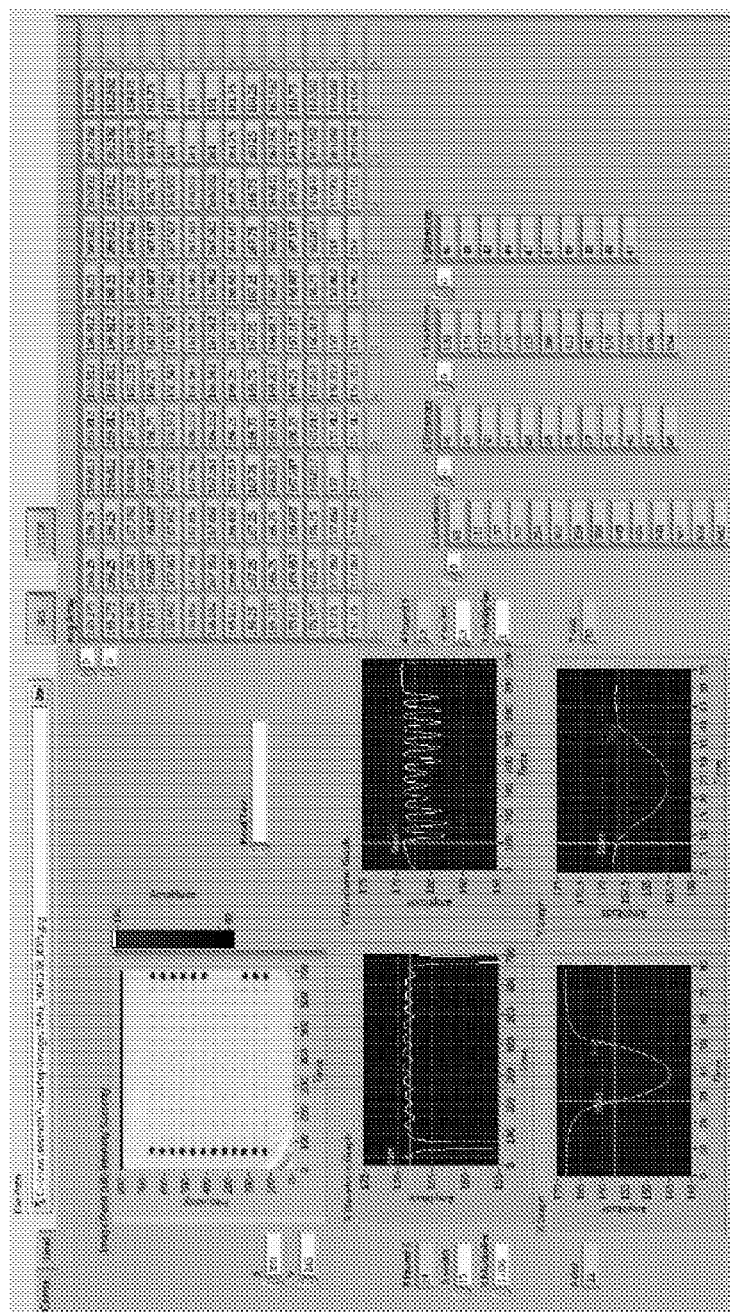
FIG. 33 is depicts a window for detecting the pattern of dots on membranes and evaluating each dot in image analysis software.

The first step is to locate the pattern and orient to a known position. The second step is to analyze the spots 79 in the pattern to determine their intensity. Presently, the software can read the file. In the coarse adjustment, it will rotate the image to orient the image, as shown in FIG. 32. Once located, the software will need to do a fine adjustment to be sure the image is straight. Having oriented the image, the software can detect the pattern and evaluate each spot 79 dot. Currently it provides the average for the center 25 pixels of each spot 79 dot, as shown in FIG. 33. At the current state of the program, automatic orientation is successful in 80% of the test cases. We are examining and testing methods for improving this process. Presently a user is required to tune the analysis process. This part can be automated using known methods and procedures.

Risk and Issues: Risk 1—The variation of the biodot dispenser might generate systematic variation. Mitigation strategy: Use industrial level, or piezo-actuated microdispenser. Resolution: The droplet size we are working with (1 nL) is usually the cut off size of micro-solenoid dispenser. The variation of the droplet is larger than the normal value of 10%. Using an industrial level microdispenser could increase the stability of the entire VFI system in the disclosed device 1.

Risk 2—mAb 1A4 cell line instability. Mitigation strategy: While the 1A4 cell line is still producing, instability and slow growth prompted the decision to make more hybridomas producing Ft reactive mAbs. Resolution: Ten mice were immunized with Ft LPS and are currently being monitored and boosted for maximum immune response. Splenectomy and fusions will be performed to produce a larger library of highly reactive Ft mAbs.

Other factors to examine include: *B. pseudomallei* antibody-antigen binding determined by LFI at different ionic conditions. Production, purification and characterization of a library of highly reactive *Y. pestis* LcrV and F1 specific mAbs. Developed and tested *Y. pestis* LcrV and F1 LFI prototypes. Determined limit of detection with early-stage prototypes using recombinant protein spiked into buffer. Purification of 1A4 (Ft LPS specific) mAb. New murine immunizations and generation of titers specific to *F. tularensis* LPS.

Figures 34A, 34B:
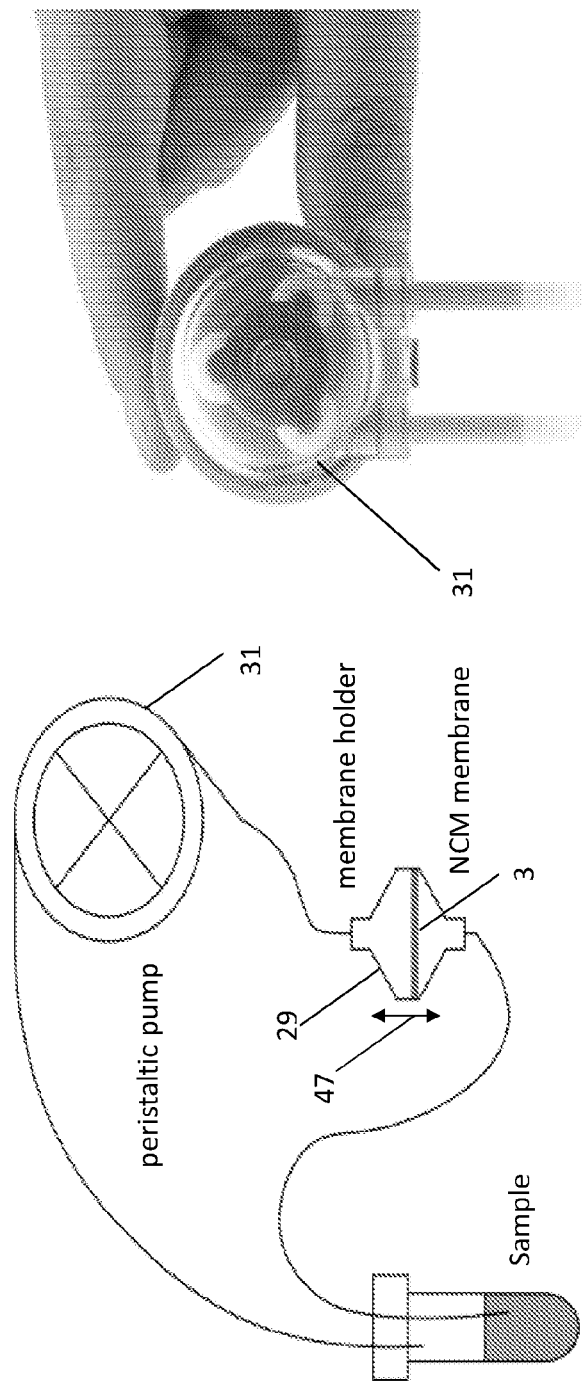
FIGS. 34A and 34B illustrate an exemplary assay setup using a peristaltic pump.

Opportunities include: Re-circulate the sample with a peristaltic pump 31, as shown in FIGS. 34A and 34B. An alternative way is to increase the sample per unit area without requiring a larger sample volume. In this manner, additional opportunity for capture is available, for bi-directional flow 47. Incorporate some active drying step to further reduce the membrane 3 drying time to below 5 mins. With the VFI system of the disclosed device 1, we are able to use membranes 3 with pore size as small as 0.1 μm, which is 100 times smaller than the membranes used for LFI. With such a small diffusion range, the antigen 13 are easier to be captured by capture agent 19 when transiting the membrane 3 pore. The sample per unit area is the most dominant factor in the current sandwich assay. We achieved the largest signal enhancement by reducing the size of the membrane 3. Testing of the 4C4 LFIs with chase buffers of different ionic conditions emphasized the importance of optimal ionic conditions for antibody-antigen binding.

TABLE 1

4C4 LFI prototype was tested with buffer alone or 1 ng/ml CPS in phosphate buffered saline (pH 7.4) at different ionic strengths with or without surfactant P20 in the chase buffer. Optical Density was obtained using ESE Reader after 20 min. Results represent the mean values of two independent experiments.

| NaCl (mM) | Ionic Strength (mol/L) | CPS (1 ng/ml) | Background | Signal − Background |
|---|---|---|---|---|
| PBI chase buffer | | | | |
| 50 | 0.075 | 170 | 222 | −52 |
| 100 | 0.125 | 85 | 38 | 47 |
| 137 | 0.162 | 47 | 5 | 42 |
| 150 | 0.175 | 41 | 0 | 41 |
| 200 | 0.225 | 58 | 21 | 37 |
| 250 | 0.275 | 45 | 0 | 45 |
| 300 | 0.325 | 38 | 0 | 38 |
| PBS + 0.05% Surfactant P20 chase buffer | | | | |
| 50 | 0.075 | 145 | 184 | −39 |
| 100 | 0.125 | 111 | 45 | 66 |
| 137 | 0.162 | 88 | 21 | 67 |
| 150 | 0.175 | 83 | 0 | 83 |
| 200 | 0.225 | 132 | 22 | 110 |
| 250 | 0.275 | 114 | 0 | 114 |
| 300 | 0.325 | 150 | 13 | 137 |

TABLE 2

Binding kinetics and affinity of LcrV mAbs determined by SPR analysis. Readings represent mean values of two independent experiments.

| Clone | ka (1/Ms) | kd (1/s) | KD (M) kd/ka | Rmax (RU) | $Chi^2$ ($RU^2$) | SSKD (M) | Rmax (RU) | $Chi^2$ ($RU^2$) |
|---|---|---|---|---|---|---|---|---|
| 2B2 | 3.6E+04 | 7.3E−05 | 2.1E−09 | 77 | 1.41 | 2.3E−07 | 78 | 0.38 |
| 4E8 | 1.1E+04 | 7.2E−04 | 6.5E−08 | 94 | 10.76 | 5.1E−07 | 95 | 2.35 |
| 5D3 | 2.3E+04 | 4.0E−04 | 3.4E−08 | 85 | 6.08 | 3.7E−07 | 87 | 1.36 |
| 6E5 | 1.5E+04 | 1.9E−05 | 1.3E−09 | 105 | 4.34 | 5.1E−07 | 100 | 1.39 |
| 6F10 | 1.7E+04 | 4.9E−06 | 3.3E−10 | 129 | 3.07 | 4.1E−07 | 127 | 2.08 |
| 8F3 | 1.4E+04 | 1.4E−04 | 9.8E−09 | 80 | 4.17 | 3.0E−07 | 76 | 0.38 |
| 8F7 | 1.1E+04 | 2.0E−04 | 2.0E−08 | 54 | 5.61 | 2.8E−07 | 44 | 0.25 |
| 8F10 | 1.2E+05 | 5.6E−05 | 5.5E−10 | 49 | 1.09 | 6.9E−08 | 44 | 0.15 |

TABLE 3

The limit of detection (LOD) of LcrV mAb pairs determined by antigen 13 capture ELISA. LOD was calculated as the concentration of rLcrV (ng/ml) yielding signal at five times background (OD = 450 nm). The readings represent mean values of two independent ELISAs with each concentration performed in triplicate.

| | | Detection mAb (HRP-conjugated) | | | | | | | |
|---|---|---|---|---|---|---|---|---|---|
| | | 2B2 | 4E5 | 5D3 | 6E5 | 6F10 | 8F3 | 8F7 | 8F10 |
| Capture mAb | 2B2 | 4.21 | 10.16 | 26.87 | 5.94 | 5.77 | 9.32 | ND | 40.08 |
| | 4E5 | 10.13 | 15.70 | 47.87 | 22.87 | 17.34 | 2.20 | 2.54 | 1.76 |
| | 5D3 | 13.03 | 22.92 | 105.66 | 24.35 | 19.44 | 3.55 | 2.51 | 1.92 |
| | 6E5 | 24.01 | 27.85 | 37.21 | 33.95 | 21.74 | 3.06 | 0.84 | 0.61 |
| | 6F10 | 7.62 | 15.67 | 39.56 | 10.72 | 11.41 | 2.05 | 0.84 | 0.65 |
| | 8F3 | 0.75 | 2.15 | 3.89 | 1.12 | 0.89 | 20.36 | 12.06 | 6.27 |
| | 8F7 | 0.81 | 2.34 | 9.56 | 32.16 | 52.38 | 125.67 | 31.77 | 7.69 |
| | 8F10 | 1.07 | 2.68 | 5.64 | 4.75 | 2.33 | 51.18 | 12.69 | 14.44 |

TABLE 4

Binding kinetics and affinity of F1 mAbs were determined by SPR analysis. Readings represent mean values of two independent experiments.

| Clone | ka (1/Ms) | kd (1/s) | KD (M) kd/ka | Rmax (RU) | Chi$^2$ (RU$^2$) | SSKD (M) | Rmax (RU) | Chi$^2$ (RU$^2$) |
|---|---|---|---|---|---|---|---|---|
| 3F2 | 1.7E+04 | 4.8E−04 | 2.8E−08 | 69 | 3.23 | 3.4E−07 | 67 | 0.25 |
| 4E5 | 3.4E+04 | 4.9E−04 | 1.4E−08 | 96 | 3.09 | 2.1E−07 | 92 | 0.73 |
| 4F12 | 1.5E+04 | 1.4E−03 | 9.4E−08 | 73 | 8.94 | 3.6E−07 | 69 | 1.79 |
| 5E10 | 1.6E+04 | 5.7E−05 | 3.7E−09 | 120 | 4.21 | 2.4E−07 | 91 | 0.41 |
| 10D9 | 9.2E+03 | 5.2E−06 | 5.2E−10 | 70 | 3.13 | 5.7E−07 | 67 | 0.24 |
| 11B8 | 1.7E+04 | 5.3E−05 | 3.1E−09 | 103 | 3.89 | 3.5E−07 | 101 | 0.67 |
| 11C7 | 2.0E+05 | 6.3E−04 | 3.2E−09 | 73 | 7.69 | 1.1E−07 | 52 | 0.77 |
| 15C4 | 1.8E+04 | 2.1E−04 | 1.1E−08 | 93 | 17.75 | 2.5E−07 | 73 | 3.21 |

TABLE 5

The limit of detection (LOD) of F1 mAb pairs determined by antigen 13 capture ELISA. LOD was calculated as the concentration of rF1 (ng/ml) yielding signal at five times background (OD = 450 nm). The readings represent mean values of two independent ELISAs with each concentration performed in triplicate.

| | | Detection mAb (HRP-conjugated) | | | | | | | |
|---|---|---|---|---|---|---|---|---|---|
| | | 3F2 | 4E5 | 4F12 | 5E10 | 10D9 | 11B8 | 11C7 | 15C4 |
| Capture mAb | 3F2 | 2.89 | 1.08 | 5.97 | 1.29 | 2.83 | 1.52 | 0.66 | 1.11 |
| | 4E5 | 2.77 | 2.25 | 2.49 | 7.86 | 1.90 | 15.82 | 2.75 | 1.90 |
| | 4F12 | 10.30 | 1.48 | 5.50 | 2.18 | 1.93 | 3.44 | 0.78 | 1.64 |
| | 5E10 | 7.76 | 5.02 | 3.11 | 2.90 | 3.35 | 4.67 | 2.70 | 2.63 |
| | 10D9 | 2.54 | 1.20 | 2.20 | 3.19 | 4.76 | 1.71 | 0.60 | 1.34 |
| | 11B8 | 2.39 | 4.01 | 2.07 | 3.00 | 3.16 | 1.60 | 0.62 | 2.09 |
| | 11C7 | 15.21 | 2.33 | 2.73 | 5.97 | 2.77 | 1.58 | 1.55 | 1.92 |
| | 15C4 | 4.32 | 4.88 | 3.10 | 5.50 | 2.55 | 2.53 | 0.86 | 3.61 |

Example 3: High Flow Sensitive Vertical Flow Diagnostics Devices 1 and Method of Use There are many scenarios requiring biomarker(s) measurement on site with limited resources in a point-of-care setting, such as for cardiovascular disease and cancer prognosis monitoring, as well as infectious disease diagnostics and biothreat detection. In many cases, these biomarkers need to be detected at low concentration (e.g. <1 ng/ml). However, current paper-based lateral flow Immunoassay (LFI), the most popular POC testing format, is not sensitive enough for this requirement. One example is the capsule polysaccharide (CPS), a biomarker for melioidosis, a tier 1 biothreat agent listed by the U.S. government. The current LFI has a limit of detection (LOD) of 1 ng/ml in clinics. At this sensitivity, still a significant portion of the infected patients are not diagnosed by the assay. Simple POC assay with higher sensitivity is critically needed.

Previously, different ways of improving the lateral flow immunoassay sensitivity have been reported. They are mainly divided into two groups. One exploits kinetics of the sensor, i.e. the effects of paper pore size, geometry and sample volume. It is well known that smaller pore size with a slower flow in LFI results in a better sensitivity. Furthermore, Parolo et al. (2013) reported geometry to concentrate sample for better sensitivity in LFI; Pauli et al. (2015) reported a variation of LFI in a syringe vertical flow format to have LOD on-demand by passing different volume of sample through the paper; Oh et al. (2013) reported reduced paper membrane size and larger volume increased sensitivity. However, no effect of sample flow speed has been mentioned. In another work by Chinnasamy, et al. (2014) for multiplexed detection of biomarkers in a vertical flow format, fast fluid flow was reported to reduce background due to shear force, and an optimal flow speed of ~ 1.5 ml/min (i.e. 0.33 mm/sec) was reported.

Another manner is to improve sensitivity is by novel detection mechanisms. Most LFI assays use gold nanoparticle as labels for simple colorimetric detection. Other detection schemes, such as dual gold nanoparticle, silver enhancement, or linked enzyme for chemiluminescent detection, can improve sensitivity, but at the cost of increased complexity.

In this application, in contrary to the well-known effect of slower flow for higher sensitivity in LFI, we achieve a benefit of fast flow 23 for higher sensitivity in the disclosed vertical flow device 1. In ligand-receptor binding biosensors such as immunoassay, the sensitivity is limited by the amount of sample passing through the sensor, and the efficiency of the capturing agent on the sensor. Because POC tests are preferred to be done in a short period of time, a higher flow speed to deliver more sample within a POC time frame (e.g. 10 min), and a smaller paper membrane pore size for better capture efficiency, will improve the assay sensitivity. Any of the devices 1 and methods provided herein may have:
1. The flow 23 speed higher than that in traditional assay (~3.3 mm/sec), but smaller than what would detach the capturing of the target and label by shear (dependent on specific binding kinetics and strength, and may be about >33 mm/sec). Such shear can help to remove non-specific binding to reduce background, further improving signal and sensitivity. Accordingly, any of the devices and methods provided herein may relate to a flow speed or flux that is less than 33 mm/sec, but greater than 3.3 mm/sec, or between about 33 mm/sec and 10 mm/sec, or between about 33 mm/sec and 20 mm/sec, or any sub-ranges thereof; 2. The paper membrane 3 pore size is equal or smaller than traditional LFI for better capturing efficiency (<15 um).

Generally, the disclosed vertical flow device 1 comprises:
1. A porous membrane 3 that is loaded with the capturing agent 19 and control reagents for the diagnostic assay; 2. A porous membrane support 21 that can mechanically support the membrane 3 against the liquid flow 23 to avoid damage. The support can be Si wafer or steel piece with a grid with multiple pores to allow fluid flowing through, or a porous membrane 3 or combination or others; 3. A gasket 25 to press down the paper membrane 3 and prevent liquid leakage. 4. A holder 29 that can hold the gasket 25/membrane 3/support 21 assembly and press the gasket 25 against the membrane 3 on the support 25 so that fluid flows through the membrane 3 and support 21 only within the inner gasket 25 area; 5. A POC pump 31 (e.g. syringe 6 that can be hand-actuated or connected to a powered pump 31) that generates pressure difference across the membrane 3/support 21 to drive the fluid flow 23 at any desired flow 23 rate through the membrane 3 vertically. The pump 31 can be substituted by manual pushing depending on the flow 23 rate needed for different applications; 6. One or multiple spots 79 of capturing agent 19 immobilized on the top surface 5 of the membrane 3 and/or the interior of the membrane 3, such as along the pore surface. Using the micro-dispensing technology, an array of capture antibody agent 19 spots 79 can be dispensed on the membrane 3. Each spot can detect one type of target. This microarray design also minimizes the cross contamination between different assays; 7. A sample solution that may or may not contain the target biomarkers that can be captured by the capture spots 79 on the membrane 3; 8. A detection solution containing a labeling agent that can link to the target biomarkers specifically and generate detectable signals. 9. In one embodiment, the sample solution and detection solution flow 23 through the membrane 3 sequentially; In another embodiment, the sample and detection solutions are mixed and then flowed 23 through the membrane 3 as a complex; 10. A detection system 49 that detects the label on the membrane 3 surface 5, such as gold particle 12 based colorimetric detection by a table top scanner.

Both faster flow 23 and smaller pore size will increase the working pressure to flow sample through the paper membrane 3. The devices 1 and methods provided herein may function under relatively high pressure (~<500 bar, such as in HPLC). For manual generation of high pressure, a syringe 6 with small piston area can be used (e.g. piston diameter <5 mm).

For the holder 29 to be able to withstand the high pressure, it is also good to miniaturize the size of the chamber 39 hosting the gasket 25/membrane 3/support 21.

For limited sample volume, shrinking the membrane 3 area 81 will be able to reach the desired sample volume per unit area required for the high flow 23 operation. For limited sample volume, two supports 21 sandwiching the membrane 3 with gaskets 25 to prevent fluid leak will allow sample to be pushed through the membrane 3 sensor back and forward with bi-directional flow 47 to increase effective sample volume.

The support 21 and gasket 25 can be integrated on the holder 29 for a simpler device 1 and operation thereof.

To reduce the membrane 3 area, wax can be printed and melt on the membrane 3 to block the undesired membrane 3 area.

According to the Department of Health and Human Services, about 70 agents (pathogens and toxins) can potentially pose severe threats to human and animal health upon exposure. Other CBRN threats are also major risks for security and accidents. The exposure often occurs in resource-limited situations, such as rural districts or even in battlefields. Therefore, there is a clear need to develop rapid, point-of-care (POC), multiplexed, and simple-to-use diagnostic devices that can work independently under these settings.

Paper, as an extremely cheap and widely available material, has been well pursued to perform such tasks. The commonly seen lateral-flow format has dominated rapid diagnostics over the last decades because of its low cost and low complexity. However, it is difficult to perform multiplex detection with the dipstick design because assay performance can decrease as the number of target antigens 13 increase. In addition, the sample volume is limited because it is relying only on the capillary force of the paper to transport the liquid. Most importantly, the sensitivity is inadequate for certain infections where biomarkers accumulate below the limit-of-detection (LOD). These limitations can often lower the accuracy of the test, and thus degrade its clinical significance.

Provided herein is a novel vertical flow paper-based immunoassay (VFI) device 1 platform that can be easily adapted for different diagnostic applications. As illustrated, the testing membrane 3 that contains the assay reagents is inserted into a syringe 6 pump 31 needle 41 chamber 45 using an adapter 43. A mechanical grid support 21 is placed underneath the membrane 3 to support the membrane 3 against the liquid flow 23. An o-ring 77 is placed on top of the membrane 3 for suppression and preventing liquid leakage. The testing sample is stored in the syringe and moved through the membrane 3 vertically either by manual pushing or with a syringe 6 pump 31. The device1 can be disassembled after the screening test to retrieve the membrane 3 for imaging and other subsequent analyses.

The disclosed devices 1 and methods are compatible with different detection methodologies other than colorimetric detection. For example, electrochemical detection of biomarkers can be performed with printed electrodes on the membrane 3 substrate. Other schemes such as optical (e.g. SERS) or magnetic detections can also be implemented.

A vertical flow diagnostic device 1 may comprise any one or more of: The porous membrane 3: 1. Can be nitrocellulose membrane 3, PVDF membrane 3, and filter paper as the membrane 3, etc.; 2. Has a high tolerance for the pore size selection (conventional ranges between 0.01 μm to 20 μm). Smaller pore size largely reduces the diffusion range, facilitates the capture reaction involving capture agent 19, and increases the sensitivity; 3. Has a thickness 9 from 10 μm to 1000 μm, but preferably 10-30 μm to have sufficient sites for target capture, and also minimize flow 23 resistance.

The membrane support 21: 1. Can be Si, stainless steel, etc; 2. Has large enough thickness to support the membrane 3, such as >10 μm; 3. Has pore size of 1 μm to 1000 μm; 5. Multiple pores within the gasket 25 area with distributions that gives desired flow 23 rate profile within the gasket 25 area, such as uniform flow 23 across the membrane 3.

The gasket 25: 1. Can be elastic material such as o-ring; 2. Can also be microfabricated material with structures that defines the inner gasket 25 area;

Three configurations are exemplified below, including for different application scenarios.

Configuration 1: The fluid flow 23 can be controlled at a predefined optimal rate so that during certain realistic time frame (e.g. 10 mins for point-of-care application), the labeling signal is maximized. Manual pushing is used to push the fluid through the membrane 3. The piston area of the syringe 6 is reduced to allow maximum pressure available to reach the optimal flow 23 rate. The non-specific binding from clinical sample can also be reduced by the fluid flow 23. The o-ring 77 opening is relatively large, making it suitable for high multiplexed detection with large sample volume.

Configuration 2: The inner gasket 25 area is controlled to be smaller than the membrane 3 area in configuration 1 (~96 mm$^2$, ~3.5 mm diameter) down to similar to a single membrane 3 support pore size (e.g. ~0.00008 mm$^2$, ~10 um diameter for 0.1-μm-pore membrane 3). It is suitable for applications that need very good sensitivity, low requirement for multiplexing, and small sample volume.

Configuration 3: The membrane 3 is sandwiched between two membrane supports 21. Knife edges can be fabricated on the support 21 to integrate the gasket 25 with the support 21. This sandwich configuration allows bi-directional fluid flow 47 to enable recycling through the membrane 3 with optimal flow rate. It can be used for applications that need ultra-high sensitivity with limited sample volume.

Example 4: Development of a Vertical Flow Paper-Based Immunoassay (VFI) Method for Multiplexing Detection of Tier I Bio-Threat Agents More than seventy biological agents and toxins have been determined to pose severe threats to both human and animal health. Exposure to these agents often occurs in austere settings such as battlefields and rural areas where resources are limited. Therefore, it is imperative to develop point-of-care diagnostic tools that are sensitive, cost-effective and simple-to-use that are amenable to multiplexing. We have developed and characterized a vertical flow paper-based immunoassay (VFI) microfiltration device 1 that performs multiplexed detection of Tier I bio-threats. The device 1 platform is based on microbial antigen 13 capture that generates colorimetric signals for direct visualization in less than 10 min.

*Burkholderia pseudomallei* (Tier I agent) is the causative agent of melioidosis, a devastating bacterial infection. A sandwich immunoassay was constructed to detect the *B. pseudomallei* capsular polysaccharide (CPS) in the vertical flow format. A CPS-specific monoclonal antibody (mAb 4C4) was immobilized on a nitrocellulose membrane 3 (pore size <1 m) and served as the capture antibody agent 19. A micro-dispenser was used to spot mAb 4C4 in an spot 79 array format on the nitrocellulose membrane 3. Gold nanoparticles 12 (GNP) linked with mAb 4C4 served as the detection antibody 10, which produces colorimetric signals following binding to CPS. The VFI was run by pre-mixing detection antibody 10 with buffer solution spiked with CPS then the sample was passed through the membrane 3 vertically with a syringe 6 pump 31. After a washing and a drying step, the membrane 3 was scanned with a standard tabletop scanner and analyzed using an automated imaging analysis software.

To characterize the VFI system of the disclosed device 1, a design of experiment (DOE) screening analysis was created in JMP Pro 13. Seven VFI parameters were studied, including six continuous factors—flow 23 rate, assay time, GNP 12 amount, premixing time, buffer pH, buffer ionic strength, and one categorical factor-membrane 3 type.

Results and Conclusion: Traditional paper-based lateral flow assays may have limited sensitivity and multiplexing capabilities due to the small sample volume and the need of relatively large membrane pore size (>10 μm), which is inefficient for target capture. The disclosed VFI device 1 provides a good solution to these problems by implementing active fluid pumping.

According to the DOE results, flow 23 rate and assay time were the two most important factors affecting the average signal intensity, followed by membrane 3 type, pH, and premixing time. There was a 2-factor interaction between flow 23 rate and assay time, indicating that the sample volume per unit area might be the key to further improving the sensitivity of the disclosed VFI device 1. As for the signal variation, GNP 12 amount and membrane 3 type were the dominating factors, followed by flow 23 rate. The screening design identified key factors that will be studied for further VFI device 1 optimization.

Under these optimum experimental conditions, the current VFI's limit-of-detection (LOD) for the CPS assay is 4 pg/mL (10 times lower than a previous lateral flow device). We also demonstrate multiplexing detection of CPS and PGA (a biomarker for *B. anthracis*, the causative agent of anthrax). The VFI system of the disclosed device 1 may be characterized for detection of a variety of biothreats, and validated for multiplexing capabilities and improvement of performance through miniaturization.

Example 5: Design Guidelines and System Specifications

Parameter 1—Membrane 3 materials and pore size: Design rules: Membrane 3 material with high protein binding capability is preferred. Smaller the membrane 3 pore size, better the detection sensitivity. Due to the extremely small flow 23 path (~130 um), nanopore membrane 3 can be used in the VFI system of the disclosed device 1. Suggested value: Nitrocellulose membrane 3 with 0.1 um pore size shows the best sensitivity with the assays for melioidosis, anthrax, and plague.

Parameter 2—Capture antibody agent 19: Design rules: The higher the density of the capture antibody agent 19 on the membrane 3, the more binding sites are available to capture the target antigens 13. The concentration of capture antibody agent 19 should be pushed to saturation based on the loading capacity of the membrane 3 material. Suggested value: One droplet (with a volume of 1 nanoliter) capture antibody agent 19 solution (10 mg/mL) is deposited on the membrane 3 as the detection spot 79.

Parameter 3—pH: Design rules: In the tested range (pH 6.4~8.4) in buffer, pH can be significant. Suggested value: assay dependent.

Parameter 4—Ionic strength: Design rules: In the range we tested (50~450 mM), value below 150 mM gave high background, no significant effect of the ionic strength was observed for values between 150~450 mM in the VFI system. Suggested value: 150~450 mM.

Parameter 5—Matrix Type

Design rules: Three types of most commonly used human body fluid serum, urine can be used in the disclosed VFI device 1. Serum and plasma have narrow pH and ionic strength range, and variations from these two factors are usually not significant. Human urine sample, which is known for big variations of pH and ionic strength, (up to 10-fold difference), which requires more in depth characterization in the VFI system of the disclosed device 1. A pre-filtration through 0.2 um Polyethersulfone (PES) membrane is preferred to remove any micro-particles and cellular components that might clog the VFI membrane 3. Suggested value: Serum, plasma or urine.

Parameter 6—VFI device 1 reaction scheme: Design rules: Premixing scheme: mix the sample with the detection antibody 10 labeled GNP 12 before it is flowed through the VFI membrane 3; Sequential scheme: flow the sample and the detection antibody 10 labeled solution through the membrane 3 in sequential steps. Suggested value: Our result shows premixing is preferred, but may be assay dependent.

Parameter 7—Detection antibody 10 labeled AuNP 12: Design rules: For assay that uses the same antibody for both detection and capture, such as the CPS assay, increasing the concentration of the detection antibody 12 labeled AuNP 12 does not improve detection sensitivity significantly. For assay that uses different antibody for detection and capture, such as the LcrV assay, increasing the concentration of the detection antibody 10 labeled AuNP 12 could significantly improve the detection sensitivity. More experiments are currently being performed to find the optimum concentration of the antibody labeled AuNP 12 in the LcrV assay that give the best contrast between the detection spot 79 and the background. Gold nanostars versus standard spheroid NP 12 are also under evaluation as the branched NP have higher scattering coefficients and tunable wavelength for possibly increasing reflectance when used in CCD based camera detection. Suggested value: Assay dependent.

Parameter 8—Unit flow rate: Design rules: Unit flow rate (mm/s) is defined as the sample volumetric flow rate (mL/min or $cm^3$/min) divided by the surface area 81 ($mm^2$) of the VFI membrane 3. The higher the unit flow rate is, the more samples can be delivered to the sensing area 81 in a constant time, and the better detection sensitivity can be achieved. The unit flow rate is limited by the pump 31—higher the flow 23 rate, higher the required pressure, which could either stall the pump 31 or break the VFI housing (e.g., holder 29). Suggested value: Based on the pump 31 we are currently using (New Era syringe pump NE1000), flow 23 rates can readily be 1.5 mm/s.

Parameter 9—VFI test time: Design rules: Premixing time: it is the time the sample is mixed with the antibody labeled AuNP 12 solution. Longer the premixing time is, better the antigen 13 can be labeled with the AuNP 12. VFI running time: it is the time the sample (mixed with the labelled AuNP 12) being pushed through the VFI membrane 3. Given a constant flow 23 rate, longer the running time is, the better the detection sensitivity. Suggested value: The current setting is 10 min premixing time and 10 min running time. The 10 min running time was selected to match the time needed for a lateral flow test, but could be modified based on the need of the users.

Parameter 10—Membrane support 21 grid: Design rules: The rigidity of the membrane support 21 determines the deformation of the membrane 3 during the flow through step, which could impact the signal uniformity across the membrane 3. The more rigid the support 21 can be, the less non-uniform the signal is across the membrane 3. Suggested value: Deep etched Si support 21 is used in the current VFI setup for the disclosed device 1.

Parameter 11—Membrane 3 size and multiplexity: Design rules: The surface area 81 of the VFI membrane 3 determines the total number of spots 79 and thus the multiplexity of the test can be integrated with the disclosed VFI device 1. Spot 79 size is a limiting factor of the multiplexity, which is dependent on the droplet size of the micro-dispenser. With our current micro-solenoid value dispenser, the smallest droplet volume is 1 nanoliter. However, with more advanced piezo-dispenser, the droplet size can be reduced to picoliter level, so that the spot 79 size can be made much smaller. Suggested value: With our current dispenser, we could have 7 spots/$mm^2$; but other dispenser showed 11 spots/$mm^2$.

Parameter 12—Sample volume: Design rules: Sample volume is decided by the unit flow rate and the surface area 81 of the membrane 3. VFI accommodates a much larger range of samples volumes: currently the standard VFI processes samples 1 mL to 50 mL and above, and the mini VFI processes samples from 500 μL to 5 mL. Adding an extra dilution step, the lower bound can be further extended to 100 μL without losing much sensitivity. Such wide range of sample volume gives the disclosed VFI device 1 a lot of flexibility in dealing with different types of samples. Suggested value: Standard VFI device 1 processes samples 1 mL to 50 mL and above, and the mini VFI device 1 processes samples from 100 μL to 5 mL.

Parameter 13—Device 1 Integration and software: Design rules: Currently the membrane 3 and support 21 for the disclosed device 1 are designed into Luer-lock devices to fit most standard syringes 6. In the case of nucleic acid configuration, the system of the disclosed device 1 will also integrate a sample preparation module coupled with the VFI device 1. Data analysis software for imaging with smartphone device 51 camera 53. Suggested value: Plastic syringes and Luer-lock connector.

Example 6: Vertical Flow 23 by a Passive Capillary Driven System 55

Other systems are available to ensure appropriate vertical flow 23 occurs across the membrane 3. For example, a passive/capillary pumped vertical flow device 1 is compatible with large sample volume/area. A similar sample volume/area is achieved compared to an active pumped device 1 (e.g., a pump 31 powered by an external source of energy, such as electricity). Replacement of an active pump 31 with a passive flow 23 makes the process simpler.

The device 1 in this example is a vertical flow device 1 for singleplex or multiplex biomarker detection. The difference between this device 1 and previously described vertical flow device 1 is that the reagent/fluid of this device 1 is pumped by the passive capillary force of an absorbent material 57, in contrast to an active mechanical pump 31.

Figure 35:
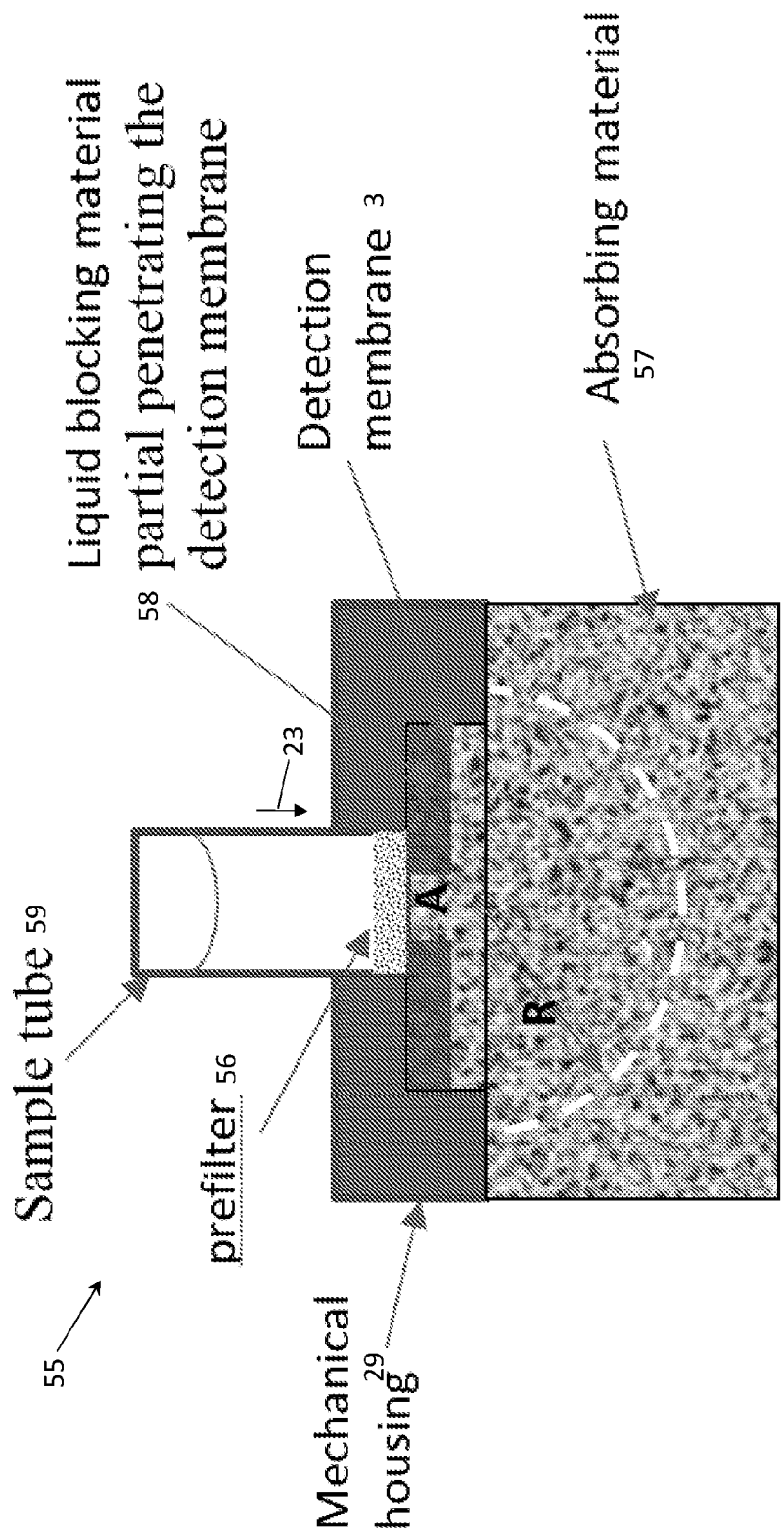
FIG. 35 is a schematic diagram a passive capillary driven vertical flow system.

FIG. 35 provides an illustration of an exemplary embodiment of the passive capillary driven vertical flow system 55. Relevant aspects include: (1) There is a detection membrane 3, similar to the detection membrane 3 in other vertical flow device 1, where capturing agent(s) 19 can be immobilized on the membrane 3; (2) The detection area 81 has an area of "A". This area 81 can be defined by a gasket 25 mechanism, or by printing a layer of liquid impermeable material (the liquid blocking material 58) on the membrane 3, such as wax printing or by a masking tape. (3) There is a "sample tube/holder" 59 on top of the detection membrane 3 to hold the sample. The sample will be pre-filtered before going into the detection membrane 3. The pre-filter 56 can be external, or together with the sample tube/holder 59. (4) There is an absorbent material 57, acting as a capillary pump to pull the sample through the detection membrane 3 over time so that: (a) the sample volume going through the detection area 81 is higher than ~200 µL per mm$^2$ of detection membrane 3, i.e. total volume of 200 mm*A; (b) where the capillary action is completed in a point-of-care time frame, e.g. 10-30 min, which means that the fluid flow 23 speed is higher than ~0.2 mm/sec; (c) where the absorbent material 57 that accommodates all the sample volume fans out relative uniformly, with "A" as the center.

In practical use, usually "A" has an area of 100 to 0.01 mm$^2$, "A" can have a circular shape. "A" could have a line shape, but the absorbent material 57 also fans out beyond the outline of "A" uniformly.

Example 7: Cost-Effective Methods for Expedient Dosimetry to Support Diagnosis of Radiation Injury A mass-casualty nuclear disaster, such as detonation of a terrorist dirty bomb or a nuclear power plant incident, requires an effective and fast medical response in order to treat and save thousands of lives. First responders must precisely assess the absorbed radiation dose in order to distinguish those who need immediate medical intervention from those who are candidates for delayed treatment.

Although there is no bio dosimetry method approved by the U.S. Food and Drug Administration (FDA) yet, the dicentric chromosome assay (DCA) is currently considered the "gold-standard". This assay is very specific to ionizing radiation and low background levels of dicentric chromosomes allow it to be highly sensitive. However, like all cytogenetics-based assays, the DCA is labor intensive and takes a long time to estimate the dose, an important limitation for radiation dose assessment in an emergency scenario.

The development of gene expression profiles, especially in peripheral blood lymphocytes, has been suggested as an alternate approach to radiation bio dosimetry. Exposure of human cells to environmental stresses, including IR, is known to activate multiple signal transduction pathways, and rapidly results in complex patterns of gene expression change. In contrast to DCA or the micronucleus assay, gene expression does not require cell division and can be analyzed quickly with advanced molecular assays (Lacombe et al., 2018). However, in order to process and analyze such large numbers of samples and return results in a few hours, technology development requires automation and miniaturization to provide a point-of-care device integrated in a high-throughput platform.

With the advancement of nanotechnology, paper materials have been utilized for biomedical applications and show promising capacities and advantages. A majority of the reported paper devices are designed in a lateral flow immunoassay (LFI) format where the fluid flow is parallel to the surface of the paper. The main benefits of LFI include low cost, rapid results, flexibility and ease of use. However, in order to achieve an adequate flow rate, the pore size of the paper materials is limited to several micrometers and above, which hinders biomolecule capturing and thus the assay sensitivity. In addition, sample volume constraints and the difficulties of multiplexing are other hurdles that confront LFI development. One approach to improving upon the LFI platform has been the development of flow-through devices. This alternative format is similar to LFI in that it is a membrane-based immunoassay, however, fluids are applied vertically to the surface of the membrane rather than parallel (Chen et al. 2018). As such, vertical flow immunoassays provide better sensitivity, are faster, and avoid the hook effect.

Provided herein is a cost-effective, rapid flow-through paper-based device 1 for nucleic acid detection—offering an accurate, reliable, miniaturized and automated high-throughput bio dosimetry platform that will have a higher specificity and sensitivity than the existing DCA assay.

Technical Objectives: The assessment of gene expression profiles, especially from human circulating cells in biofluids such as blood, is a promising approach to standard but labor- and cost-intensive cytogenetic assays for radiation bio dosimetry. Provided herein is a Vertical Flow Paper-based device 1 Platform (VFP) (FIG. 36) for assessing expression level of radiation dosimetry genes from PBMCs after irradiation. In this manner, the devices and methods can accurately measure the absorbed dose of irradiation:

Detection of 4 different genes (3 radiation-responsive genes and 1 housekeeping gene) using VFP approach. The device is to detect three radiation-responsive genes on the same membrane 3 and measure and calculate their expression level between non-irradiated and irradiated samples by using housekeeping gene also detected on the same membrane 3 for normalization (total of four genes on a single membrane 3). Results indicate that two genes from cell lines are able to be amplified and detected on VFP membrane 3 simultaneously. Here, we use whole blood as a biological sample to demonstrate assay feasibility on human biofluid. Blood samples are irradiated and RNA extracted and quantified. PCR primers are designed for a panel of genes, with target(s) amplified using standard PCR and amplicons assessed by using agarose gel. The three radiation-responsive genes and the housekeeping gene with the highest signal are selected to be passed and detected on VFP membrane 3. In order to assess the ability of the disclosed VFP device 1 to detect and quantify gene expression change after irradiation, gene expression using VFP is analyzed and compared with real-time qPCR approach.

Relevant aspects include: Whole blood sample collection and sample processing (cell culture, irradiation, RNA extraction, RNA quantification, etc.); development of PCR primers for a panel of radiation-responsive genes and housekeeping genes (primer design, PCR experiment optimization, product assessment); detection using VFP and comparison with real-time qPCR (confirmation of range, accuracy, and throughput along with specificity, multiplexing, signal sensitivity, etc.)

Other technical aspects include isothermal amplification using recombinase polymerase amplification (RPA)—We develop an isothermal amplification method using recombinase polymerase amplification (RPA) while simultaneously developing a VFP for diagnosis of radiation injury. This approach facilitates a faster sample preparation by avoiding standard amplification and, hence, will be easier to integrate into a fully automated sample preparation platform which gets combined with the disclosed VFP device 1, for maturation into phase II prototype. RPA is developed using whole blood, using the same primers described in technical objective 1. The quality of the amplicons is assessed using agarose gel or ELISA prior to testing on the VFP.

These aspects include: whole blood samples collection/processing (cell culture, irradiation, RNA extraction, RNA quantification, etc.); RPA development (experimental optimization, primer design, product assessment); detection using the disclosed VFP device 1 (confirmation of range, accuracy, and throughput along with specificity, multiplexing, signal sensitivity); Optimization of isothermal amplification for VFP (time, temperature, etc.)

To accurately measure an absorbed dose of irradiation in a manner that is readily scalable, aspects to consider include: a) PCR primers (Primer design) for the designated target gene panel and b) PCR product quality assessment method; detector selection to achieve best signal to noise ratio; quantification strategy for reporting the results; Sample Type, Collection and storage; Sample processing. The system is assessed to demonstrate binding affinity in terms of best Signal to Noise ratio.

Methods:

Sample collection and processing—Whole blood samples, pooled from different individuals and mixed gender, is ordered from a certified company (BioChemed). Blood collected with heparin or sodium citrate is preferred since chelating agents sometimes used as anticoagulants (e.g. EDTA) could interfere with magnesium and thus reduce efficiency of PCR.

Upon reception, blood is aliquoted in 1.5 mL microcentrifuge tube (~1 mL) and exposed to 0, 2, 4 and 6 Gy X-rays using the X-RAD 320 (Precision X-Ray Inc., North Branford, CT). Irradiation is performed at 320 kVp and 12.5 mA with a 2 mm Al filter. The source-to-axis distance is 42 cm and dose-rate 3Gy/min. The beam is calibrated using a UNIDOS E PTW T10010 electrometer and TN30013 ionization chamber, with measurement done in air, for a 15 cm×15 cm field size. After irradiation, blood samples can be diluted 1:1 with RPMI 1640 medium (Invitrogen) supplemented with 10% heat inactivated fetal bovine serum (Invitrogen) and incubated in 6-well plates for 24 hours at 37° C. in a humidified incubator with 5% $CO_2$.

After 24 hours, RNA is extracted using QIAamp® RNA Blood Mini Handbook (Qiagen) following manufacturer's recommendations. RNA quality is tested and quantified by using Agilent 2100 Bioanalyzer System (Agilent) and Epoch™ Microplate Spectrophotometer (Biotek) and then stored at −80° C. until use.

Standard amplification—In order to maximize success rate, PCR primers from several radiation-responsive and housekeeping genes are designed. BAX, CDKN1A, DDB2, FDXR, GADD45A, and HIST1H3D are selected as radiation-responsive genes. These genes have been identified by numerous studies as radiation dosimetry biomarkers candidates in PBMCs and have been recently reviewed in several meta-analysis (Lacombe et al., 2018; Lu et al. Sci Rep. 2014). CDR2, MRPS5 and MRPS18A genes are selected as housekeeping genes. These genes have been published and are currently used for normalization in a validated and approved diagnostics' radiation blood test (DxTerity Diagnostic, Lucas et al., 2014). PCR primers are designed by using PRIMER-Blast (NCBI). Whether some genes have several transcript variants, primers pairs targeting all these variants are preferentially selected. Primers crosslinking with others genes are excluded to ensure specificity. Amplicons whose size is above 400 base pairs (bp) are selected in order to be detectable by agarose gel. In order to be detected by immunoassay using VFP, for each primer pair, forward primer are modified on its 5' end by adding FITC group and reverse primers are modified on its 5' end by adding a different chemical group for each genes (Cy3, DIG, DNP, etc.).

RNA is first converted into cDNA by using RNA to cDNA EcoDry™ Premix (Oligo dT) kit (Takara). This kit is a convenient dry master mix that allows efficient and accurate first-strand cDNA synthesis. As such, reconstitution is simple by adding PCR-grade water along with your RNA to master mix. This system thus facilitates potential integration into automated point-of-care platform for sample preparation. Second, standard amplification by PCR is performed using High Yield PCR EcoDry™ Premix. Similarly to the RT-PCR kit, this kit contains a lyophilized master mix which are reconstituted with PCR-grade water, cDNA and the designed primers. Amplification efficiency and amplicon size are assessed by conventional 2% agarose gel with ethidium bromide before VFP analysis. In order to assess VFP quantification efficiency, amplicon are also amplified by real-time qPCR. The same primers, but without any modifications on their 5' end, are used to perform qPCR. qPCR are performed on Stratagene Mx3005p (Agilent) by using $RT^2$ SYBR Green ROX qPCR Mastermix (Qiagen) following manufacturer's recommendations. Relative fold-change are calculated by the ΔΔCT method. Data are normalized to CDR2 and/or MRPS5 and/or MRPS18A genes expression levels in order to define the best individual or panel housekeeping genes.

One analysis is performed based on linear regression. The R2 value for a linear fit (fold change vs. radiation dose) are calculated for each gene and genes with R2>0.9 (or the three genes with the highest R2 value) are selected as behaving linearly. The three radiation-responsive genes and the housekeeping gene with the highest signal on agarose gel and radiation-responsive gene with the best linearity is selected for multiplex VFP analysis.

Gene expression levels are normalized with housekeeping genes and fold changes are calculated and compared between VFP and qPCR. The three radiation-responsive genes and the housekeeping gene with the highest signal on agarose gel and the highest fold change ratio between non-irradiated and irradiated samples detected with qPCR are selected for multiplex VFP analysis.

Construction of the VFP device 1 and data analysis—The disclosed VFP device 1 comprises either a 13 mm or 3 mm diameter nitrocellulose membrane 3 encapsulated in a stainless steel filter holder 29 (Swinny Filter Holder 13 mm XX3001200, Millipore, MA, USA). A polytetrafluoroethylene (PTFE) gasket 25 and o-ring 77 is placed below and on top of the paper membrane 3 respectively to seal the liquid flow 23 pathway. The gasket 25 and o-ring 77 is purchased as a package together with the Swinny filter holder 77 from Millipore. A syringe 6 pump 31 (NE-1000 automatic single syringe pump, New Era Pump Systems, Inc., NY, USA) is used to push the samples and reagents vertically through the paper membrane 3 at a controlled flow 23 rate. We fabricate the support 21 with silicon using deep etching method instead of using commercially available stainless steel support. The silicon grid of the support 21 mechanically supports the membrane 3 against the flow 23 during the flow through processes.

A VFP device 1 may be built using nitrocellulose membrane 3 because of its high protein-binding capability and availability in a range of small pore sizes. Four nitrocellulose membranes 3, Amersham Protran 0.1 µm NC, 0.2 µm NC, 0.45 µm NC, and Whatman AE98 (pore size 5 µm) (GE Healthcare Life Sciences, PA, USA), could be tested and compared. The four types of membrane 3 all consist of 100% pure nitrocellulose with different pore sizes. The membranes 3 are cut into shape using a $CO_2$ laser (VersaLaser 2.30, Universal Laser Systems, AZ, USA). The capture antibody agent 19 microarray of spots 79 is dispensed onto the paper disks using a micro solenoid non-contact robotic dispenser (AD1520 micro-dispenser with BioJet Elite, Biodot, CA, USA) with a droplet volume of 1 nanoliter, which creates circular spots 79 of 220 µm in diameter.

Specific capture agent 19 antibodies (against one extremity of the amplicon labelled specifically with a different compound for each gene) are first immobilized on the paper membrane 3. All amplicon also containing a FITC modified 5' end, thus a FITC-labelled gold nanoparticle 12 (FITC-GNP) are used as unique detection agent for all the target. Two experimental procedures, i.e. premixing and sequential, can be tested and compared. PCR products are spiked in buffer solution (0.1 M PB buffer containing 0.1% Triton X-100 and 0.1% BSA, pH=7.2) containing the FITC-GNP 12 for 10 min. In the meantime, the membrane 3 are treated with blocking buffer (10 mM borate buffer containing 2.5% Triton X-100, pH=8). The sample mixture is pushed through the membrane 3 to allow capture of the PCR products-FITC-GNP 12 complex by the capture agent 19 antibodies on the membrane 3. After the sample is processed, the membrane 3 is washed by flowing 1.5 mL blank assay buffer through the membrane 3 to remove non-specific or loosely bound amplicon and excess FITC-GNP 12. The VFP device 1 is dismantled and the membrane 3 placed on a filter paper (Whatman qualitative filter paper, Grade 1, GE Healthcare Life Sciences) for 5 min as a drying step. Subsequently, the VFP membrane 3 is scanned with a consumer-grade table-top scanner (CanonScan 9000 F II) and Scan IJ Utility (default software for the CanonScan), with 48 bits RGB settings and 2400-dpi resolution exported into an uncompressed TIFF file format. The 48 bits RGB image will be then converted to 16 bits grayscale image using the built-in function rgb2gray of Matlab (Mathworks, MA, USA). The resulting image is imported into ImageJ, where the spots 79 are analyzed using a microarray grid to extract the mean grayscale values from the spots 79 with subtracted local background. The limit-of-detection (LOD) is defined as the concentration that generated a signal that is greater than 3 standard deviations (SD) above the background signal. Data processing and analysis is performed.

Specificity of the VFP membrane 3 is assessed by flowing the individual amplicons though a membrane 3 printed with the four capture agent 19 antibodies. Indeed, the membrane 3 is first coated with the four specific capture agent 19 antibodies. Then, samples containing only one amplicon is flowed through the membrane 3. This experiment is repeated four times, for each amplicon. Signal is detected for each capture agent 19 antibodies. Signal for the targeted antibodies is considered significant and specific if signal is at least two times higher than the background (determined as signal generated by spot 79 printed with PBS). Radiation-responsive genes expression levels are normalized with the selected housekeeping gene. Similarly to qPCR data processing, resulting fold changes are plotted into a linear fit curve in function of radiation dose in order to compare VFP and qPCR results and assess VFP power as biodosimetry gene expression assay.

Isothermal nucleic acid amplification-Isothermal nucleic acid amplification can be based on Recombinase Polymerase Amplification (RPA) which represents a hugely versatile alternative to polymerase chain reaction (PCR) for the development of fast, portable, nucleic acid detection assays. RPA is developed from the same whole blood samples as previously described. RNA is extracted according to the same protocol as previously described. RPA amplification can be entirely performed by using TwistAmp kit (TwistDX) following manufacturer's recommendation. This kit has been developed to amplify DNA, but we add reverse transcriptase (AMV reverse transcriptase, Sigma-Aldrich, efficient at 42° C.) to the reaction mix in order to amplify RNA. The same PCR primers designed for standard PCR are used for the reaction. RPA products can be assessed by agarose gel and finally detected with VFP.

First, reaction is performed at 30 min at 42° C. If efficient, different timing points are assessed to decrease to up to 10 min if possible. VFP being very sensitive, we expect that even a short time of amplification can be sufficient to detect signal.

However, although manufacturer claims that RPA can work with PCR primers, RPA may require longer primers amplifying shorter sequence. If we cannot detect any amplicon, new primers are designed specifically oriented for RPA. For such an approach, agarose gel technique may not be ideal to detect RPA product (shorter than PCR products) and as a result we can use sandwich ELISA to assess RPA efficiency.

We are able to detect two different genes (CDKN1A and HIST1H3D) on the same VFP membrane 3 with a high specificity suggesting the possibility of using a multiplex approach for several targets. By quantifying colorimetric signal on VFP membrane 3, we also illustrate an ability to detect difference in gene expression levels between non-irradiated and irradiated samples.

We also detect the surface capsular polysaccharide (CPS) of *Burkholderia pseudomallei* pathogen. We optimize parameters and critical factors of VFP. We thus show that increasing the flow 23 speed (up to 1.06 mm/s) and reducing the membrane 3 pore size (down to 0.1 µm) can improve the sensitivity by at least 5 times. The VFP's limit-of-detection for CPS spiked in buffer solution is determined to be 0.02 ng/mL suggesting that the disclosed VFP device 1 shows great potential as a point-of-care tool for immuno-detection of molecules in a variety of clinical and resource-restricted conditions (e.g. rural or battlefield environment).

This example provides a bio dosimetry device 1 suitable for rapidly measuring expression levels of a low-density genes that can define radiation exposure, dose and injury in case of a public health emergency.

The devices and methods may be validated, including to satisfy agency regulations, with a large population of cancer patients from multiple sites and different treatment modalities.

Example 8: Human-Centered Design Augmentation of the Vertical Flow Paper-Based Health Monitoring Platform This example presents a human-centered design of a VFP platform working in microgravity environment for space mission, including integrated sample preparation modules for gene expression based health monitoring. The platform is designed to ensure safe operation in spaceflight, as well as usability to the unique demographics of the end user (astronauts). This addresses the need in the field to develop human-centered designs for the disclosed Vertical Flow Paper-based Platform (VFP) device 1 with more operability and usability, improved efficiency and safety, decreased errors and reduced learning curve for space health monitoring.

The disclosed VFP device 1 is a mobile point-of-care (POC) uses a miniaturized "syringe-like" cartridge that is capable of detecting tens or hundreds of biomarkers in small or large volume of bodily fluids in a short period of time (~10 min) (e.g., as shown and described above with reference to FIGS. 2A-2C). The device 1 platform is based on antigen 13 capture by specific antibody pairs with colorimetric signals from nanoparticle 12 labels that can be detected by direct eye visualization or by a standard camera 53 of a smartphone 51 as a reader. The disclosed VFP device 1 platform has demonstrated ~25× improved sensitivity comparing with standard lateral flow assay for antigen 13 biomarker detection. The TRISH VFP project is expanding the capability of the disclosed device 1 platform by detecting gene expression biomarkers for astronaut health monitoring in space flight (e.g. biodosimetry or infection).

The current VFP platform of the disclosed device 1 is designed for POC detection of antigen 13 biomarkers on earth, but has not been optimized for space missions. The expansion of the device 1 platform for gene expression biomarker detection also requires an additional module for the sample preparation process. For devices 1 operated during space missions, it is imperative to ensure safety of the mission, including safety of general public, the astronauts, NASA workforce and high value equipment. It is also important to consider the demographics of astronauts. They are highly educated, trained and motivated, but overtasked. There are also numerous factors in a space mission that will decrease the capacity of processing information, memory recall, strength and attention for astronauts during space mission, such as reduced gravity, fatigue due to circadian misalignment, decreased visual acuity with headward fluid shifts, acoustic sensitivity and other stresses of long-duration deep space exploration. The special environment (e.g. ionizing radiation) and limited resources in space mission (mass, power, volume etc.) are additional factors that need to be considered for device used during spaceflight.

Figure 37:
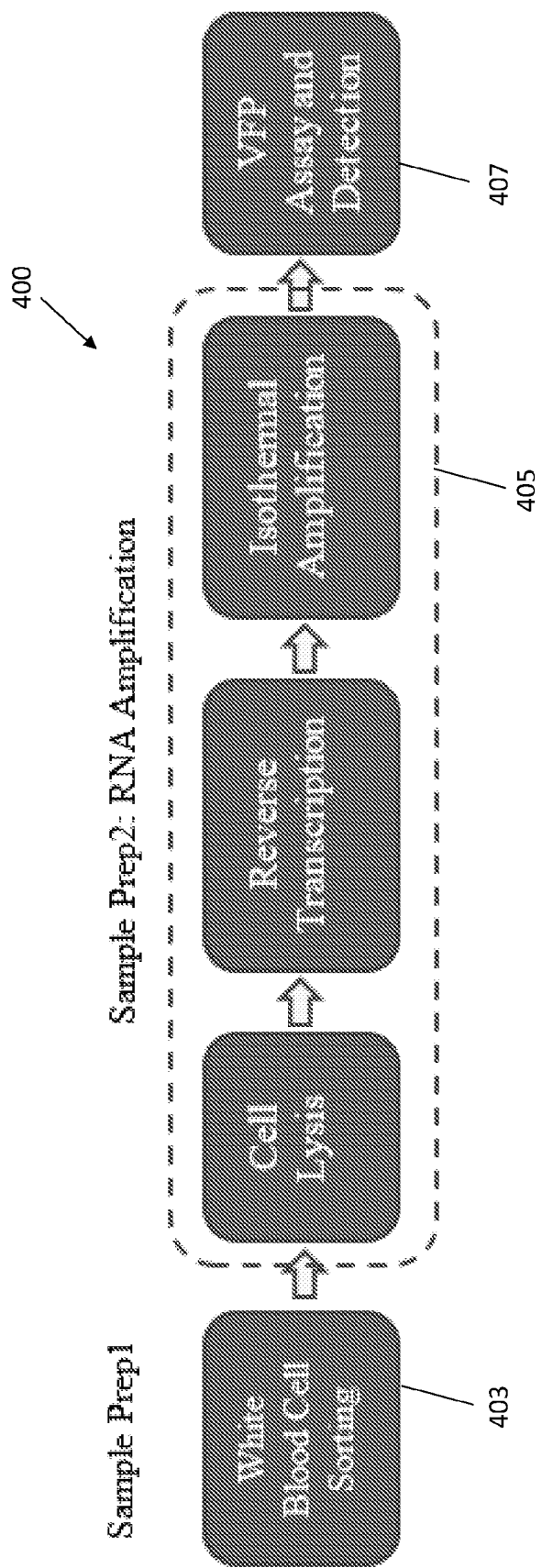
FIG. 37 shows a flow diagram of operation of a user-centered VFP platform with automated sample preparation for nucleic acid biomarker detection for space missions.

To address the above-mentioned conditions, we design a user-centered VFP platform with automated sample preparation for nucleic acid biomarker detection for space missions. The nucleic acid VFP platform has a modular plug-and-play design to minimize the need of astronaut intervention. FIG. 37 shows a process 400 flow diagram of operation of the platform. It mainly comprises three modules, i.e. Block 403: Sample Prep1—white blood cell sorting, Block 405: Sample Prep2—RNA amplification (including cell lysis, mRNA reverse transcription, cDNA isothermal amplification), and Block 407: the final VFP assay and detection.

Figure 38:
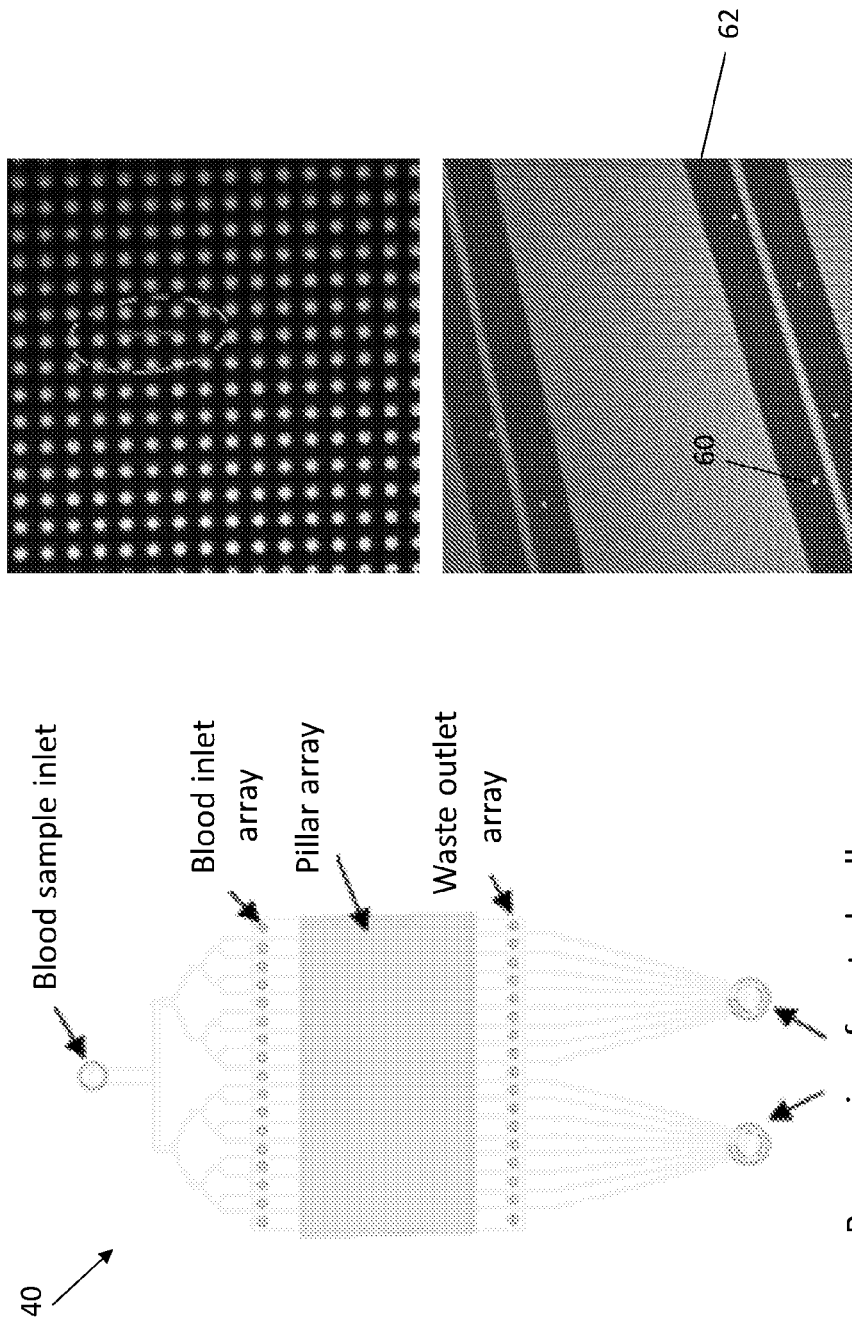
FIG. 38 illustrates a layout of a DLD chip and fluorescent images of white blood cells being sorted into designated channels.

Block 403, Sample Prep1—White Blood Cell Sorting Module: Current gene expression biodosimetry biomarkers are detected from lymphocytes in blood because it is a systemic bodily fluid that can be collected with minimal invasiveness. To detect gene expression from white blood cells, red blood cells usually need to be removed to reduce the interference from their large amount of RNA background. Traditionally, this is done by Ficoll-Paque density gradient separation. However, this process requires multiple manual handling and is difficulty to automate. To overcome this issue, a white blood cell sorting microfluidic chip based on deterministic lateral displacement (DLD) is used, where cells with different sizes flow through a micro-post array with columns of the array tilted slightly to the cell stream and those larger than a "critical size" defined by the array are bumped out of (and separated from) the original stream]. We have demonstrated the DLD chip for gene expression applications and integrate it into the VFP platform as the initial step of sample preparation. FIG. 38 shows layout of a DLD chip 40 and fluorescent images of white blood cells 60 being sorted into designated channels 62.

Block 405/Sample Prep2—RNA Amplification Module: The RNA amplification module provides white blood cell lysis, mRNA reverse transcription and isothermal DNA amplification.

RNA can be prepared through different processes for detection, by organic extraction, filter based spin basket, magnetic particles or direct lysis. The direct lysis method: (i) has the highest potential for accurate RNA representation, (ii) it can work with small samples, and (iii) it is amenable for simple automation. Direct lysis assay chemistry can be used for VFP gene expression detection and implemented through a microfluidic cartridge.

The extracted mRNA needs to be reverse transcribed to cDNA and amplified for VFP detection. Traditionally, cDNAs are amplified through a cyclic heating/cooling process by polymerase chain reaction (PCR). However, several isothermal amplification processes have been reported recently for simple automation and POC application, such as loop mediated isothermal amplification (LAMP), rolling circle amplification (RCA) and nucleic acid sequence based amplification (NASBA) etc. A recombinase polymerase amplification (RPA) process can be adopted that overcomes the drawbacks of other isothermal amplifications. It is also possible to integrate the reverse transcription process together with the amplification process. Commercial kits are available for gold nanoparticle 12 labeled reagents for lateral flow test, which can be adopted directly for VFP assay and detection. A microfluidic cartridge controlled by a microprocess controller is designed to automate the reverse transcription and amplification process for VFP detection.

Figure 36:
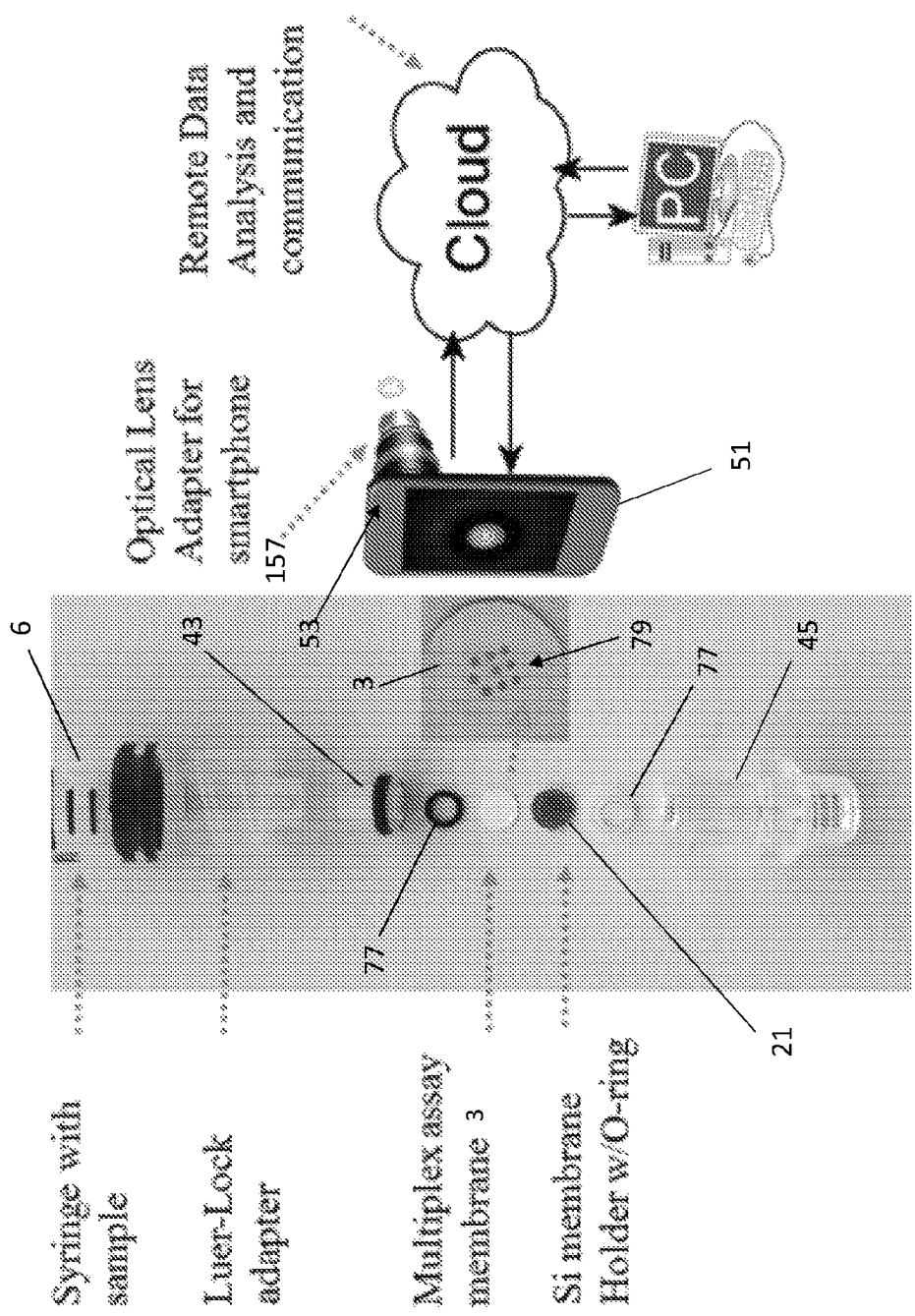
FIG. 36 is an illustration of a Vertical Flow Paper-based Platform (VFP) for assessing expression level of radiation dosimetry genes from PBMCs after irradiation.

Block 407/VFP Assay and Detection Module: This module comprises main features of current antigen 13 detection VFP platform of any of the devices described herein, including a syringe 6 cartridge for sample processing, and a reader for detection and data analysis. The main detection membrane 3 ishoused inside a membrane holder 29. The membrane holder 29 can be attached to the syringe 6 cartridge so that the amplified DNA sample can be pushed through the membrane 3 for target capture by capture agent(s) 19. Then the membrane holder 29 can be detached and mounted to a reader for array scanning and data analysis. FIG. 36 shows a current design of a spring loaded powerless syringe 6 cartridge for easy fluid handling, with a zoomed in view of the current design of a miniature membrane holder 29 attached to a smartphone 51 adapter 157 for data acquisition. These elements will be reconfigured to interface with upstream sample preparation modules (e.g., blocks 403 and/or 405).

Overall Platform Design: Finally, the Sample Prep and VFP modules (blocks 403, 405, and 407) are integrated together through human-centered cartridge design. This serves the human systems integration to ensure operational relevance to optimize space mission success and preserve human health. Design activities are aimed at emphasizing unequivocal value of the product platform to the NASA customer through system and crew factors, i.e. astronaut crew and space medicine team, and for the broader purpose of human spaceflight operations (i.e. clinical space medicine, expedition support).

Figure 39:
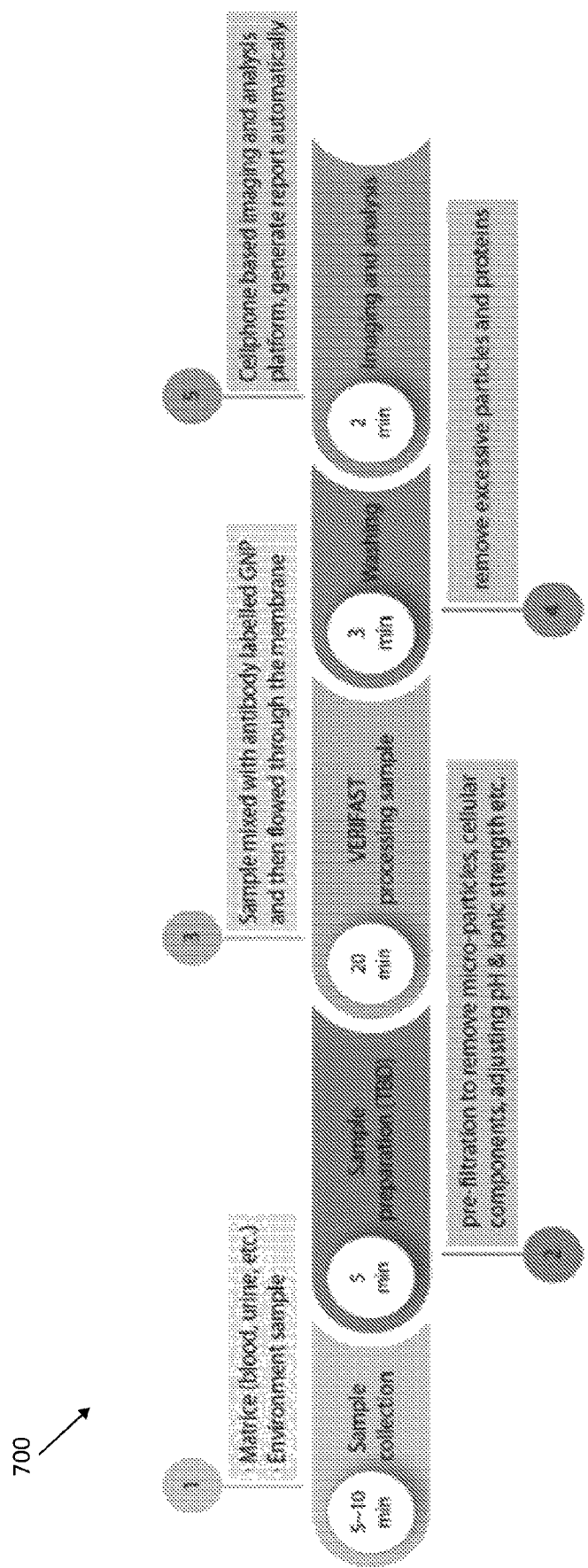
FIG. 39 shows a process flow of a human-centric cartridge design integrated into a modular automated sample preparation and monitoring system.

Once aboard the space-based platform (e.g., currently the International Space Station (ISS), but relevant to other non-Earth outposts are orbital habitats), researchers are able to monitor their experimental data daily with planned upgrades to near real-time capability. This high throughput, reconfigurable and automated architecture allows for scalable and affordable use of microgravity. FIG. 39 shows a process workflow 700 of a human-centric cartridge design integrated into a modular automated sample preparation and monitoring system. The operational constrains are followed during design, such as the storage temperatures during each stage of space mission, power requirement, telemetry rate etc. Design includes internal electronics for control of fluid flow 23 and filtering, per specifications. Suitable image analysis software is used in the system, to ensure relevant data gathering and validation.

A VFP platform design, including sample preparations for gene expression biomarker detection that can operate in microgravity environment for spaceflight health monitoring using a simple fingerprick, which is integrated into an automated sample preparation, processing, and monitoring system of workflow 700 including disposable cartridges and appropriate sample port that is ground approved for space mission is thus provided.

Example 9: Development of Vertical Flow Paper-Based Immunoassay (VPI) Diagnostic System for Multiplex Pathogens Detection This example provides a Vertical Integrated Flow Assay System Technology ("VERIFAST") for Multiplex Pathogens Detection. The VERIFAST is a rapid (<30 min) point-of-need diagnostics device 1 for use at multiple echelons of care and in the field.

An initial feasibility study will demonstrate the performance of the proposed biomarkers panel and assay kits for the integrated vertical flow immunoassay platform of the disclosed device 1. The next stage of VERIFAST™ will be to define a detailed user requirement that will satisfy FDA devices guidelines. Areas of requirements will include each of the constituent parts of the multiplex biomarkers panel and protocol, including sample preparation, stabilization/transportation, preparation, quantification/detection, and interpretation of the multiplex array images, and their incorporation into a fully integrated automated point-of-need (PON) system. The outcome will be a list of requirements from which the deliverables can be checked and modified appropriately.

Key processes to integrate into the system for the VERIFAST system are: Enhancements to the sample preparation for clinical (e.g. blood, urine) and non-clinical samples (e.g. growth media and soil suspension matrices); Optimization of the multiplex signatures and assay chemistries (i.e. 5 pathogens; enhanced optical properties of nanoparticles 12); Upgrade of the optical detection module from the current benchtop scanning system to the compact smartphone 51 module for point-of-need configuration; Modified and optimized data interpretation software for the proper analysis of multiplex biomarkers from serum and environmental or lab-grown samples.

The sample preparation cartridge and instrumentation hardware are designed, built and tested (iteratively) to optimize the process to provide as high a success rate as possible. Following successful attainment of appropriate data protection and securitization of data, these expert systems can be made available through a gateway to an external server. This task is coordinated to ensure compatibility with specified mobile systems. The packaging of system-ready sample preparation cartridges is delivered for subsequent evaluation.

A main objective is to deliver a paper-based microfluidic Vertical Flow Integrated Assay Technology platform (VERIFAST), in a portable, rapid multiplex bio-fluid preparation, processing, and 'sample-to-answer' analysis system designed for rapid detection (<30 min) and multiplexed identification of biological features in human clinical fluids or environmental samples. The technical aspects include: Bioassay design and integration. We design the workflow integration for the microfluidic device including sample collection, sample volume processing, buffer compositions, sample run time, and result analysis; Evaluate and validate the VERIFAST assay for each of the biomarkers with respect to standard LFI assays. The VERIFAST system is compared to the relevant LFI that has either previously been developed or is in the process of being developed. This will indicate whether the VERIFAST can achieve improved analytical sensitivity over the LFI, especially in the proposed multiplexing configuration; Design, assemble and validate the overall VERIFAST platform. Through an iterative process, the VERIFAST assay is optimized for analytical sensitivity (e.g. limit of detection, LOD); Translate the VERIFAST platform system to pre-clinical studies; Product development and preparation for FDA approval.

Product Description: Below is a summary of the specification of the current VFI system of the disclosed device 1 and its next generation (VERIFAST™)

TABLE

Product Description

| Module | VERIFAST System Features |
|---|---|
| Sample Collection | Standard sample collection method Compatible with urine, serum, plasma; adaptable to soil preparation |
| Sample volume | 200 μL to 5 mL and above |
| Bio-Assay | Protein assay: Burkholderia pseudomallei, Burkholderia mallei, Bacillus anthracis, Francisella tularensis and Yersinia pestis |
| Test time | 30 min |
| VERIFAST hardware interface and analysis Software | VERIFAST: a fully disposable device with the testing membrane and other functional hardware (membrane support, liquid sealing etc.) pre-assembled in a sealed package Testing kit: including the blocking buffer, washing buffer and dilution buffer (optional) Imaging probe: an optical system that connects the VERIFAST to the cellphone camera with desired magnification and focal distance VERIFAST analysis app: an iOS or Android based App that can image the membrane with desired specs and run analysis to examine the signals from each spot and generate a report automatically for reference |

FIG. 36 is an Illustration of the VERIFAST Development for Point-of-Need Concept Relevant for the sample collection module include: The collection device of module must be capable of reliably collecting a range of volumes from at least 200 μL to 5 mL of whole blood; or being adapted to prepare soil suspension for media culture; The collection device of module must be compatible with use in remote environment by a relatively unskilled individual given appropriate training; The collection device of module must be capable of reliably delivering the collected bio-sample to the next sub-systems of the multiplex assay detection of the VERIFAST system platform; The collection device of module must have a suitable method for tracking and transferring the user tracking information to the VERIFAST system platform to ensure custody chain of information.

Relevant aspects for the VFI membrane include: The membrane substrate has good mechanical properties for accommodating various flow 23 rate regimes and it has controlled pore sizes compatible for optimizing all necessary fluidic properties suitable for a miniaturized configuration; the membrane can be preloaded with all required reagents; the membrane can be packaged so as to have a minimum shelf life of 6 months with 3 years being preferable.

Relevant aspects for a multiplex assay include: The assay is capable of discriminating, five pathogens biomarkers of biological fluids collected at a point-of-need in variable volumes from small (e.g. <200 μL) to large (>5 mL) quantities; The assay can have an analytical range that is linear across two orders of logarithmic scale, preferably <nanomolar target concentration depending on the input specimen; Analytical performance requirements for the assay (accuracy and precision) are derived from the final multiplex biomarkers algorithm, and are designed to allow reproducible diagnostics prior or near a therapeutic decision point; the assay is capable of being read by human eye or using an optical imaging system readily available on a mobile smartphone device 51 or the like; the assay is able to start with an input of whole blood or urine and determine the biological exposure of an individual to at least a pathogen from multiple targeted biomarkers whose antibody couplings are specifically producing scattering signals from a nanoparticle 12 label which can be detected by an imaging sensor (e.g. smartphone 51 camera 53)

TABLE

| | Instrument Characteristics |
|---|---|
| Cycle Time | The instrument shall perform the assay from biospecimen collection to multiplex analysis in less than 30 min |
| Device | The VERIFAST device shall automate the running of the entire sample processing and assay, control all required functions, perform detection analysis, data collection and data interpretation without any user intervention post sample and reagents kit loading |
| Detection | The device shall be capable of interfacing with a mobile appliance for detecting antibodies reactions directly through light scattering imaging |
| Regulatory | The VERIFAST device shall be compatible with FDA class II regulation |
| Field Portable | The device shall be of a portable size and weight, allowing point-of-need operations and mobility |
| Networking | The device shall have networking capabilities compatible with standard and specialized communications systems and protocols, per specification |
| Data Processing | The device shall be capable of performing all data processing requirements and deliver a diagnostics test while functioning in standalone or networked modes |
| Power | The device shall run without external power or be compatible with battery-pack remote operations |
| Installation | The device shall be capable of being transported to new locations without any setup requirements aside from connecting to an electronic appliance like a smartphone (or other equivalent handheld reader if applicable) |
| Patient Tracking | The device shall be equipped with suitable patient/sample identification and/or tracking hardware and database (if applicable) |
| Duty | The device shall be capable of running 24 h/day with no required maintenance |

The VERIFAST platform enables the operator to load a plastic syringe 6 or equivalent cartridge module containing patient samples individually. The device 1 will process in four steps, performing the multiplex pathogens assay, recording the biomarkers interactions and performing the analysis required to provide a diagnostic result: 1. Biofluid filtering and pre-processing (e.g. serum and plasma separation); 2. Ab labeling and hybridization reaction with antigens 13 using multiplex assay; 3. Imaging detection (e.g. nanoparticles 12 scattering); 4. Numerical processing of biomarkers detection to determine result.

Results are recorded in a database on the instrument and provided to the operator in a format to be agreed upon specific requirements and applications, for example in a mobile setting or field operational scenario. The operator can dispose of the processed devices 1.

The VERIFAST technology platform is summarized as a multiplex pathogen bio-markers panel system which is broken into several key subsystems previously described above with reference to the various embodiments of the disclosed device 1.

The VERIFAST system platform integrates advances in several interdisciplinary fields to substantially improve and change the capability to perform immunoassay testing with multiple biomarkers of at least five bacterial pathogens in a remote setting by providing a new self-contained integrated paper-based microfluidic vertical flow device 1 diagnostic platform system. Some singleplex Lateral Flow Immonoassays (LFI) already exist for bacterial detection and are in use for other applications. However, we know of no multiplex Tier 1 Pathogens-based system that are currently used in a fully automated miniaturized point-of-need format suitable for operating by non-expert users and without power requirement, or multiple steps manual preparation beyond the sample loading into a self-contained vertical flow device pre-loaded with all necessary assay reagents, onboard fluidic management, and multiplex detection, either by direct visualization or imaging using standard mobile electronic appliances (e.g. smartphone 51 camera 53). In this example, we build upon the combined knowledge and interdisciplinary knowledge and outline the necessary validation required to ready this integrated technology for use in mobile settings. What distinguishes the VERIFAST platform is that not only is the detection highly sensitive and specific, but also analysis for characterization of multiplex biological signals is performed simultaneously rather than in a series of independent assays. The integrated system approach of this example leads to a fully handheld "sample-to-answer" analysis approach that is based on the integration of existing sub-components, both technological and scientific.

This device and methods can focus on current bacterial biomarkers of critical pathogens in biological fluids, although the assays can also be designed for dual use with other non-clinical targets. The detection biomarkers used in this study are validated for specificity by screening them on multiple systems across diverse platform technologies. With the VERIFAST system platform, the ability to assess the biological responses to pathogens exposure or not, and rapidly in a readily available fluids or environmental samples, represents a significant leap forward in effectively protecting the field operators engaged in active missions.

FIG. 39 is an illustration of the assay workflow 700 for this example, e.g., the VERIFAST Automated Assay Workflow.

The solution presented in this example shifts from the current paradigm of clinical laboratories testing capabilities to a comprehensive handheld diagnostics capacity of dual testing of clinical and environmental samples in field forward austere environments with limited resources. Such a transformation is only now possible due to advances in molecular assay technology, the development and validation of highly sensitive and specific biomarkers for bacterial pathogens and the advancement of multiplex vertical flow immunoassay technology. The disclosed VERIFAST system platform integrates these advancements into a medical defense solution to allow for the rapid identification of pathogens in biofluids at their earliest possible exposure time points. The transfer of existing technologies from a research lab to a field forward setting is not a simple endeavor and this translational work is the primary focus of this example. For instance, in a research laboratory the focus is often on assays that evaluate a single specific target, and these assays are often employed one at a time. In contrast, in a point-of-need setting the ability to detect quickly a broad spectrum of targets is the main objective because many of these biological perturbations can exhibit similar symptoms. The key innovation of our approach is to combine these existing technologies for point-of-need, paper-based microfluidic vertical flow immunoassay currently undergoing extensive platform validation and rapid prototyping, with reagents kits that are extensively validated into a robust diagnostic platform to simultaneously test for multiple biological responses to Tier 1 pathogens exposure for field forward application by personnel operating in austere environments.

The AuCoin laboratory specializes in biomarker discovery and development of immunoassays for infectious diseases. The team developed multiple platforms including In Vivo Microbial Antigen Discovery or "InMAD" for the identification of shed/secreted microbial antigens 13 within patient samples (Yuan, Fales, et al. 2012; Yuan, Khoury, 2012). This has led to the development and optimization of multiple assay for direct detection of microbial antigens 13 (Yuan, Fales, et al. 2012; Wang, et al., 2016; Indrasekara, Meyers, et al., 2014; Liu et al., 2015; Indrasekara, Johnson, et al., 2018). Our assay development workflow includes (i) identifying multiple shed microbial biomarkers in patient samples, (ii) isolating large panels of well-characterized capture agent 19 mAbs to each target (producing >20 mAbs to each target ensures superior assay performance), (iii) down selecting mAbs and optimizing antigen-capture ELISA for biomarker detection and (iv) transferring the assay to different diagnostic formats (e.g. LFI, VFI, etc.).

The program has been focused on developing LFIs for a number of pathogens including, but not limited to all of the Tier I bacterial select agents classified by the Department of Health and Human Services. These pathogens include *Bacillus anthracis* (anthrax), *Burkholderia pseudomallei* (melioidosis), *Burkholderia mallei* (glanders), *Francisella tularensis* (tularemia) and *Yersinia pestis* (plague). These are the infectious disease that are studied in this current example. The table below summarizes the biomarkers for the five pathogens and current status of each of the singleplex LFI assays. We continue to use the same biomarkers for the VERIFAST system. The results are compared with corresponding LFIs. Currently, the LFI developed for *B. pseudomallei* is anticipated to identify *B. mallei* as well, this is due to the conserved capsular polysaccharide (CPS) produced by each species. The *B. anthracis* and *B. pseudomallei* LFIs are developed in collaboration with InBios International (Seattle, WA) and have been shown to achieve a limit of detection (LOD) of 1 ng/ml. Both of these assays are in-hand and are currently being evaluated in the pre-clinical setting. LFI for *F. tularensis* is in progress, and the biomarkers and lead mAbs are available for VFI system evaluation. The biomarkers for *Y. pestis* have been identified and mAbs are currently being purified. Monoclonal antibody production, growth of BSL3 pathogens, purification of bacterial targets, and development of prototype assays is ongoing at AuCoin laboratory.

TABLE

| LFI Development: | | | | |
|---|---|---|---|---|
| Pathogen | Target (Biomarker) | Lead Antibody | LFI Prototype | TRL* |
| B. anthracis | Capsule (PGA) | mAb 8B10 | Yes | 6 |
| B. pseudomallet | Capsule (CPS) | mAb 4C4 | Yes | 5 |
| B. mallet | Capsule (CPS) | mAb 4C4 | Yes | 4 |
| Y. pestis | LcrV and F1 | Multiple | Yes | 4 |
| F. tularensis | Lipopolysaccharide (LPS) | mAb 1A4 | In progress | 4 |

*Technology Readiness Level

Figures 40A, 40B:
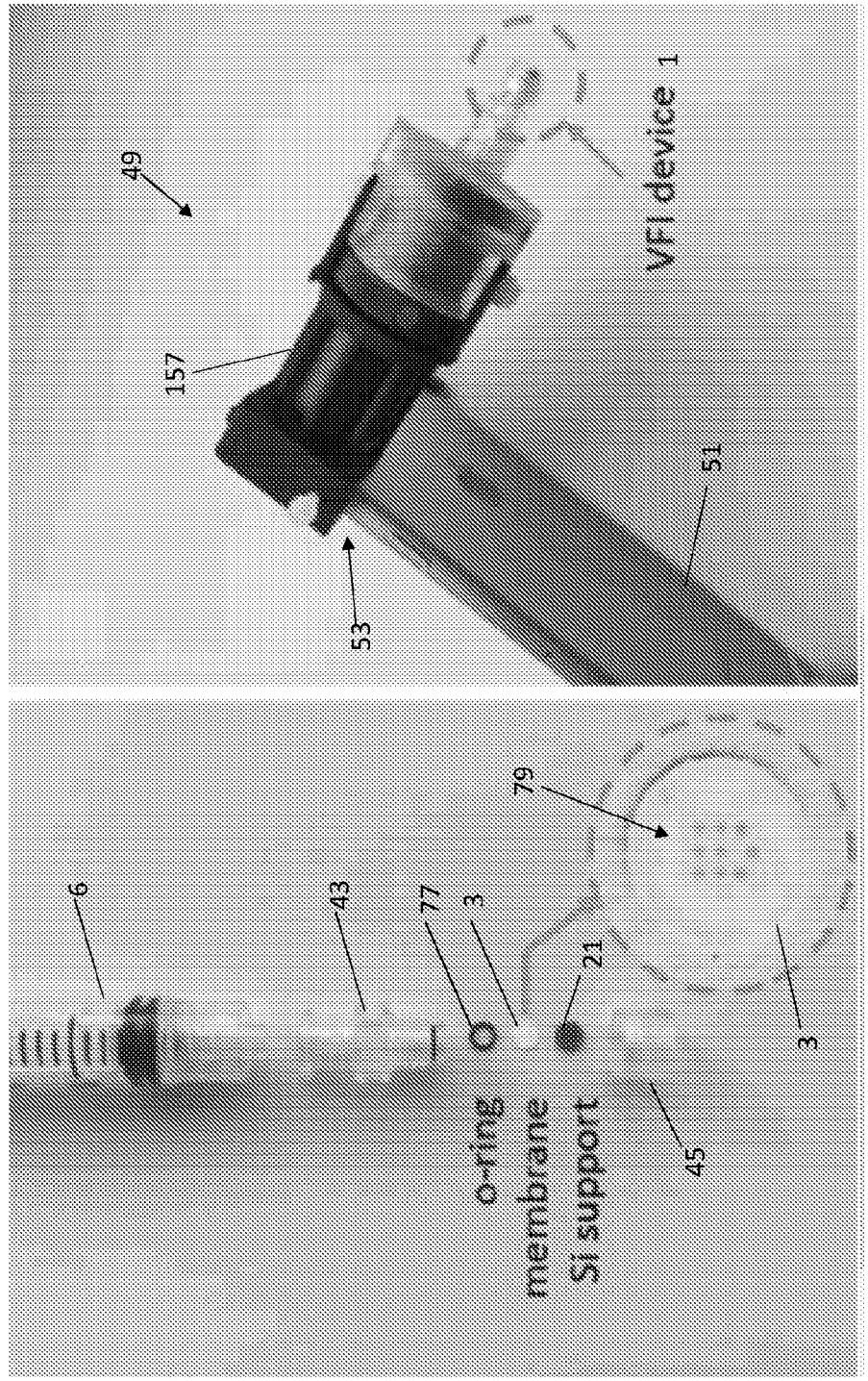
FIGS. 40A and 40B shows the design of the paper based VFI device and a prototype imaging probe used for scanning the VFI membrane.

FIG. 40A shows a design of the paper based VFI device 1 (Cheng, et al., 2019) according to this example. The device has a nitrocellulose membrane 3 based vertical flow immunoassay (VFI) diagnostic device 1. The insert of FIG. 40A is an example membrane 3 showing positive signals from the microarray of spots 79. The prototype of FIG. 40A includes a nitrocellulose membrane 3 (e.g. diameter of 3.5 mm) with spotted antibody capture agent 79 array, a silicon membrane support 21, and an o-ring 77 sitting inside a polycarbonate housing (e.g., holder 29). The VFI device 1 uses a standard Luer-lock fitting to connect to the sample syringe 6. After the sample run is completed, the Luer-lock can be conveniently disconnected with the sample syringe 6 and re-connected to the smartphone 51 camera 53 imaging probe, as shown in the prototyped imaging detection system 49 module design is shown in FIG. 40B. The setup shown in FIG. 40B is an example of an imaging detection system 59 module used to scan the VFI membrane 3 with smartphone 51 camera 53. In the process, the membrane 3 stays inside the VFI device 1, which minimizes the users' exposure to the potentially bio-hazard samples.

The insert of FIG. 40A is a membrane 3 example showing positive signals from the microarray of spots 79. The microarray spots 79 are deposited with capture agent 19 antibodies targeting different biomarkers of the pathogens panel. The microarray membrane 3 is fabricated with a BioDot™ micro-solenoid dispenser with droplet size of 1 nanoliter, which yields a spot 79 size of ~220 μm on the membrane 3. Quality of the VFI membrane 3, including spot 79 size, spot 79 spatial resolution, and number of multiplexing can be further improved with advanced micro piezodispensing system with in-line camera feedback module.

The Si support 21 is a circular silicon disk with flow through holes (diameter of 150 μm) fabricated using deep RIE methods. It provides mechanical support to the membrane 3 against the liquid flow 23. Silicon support 21 has a higher Young's modulus than commercially available stainless steel support, and thus less susceptible to deformation under flow 23 pressure. It significantly improves the signal uniformity across the spot 79 microarray on the membrane 3.

As a significant part of the ongoing effort to optimize the vertical flow diagnostic platform, multiple system parameters are investigated both theoretically and experimentally. The disclosed VFI device 1 platform is detecting the bio-threat pathogens based on sandwich immunoassay. There are two critical dimensionless numbers in the VFI system of the disclosed device 1. One is the Damköhler numbers ($D_a$), which characterizes the relation between adsorption rate and transport rate. The second one is the Péclet number ($P_e$), which is the ratio between convection rate and diffusion rate. To capture target antigen 13 with low concentration using capture agent(s) 19, two conditions are desired: (1) Efficient capture assay ($D_a \gg 1$), in which the rate of the antigen 13 binding to the capture agent 19 antibody is faster than the rate of antigen 13 molecules transport to the pore wall in membrane 3; (2) Non-diffusion-limited assay ($P_e < 1$), allows for all delivered antigens 13 to diffuse to the membrane 3 pore wall before they are convected through the sensing area 81.

Based on these two requirements, the VFI design has high flow 23 speed and small membrane 3 pore size to improve the assay sensitivity.

The table below summarizes the factors investigated for the VFI system of the disclosed device 1 to determine their effect on the performance of the VFI system of the disclosed device 1. They can be divided into four groups, related to the sample, device, assay, and operation protocol respectively.

| Sample | Device |
|---|---|
| Sample type | Membrane size |
| Sample pH | Membrane material |
| Sample ionic strength | Supporting strength |
| Sample volume | |
| Assay | Operation |
| Capture antibody | Unit flow rate |
| Detection antibody | Test time |
| Colorimetric agent | Mixing time |
| | Dilution factor |

Some of the factors are found to be very significant, such as the membrane 3 material pore size and sample flow 23 rate. Experiment results indicate that nitrocellulose membrane 3 with smaller nanometer pore size provide the best sensitivity with the current four bio-threat assays implemented on the VFI platform of the disclosed device 1. The higher the unit flow rate is, the more sample is delivered to the sensing area 81 in a constant time, and the better detection sensitivity can be achieved. In contrast, some factors are less important, such as the density of the capture agent 19 antibody—as long as the spotted region of the membrane 3 is saturated, adding more capture agent 19 antibody to the same region does not further improve the sensitivity of the disclosed VFI device 1.

Performance of the VFI System in Detecting Bio-Threat Pathogens and Multiplex Detection.

The table below provides key specifications of a VFI device in comparison with the lateral flow immunoassay system using the same assay:

| | | Vertical flow assay (VFI) | | | Lateral flow assay (LFI) | | |
|---|---|---|---|---|---|---|---|
| Pathogen | Antigen | Sample volume | Assay time | Limit of detection | Sample volume | Assay time | Limit of detection |
| B. pseudomallei B. mallei | CPS | 5 mL | 30 min | 4 pg/mL | 100 µL | 15 min | 40 pg/mL |
| B. anthracis | PGA | | | | | | |
| Y. pestis | LcrV | | | 0.2 ng/ml | | | |
| F. tularensis | LPS | | | | | | |

Due to the larger flow through area 81 and integration of active pumping mechanism (e.g., pump 31), the VFI device 1 is capable of processing samples with larger volume, such as urine or environmental water soil suspension samples. The total test time of the disclosed VFI device 1 is longer than LFI, due to the longer sample preparation steps for larger sample volumes, but still under the 30 min benchmark. The sensitivity of the disclosed VFI device 1 is about 25 times more sensitive than a similar LFI configuration.

We perform experiments using the VFI platform of the disclosed device 1 to detect two targets simultaneously—CPS and PGA. The design of the multiplexing VFI membrane 3 is shown in FIGS. 10A-10C, with multiplexing VFI with CPS and PGA assay detected on the same membrane 3. FIG. 10B shows scanned images of the four membranes 3 with different samples (CPS−/PGA−, CPS+/PGA−, CPS−/PGA+, CPS+/P). The detection spot 79 microarray was divided into two parts. Half was coated with mAb 4C4 capture agent 19 targeting the CPS, and the other half was coated with mAb 8B10 capture agent 19 targeting the PGA. Four samples with different antigen 81 contents (CPS negative/PGA negative, 1 ng/mL CPS/PGA negative, CPS negative/1 ng/mL PGA, 1 ng/mL CPS/1 ng/mL PGA) were processed with the VFI membrane 3. FIG. 10B shows the scanned images of the four membranes 3. FIG. 10C shows the signal intensities from the four membranes 3. The detection spots 79 showed positive signals only when the corresponding antigen 81 existed in the sample. This experiment demonstrated that the VFI platform of the disclosed device 1 was able to detect multiple biothreat agents simultaneously. Unlike LFI, the detection spots 79 were spatially separate and independent from each other in the VFI system of the disclosed device 1, making the disclosed VFI device 1 especially suitable for large-scale multiplexing detection.

Figure 41:
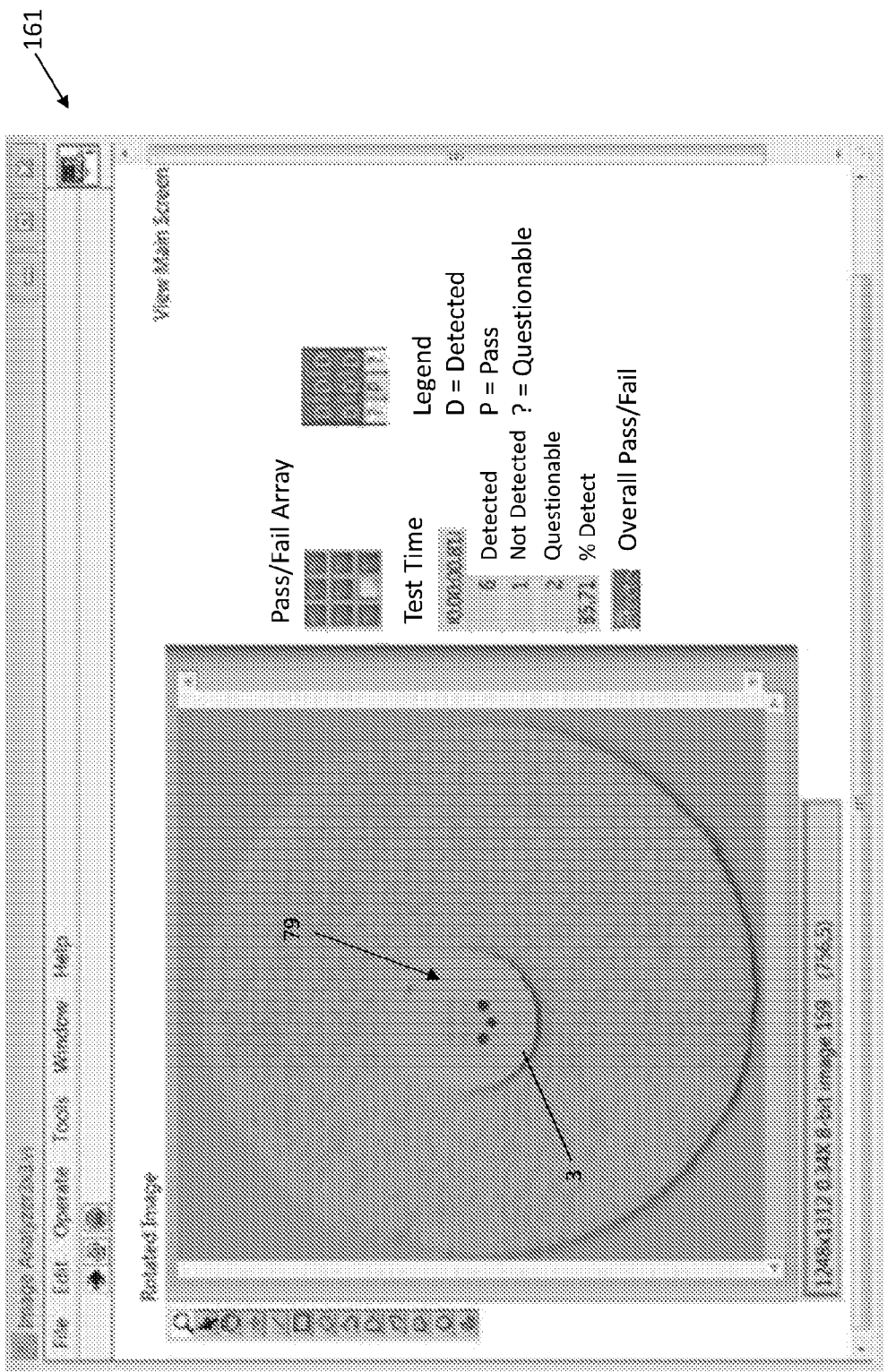
FIG. 41 shows the user interface of the current benchtop image analysis software.

FIG. 41 shows the user interface of the current benchtop image analysis software 161. The workflow of the software to analyze the miniVFI membrane has three major steps: 1) Identify and rotate the image using a pre-defined template; 2) Locate each spots 79 in the microarray. After identifying the template, an x/y two-axes coordinate is created in relative to the template. The coordinates of each spot 79 can be calculated based on the pitch distance and the scanning dpi; 3) Obtain the intensity from each spot 79 and its background; 4) Generate a diagnostic report (positive, negative, and questionable) for each spot 79, which can potentially for one type of biomarker.

We compared the results with manual methods using ImageJ. On the average, the difference was up to 15%. Considering that the signal intensity from the membrane has a variation of 10% itself, the results from the software is quite accurate. Note: the software 161 system has also been adapted to analyze LFI strips.

Among plasmonic nanoparticles, surfactant-free branched gold nanoparticles have exhibited exceptional properties as a nanoplatform for a wide variety of applications ranging from surface-enhanced optical sensing and imaging applications to photothermal treatment and photo-immunotherapy for cancer treatments. A surfactant- and capping agent-free route to synthesize gold nanoparticles with multiple sharp branches protruding from a spherical core has been introduced, which is referred to as "gold nanostars" (GNS) (Nuti, et al., 2011). The biocompatible, ligand-free surface chemistry of that requires no ligand exchange or extensive purification protocols, ease of direct surface functionalization, and superior surface area available (compared to spherical gold nanoparticles of the same diameters) for biomolecule loading are few major advantages offered by GNS in comparison to other types of gold nanoparticles (Jiang et al., 2011); Yuan, Weng, et al., 2011; Yuan, Khoury, et al., 2012; Yuan, Fales, et al., 2012; Wang, et al., 2016; Indrasekara, Meyers, et al., 2016; Liu, Ashton, et al., 2015; Indrasekara, Johnson, et al., 2018; Lenshof, et al., 2009; Kim, et al., 2017; Kuo, et al., 2015). In addition, GNS exhibit unique and extraordinary optical properties such as high scattering crosssection, plasmonenhanced absorption and geometry controlled plasmon absorption band tunability in the visible to near infrared spectral range (Nuti, et al., 2011; Gong, et al., 2013). Collectively, both chemical and optical properties of the GNS could provide a versatile platform for enhancing the optical detection performance of the application of the VERIFAST platform.

Figure 42:
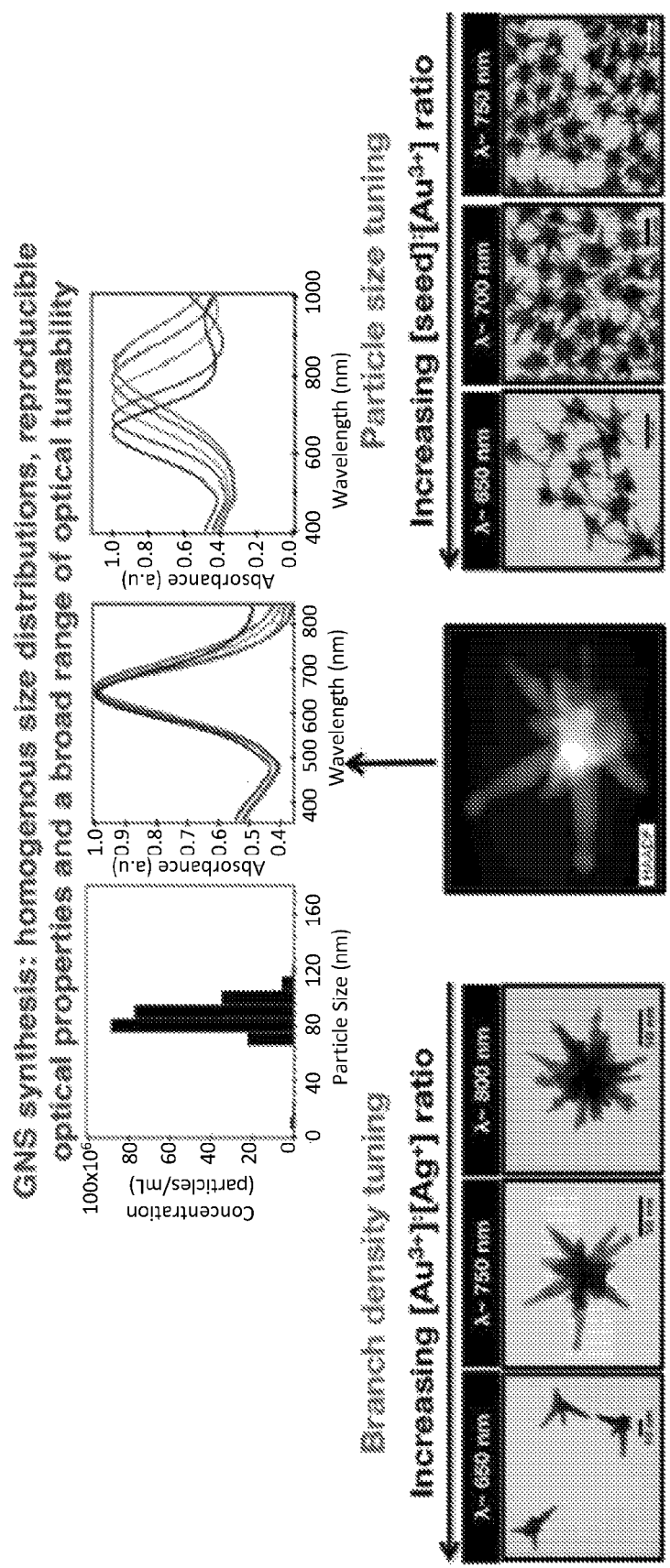
FIG. 42 shows transmission electron microscopy (TEM) images and absorption spectra showing the morphological and optical tuning of high quality GNS with high reproducibility using surfactant and capping agent-free seed mediated synthesis approach.

The effectiveness and reliability of nanoparticles in biomedical applications strongly rely on the consistency and reproducibility of physical, chemical, and optical properties of nanoparticles, which is mainly governed by their morphological features. Design parameters have been developed for the purpose-tailored manufacturing GNS in a reliable manner. There are equipped with optimized bottom-up synthesis protocols that improve reproducibility and homogeneity of GNS, and the modulation of their morphology, particularly the branch density, geometrical features of branches to obtain desired optical properties. Through systematic modulation of experimental parameters, GNS can be manufactured with branch densities ranging from 3-30 branches/particle, overall size from 30-200 nm, and optical absorption ranging from 530 nm-900 nm, as shown in FIG. 42 (Nuti, et al., 2011; Gong, et al., 2013). FIG. 42 shows transmission electron microscopy (TEM) images and absorption spectra showing the morphological and optical tuning of high quality GNS with high reproducibility using surfactant and capping agent-free seed mediated synthesis approach.

Biomarkers Panel Development: Purification and QC (Quality Control) Testing of mAbs Milligram quantities (≥500 mg) of each mAb capture agent 19 used in the VFI format are purified. The capture agent 19 mAbs are needed to develop prototype antigen 81 capture assays, LFIs, and VPIs. Existing hybridoma cell lines are cultured in Integra bioreactors (Integra systems) containing hybridoma growth media. Hybridoma supernatant fluid will be routinely collected and mAbs will be purified by affinity chromatography on protein-A columns. Fresh vials of hybridoma cell lines will be periodically woken up to ward off negative effects that can occur as a result of genetic drift and antibody subclass is routinely monitored. Each lot of capture agent 19 mAbs will undergo rigorous QC testing that includes enzyme-linked immunosorbent assay (ELISA), Western blot and surface plasmon resonance (SPR-/Biacore×100) assays to confirm capture agent 19 mAb performance. SPR assay allows for a thorough evaluation of mAb affinity that will include determination of kinetic binding data (on- and off-rates). Briefly, purified bacterial biomarkers are immobilized to a Biacore sensor chip. Samples (two-fold serial dilution of mAb ([333-5.2 nM]) are injected over the sensor surface for 60 s, after which the capture agent 19 mAb is allowed to passively dissociate. BIA evaluation software is used to determine the Ka (on-rate), Kd (off-rate) and $K_D$ (equilibrium dissociation constant or "affinity"). The dissociation constant ($K_D$) is determined using the steady-state model in BIA evaluation software.

The detection mAbs are conjugated to horseradish peroxidase (HRP) for ELISA, or GNP 12 and GNS for LFI and VPI using either passive absorption or functionalized surface chemistry. The conjugated reagents also undergo quantification and QC methods that include validation in ELISA or LFI format.

Purification of biomarkers and preparation of bacterial isolates: Milligram quantities (≥20 mgs) of each biomarker (bacterial antigen 81) are purified and used. This is required to test the performance of each of the prototype LFIs and VPIs that are developed. Purification of *B. pseudomallei* CPS, *B. anthracis* PGA and *F. tularensis* LPS will require growth of the pathogen (in some cases select agent exempt strains may be used). Biomarkers expressed by *Y. pestis* will be expressed by recombinant methods. In addition, heat or chemically inactivated whole cells and whole cell lysates of each bacterial pathogen will be produced. The work will be performed in a BSL3 laboratory. The recombinant proteins and bacterial preparations are used to determine the LOD (pg/ml and cfu/ml) of the VFI for each biomarker.

Prototype singleplex LFI development: Prototype singleplex LFIs are produced and used to compare with corresponding VFIs. The goal for the VFI is to achieve at least a 10-fold improvement in LOD. Prototype LFIs for *B. anthracis*, *B. pseudomallei* and *B. mallei* are currently in-hand. Prototype LFIs for *F. tularensis* and *Y. pestis* using biomarkers LPS, LcrV and F1 are currently being produce for this this project. A BioDot 3050 will be used to fabricate the prototype LFIs. Each component and parameter of the LFI will be optimized based on traditional methodology, including the sample pad, sample volume, chase buffer, conjugate pad, mAb labeling, membrane, test line mAb, absorbent pad etc. Analytical sensitivity/limit of detection (LOD) will be determined for each prototype LFI assay. In addition, purified biomarkers and whole bacterial cells will be spiked into relevant sample matrices (e.g. blood, urine) and LOD will be determined. Performance results are compared to corresponding VPIs. Both LFIs membranes and VFI membranes 3 are imaged with the same image analysis algorithm.

Figures 43A, 43B:
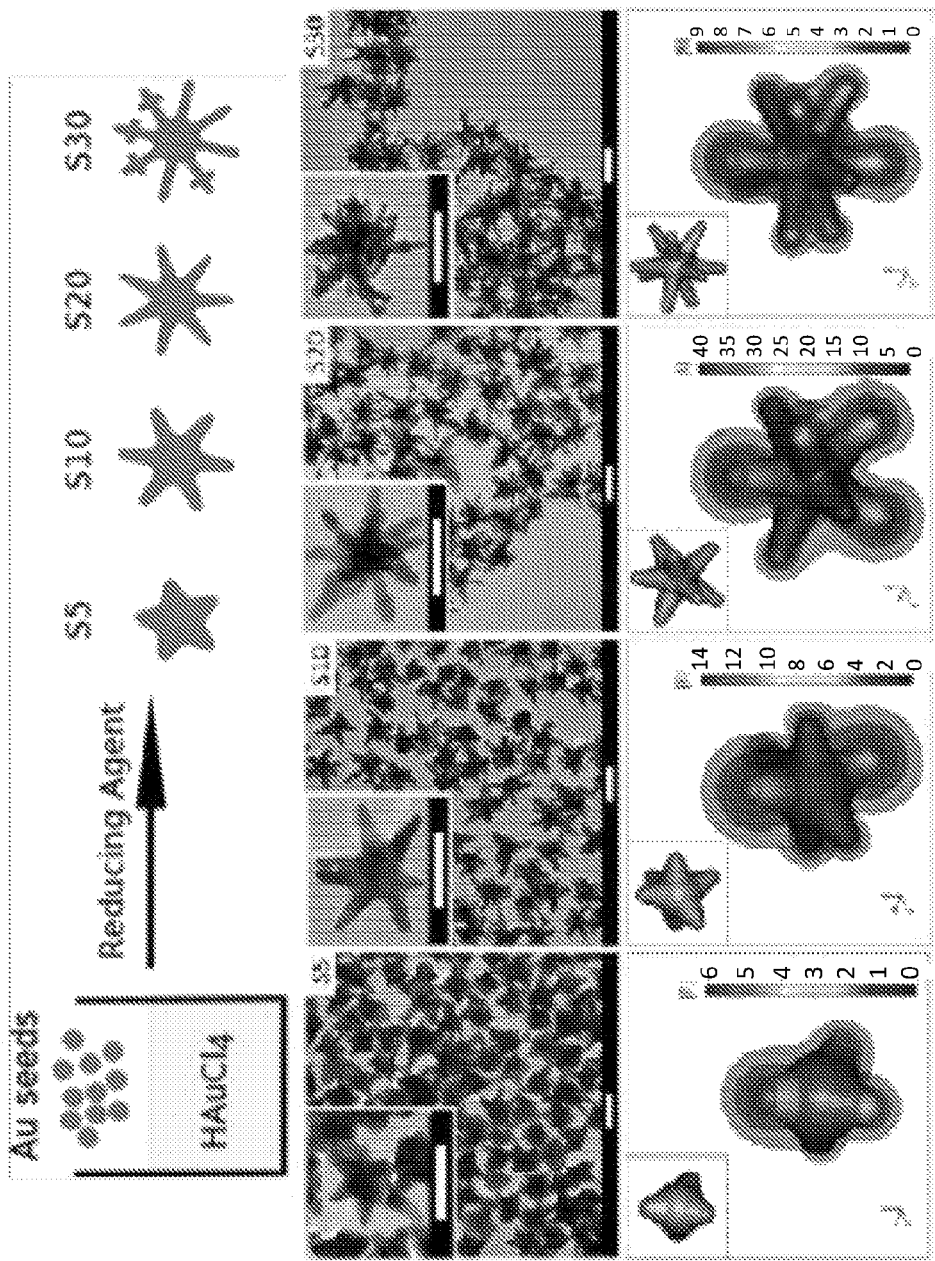
FIGS. 43A and 43B depict the experimental setup and results (TEM and 3D modeling images) of GNS formed under varying $AgNO_3$ concentrations.

Optical Detection Agent Development To optimize the optical properties of the VFI gold nanoparticles 12 labeling, the main task will focus on optimizing the fabrication processes. Synthesis of surfactant and capping agent-free GNS by a seed-mediated approach has been described (Yuan, Khoury, et al., 2012). This method of GNS synthesis is very simple in comparison to other nanoparticle syntheses that it only takes about 10 seconds to complete while allowing excellent fine tuning of the morphological features and the optical absorption (localized surface plasmon) position (Yuan, Khoury, et al., 2012; Yuan, Fales, et al., 2012; Wang, et al., 2016; Indrasekara, Meyers, et al., 2014; Liu, Ashton, et al., 2015; Indrasekara, Johnson, et al., 2018). Briefly, rapid sequential addition of AgNO$_3$ (shape directing agent) and ascorbic acid (reducing agent) to an acidic mixture of polycrystalline spherical gold nanoparticles (gold seeds) and gold chloride instantaneously yield GNS (FIGS. 43A and 43B). FIG. 43A is a schematic representation of the GNS synthesis. FIG. 43B are TEM and 3D modeling images (scale bar 50 nm) of GNS formed under varying AgNO$_3$ concentrations: (S5: 5 uM, S10: 10 uM, S20: 2 uM, S30: 30 uM). As-synthesized GNS can either be stored at 4° C. until further use or can be coated with polyethylene glycol to improve the colloidal stability and further functionalization purposes.

Ability to produce batches of gold nanoparticles 12 and coupling with Abs: When being used in the field, the disclosed VERIFAST device 1 processing comprises two major steps. The first step is to flow the sample through the membrane 3 so that the antigens 81 can bind to the capture agent 19 antibody. The second step is to flow a washing buffer through the membrane 3 to remove excessive nanoparticles 12 and non-specific loose-bond antigens 81. We can use a three-way valve system 163 (schematic of a proof of concept actuator is shown in FIG. 44A) to deliver the two liquids to the membrane 3. Compare with the current laboratory practice, in which users change syringe 6 to switch liquid, using a valve system 163 offers several benefits. It is easy to operate. It also eliminates the air bubble issues because of the pressure drop when switching syringes 6. It makes a liquid closed system to reduce the user's exposure to the potentially hazardous samples. In our current laboratory setup, a syringe 6 pump 31 (uses 120V AC power supply) is used to push the liquids through the membrane 3 of the prototype device 1. Considering the limited power supply in the field, we propose to use alternative methods that do not require external power supply to actuate the liquids. FIG. 44B is a prototyped design using a gas syringe 4 to push liquid through the membrane 3. Our preliminary test of a 15-lb gas syringe 4 has shown the ability to flow reagents within the desired timeframe. A more miniaturized and simplified liquid actuation method will be integrated to the VERIFAST system platform.

Si membrane support 21 fabrication: Si membrane support 21 is an important component of the VFI device 1 that facilitate uniform signals across the membrane 3. Currently, it is fabricated by semiconductor microfabrication techniques. First, photolithography is used to pattern a resist layer on a double-side-polished Si wafer. Then the resist is thermally harden in an oven or on a hotplate to serve as a mask for deep reactive ion etching (DRIE) of the Si wafer to make anisotropic through-hole arrays in the substrate. Mask design, resist spinning, photolithography and resist baking may be done in a cleanroom. More supports 21 per Si wafer will lower the unit cost of the support 21, but it could also cause the wafer to break because more through-holes are etched in the wafer). Once the optimal design is reached, the support 21 fabrication will be scaled up for production of the prototyping devices 1.

Array Printing with Replicates on Miniaturized Membrane: FIGS. 45A-45C illustrate aspects of membrane 3 array printing for the present example. FIG. 45A illustrates the surface area 81 of the nitrocellulose membrane 3 in a VFI device 1 design ($\phi$=3.5 mm; the gray region of the membrane 3 is covered by the o-ring 77). The flow through region on the Si support 21 with etched through holes is within a circle of 2 mm diameter.

FIG. 45B is a design of the multiplex array of spots 79. Using micro-solenoid dispenser, the minimum droplet volume is 1 nanoliter, which yields a spot 79 size of 230 µm. We are able to fit up to 6 detection spots 79 inside the flow through area 81, only one for each antigen 81. However, in order to improve the accuracy and reliability of the test, duplicate or even triplicate spots 79 for each antigen 81 is desired. FIGS. 45C and 45D is a design of the multiplex microarray of spots 79 for five antigens 81 with duplicates and triplicates respectively. In order to fit in these extra detection spots 79 within our miniaturized membrane 3, the spot 79 size and pitch distance both need to be reduced. Based on the spot 79 size, we can calculate the desired droplet volume is about 450 picoliter. Current micro-solenoid dispenser is not capable of doing this picoliter dispensing. A piezo-dispenser is can achieve such small droplet size and improve the dispensing spatial resolution.

With a piezo liquid dispenser, different parameters are tested to achieve the desired spot 79 size and pitch distance. A protocol is developed for printing multiplexed cAb array on the center of the miniaturized membrane 3. A procedure for low volume production of the multiplexed cAb array membrane 3 is also developed. Briefly, multiple miniaturized membranes are cut from a large membrane 3 sheet by CO$_2$ laser, then the small membranes 3 are loaded into a rigid membrane holder for array printing. The membrane 3 holder can be fabricated by CNC machining of polycarbonate or other hard plastics. The rigidity of polycarbonate allows precise alignment of the dispenser to the small membranes 3.

Sample Preparation and Assay Optimization in Sample Matrices: Sample preparation is a significant part of any assay for real world applications. Sample preparation modules and protocols suitable for PON settings (e.g. in <5 min timeframe) for multiple sample matrices, such as plasma and urine, are desired. The quality of the prepared sample may be characterized to ensure minimal loss of antigen and similar assay analytical sensitivity to benchtop procedures.

Plasma extraction cartridge for blood: The selected biomarkers pathogens are bacterial antigens in patient's circulation system for rapid disease diagnosis (Nuti, et al., 2011). Plasma/serum are common samples for pathogens immunoassays. Traditional, plasma/serum are prepared by centrifugation of whole blood and collecting the cell-free supernatant. However, it is not realistic to use bulky, power-demanding centrifugation in a PON setting. A simple and rapid plasma/serum generation method is critically needed. Among blood components such as plasma and serum, the plasma can be faster due to the fact it does not require coagulation of the clotting factors, and is usually the choice for PON applications.

Figure 46A:
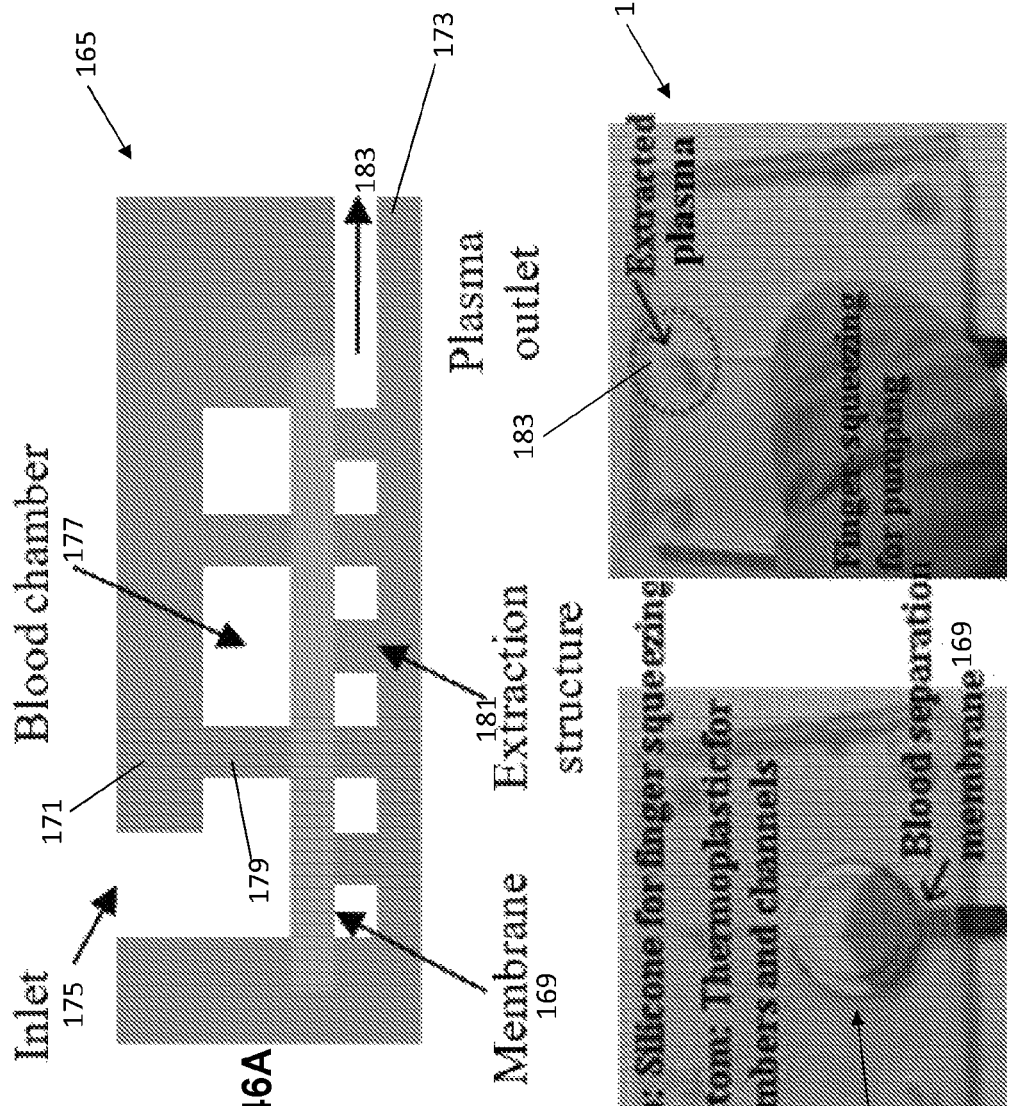
FIGS. 46A and 46B illustrate structural designs of a membrane-based plasma extraction device and a fabricated finger actuated plasma extractor.
Figure 46B:
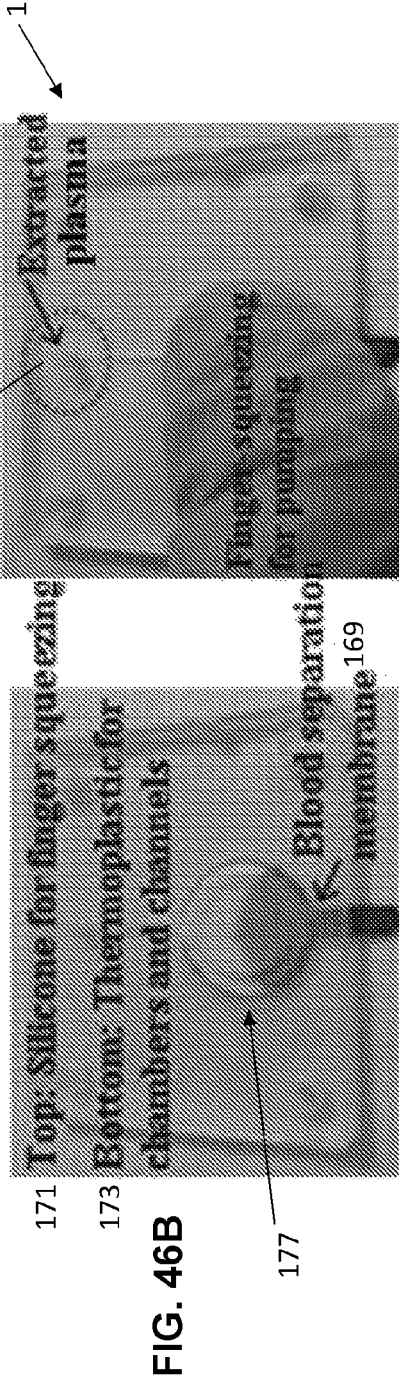

Due to the importance of plasma separation from whole blood, a number studies to achieve this have been reported, including using electric force (Jiang et al., 2011), acoustic force (Lenshof, et al., 2009), hydrodynamics (Kim et al., 2017), structured (Kuo, et al., 2015) or membrane filtration (Gong, et al., 2013). Among those techniques, membrane based filtration is the simplest form. In membrane based filtration, a commercial asymmetric polysulfone membrane (e.g. Vivid Plasma Separation Membrane, Pall) can be used to separate plasma from whole blood in as fast as 2 minutes. FIGS. 46A and 46B illustrates a basic structure of a membrane-based plasma extraction device 165 (FIG. 46A), and a fabricated finger actuated plasma extractor 167 (FIG. 46B). As shown in FIG. 46A, the membrane 169 is sandwiched before a top plate 171 and a bottom plate 173. The top plate 171 has an inlet 175 and a chamber 177 with supporting structures 179 to accommodate a blood sample. The bottom plate 173 has capillary structures 181 to extract plasma from the membrane 169. The plasma outlet 183 is another capillary structure that can pump out the extracted plasma.

The plasma separation extractor device (165, 167) have been fabricated and tested for biodosimetry. The knowledge gained can be leveraged for this task. The geometry and surface tensions of both top 171 and bottom 173-plates are investigated to achieve fast plasma extraction with minimal sample loss. Currently the membrane 169 has a limited whole blood capacity of <50 µL/cm$^2$. However, by scaling up the membrane area 81, handling of milliliter-scale blood in the field has been reported (Gong, et al., 2013). Further scaling up will be explored using 3D structures, e.g. stacked membranes 169. Moreover, cell sedimentation can be used to improve the speed and throughput of plasma extraction (Dimov, et al., 2011; Galligan, et al., 2015). For example, the basic structure of FIGS. 46A and 46B can be flipped upside down with a superhydrophobic blood chamber 177 at the bottom to improve the filter capacity by cell sedimentation. About 6.5×better membrane 169 capacity has been reported in a similar device (Liu, Liao, et al., 2016).

Other phenomena, such as pressure/vacuum and aggregation of red blood cells by isotonic dilution are also exploited to achieve the goal of extracting several milliliters of plasma in under ~5 min. Finally, the quality of the extraction plasma is characterized using spike recovery experiments for all five antigens 81 and compared to the benchtop procedures. Antigen 81 loss and change of analytical sensitivity are used to guide the optimization of the devices/protocols.

Urine is another common sample matrix for the VFI device and applications utilizing the VFI device. Different from blood sample, urine does not contain large amount of cells that need to be separated, and can be used directly with any of the disclosed VFI devices. However, unlike well-regulated plasma, urine has a large variable composition. The pH can vary between pH 4.5-8.0, osmolality from 50-1300 mOsm/kg, and urine specific gravity (USG) from 1.005-1.030 (Sviridov, et al., 2009). We do show that pH can affect the assay result, and ionic strength of <0.15 can increase the signal background. However, it was also reported that pH variation did not affect much detection of IL-6 in dog urine (Wood, et al., 2011). These effects will be further studied in human urine matrix (see Assay optimization in sample matrices). If needed, sample pH can be tested using pH strips and neutralized by HCl or NaOH. The ionic strength can be increased by adding NaCl.

Figure 47:
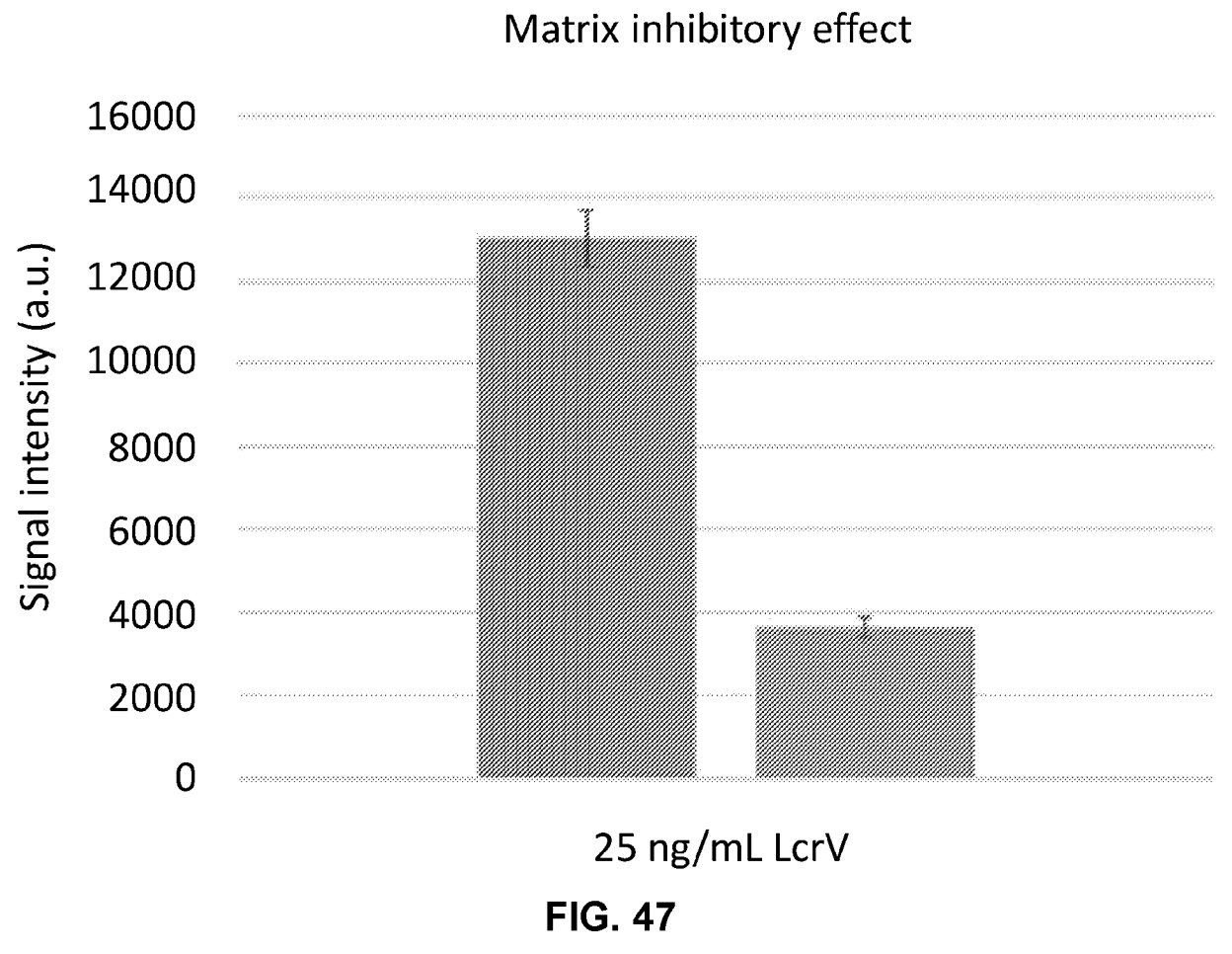

Plasma matrix optimization: It has been reported that plasma or serum can have strong inhibitory effects on antigens in immunoassays (Tate, et al., 2004; de Jager, et al., 2009). Spike and recovery experiments have shown the recovery rate in serum/plasma as low as 1% for certain antigens (Rosenberg-Hanson, et al., 2014). This is also observed in our VFI assay. FIG. 47 shows 25 ng/ml LcrV spiked into either buffer or serum. Plotted are signals of spiked 25 ng/mL LcrV in buffer and serum showing strong matrix inhibitory effect. The signal from serum sample is significantly less than that of buffer, even with a 4× higher GNP 12 concentration. However, dilution of plasma can partially alleviate this matrix inhibitory effect, and it is even suggested that slightly diluted sample is preferred than undiluted sample (Rosenberg-Hanson, et al., 2014). On the other hand, we also experienced membrane clogging when flowing undiluted serum sample through the smallest 0.1 µm nitrocellulose membrane. Both observations suggest a dilution of plasma samples for use in a VFI device. Nonetheless, smaller dilution factor is still preferred to avoid significant impact on assay sensitivity.

Due to the complexity of the matrix effects, we use Design of Experiment (DOE) for optimizing the VFI device 1 assays in plasma matrix. The critical parameters are: (1) plasma dilution factors; (2) membrane 3 pore size; (3) flow 23 speed; (4) GNP 12-dAb 10 concentration. First, a screening experiment is conducted to determine which of the four factors have a significant effect on the assay performance. The goal of this phase of experimentation is to eliminate design factors that are not having a meaningful impact on the response. The second experiment is a response surface-type design, where the true relationship between the design factors and their interactions is determined, to facilitate factor level optimization. Membrane blocking and suitable dilution buffer is also tested out separately beforehand. Furthermore, we previously dedicated 10 min for sample and gold nanoparticle 12-detection antibody 10 premixing, and the sample running time was another 10 min. In this example, we adopt a new approach to run the sample immediately after a short mixing time. This way, the sample running time is close to 20 min to double the sample passed through the sensor while still allowing liquid antigen-antibody reaction in solution at the same time. Each antigen is optimized individually because dilution of plasma samples is not linear and its effect on different antigens can vary from antigen to antigen.

As mentioned previously, human urine varies greatly in terms of pH (4.5-8.0), osmolality (0.05-1.3 Osm/kg), and USG 1.002-1.030 (Sviridov, et al., 2009; Cook, et al., 2000). It also contains a complex mixture of proteins and high amounts of urea, hippuric acid, etc. relative to plasma (Sviridov, et al., 2009). Inhibitory effect by urine matrix was also reported with some interesting observation that higher USG improved recovery of certain cytokine (Wood, et al., 2011). It would be a significant endeavor to fully study the effects of urine matrix on VFI. Accordingly, initial efforts study the effects of pH and ionic strength of urine sample. The pH and ionic strength of purchased urine sample is measured by pH meter (or pH strip) and conductivity meter. Then the pH and ionic strength can be adjusted by titration of acid/based and NaCl, and VFI can be performed for spiked antigens 81 under different pH, ionic strength conditions. Besides the pH and ionic strength, other relevant parameters such as dilution factor, membrane pore size, flow speed and GNP 12-dAb 10 concentration is also tested for assay optimization using similar DOE strategies to that in plasma matrix study. The USG and osmolality data is requested from the urine supplier and monitored during the project. The results influence the final sample preparation strategy for the VFI assay with the disclosed device 1.

Demonstration of Specimen Collection & Processing Modules: The experimental approach for the platform optimization will be sequential. Typically, a screening experiment will be conducted to determine which of the selected factors may have a significant effect on the assay performance. Then, a response surface-type design, where the true relationship between the design factors and their interactions can be determined, will be applied to facilitate factor level optimization. For the screening phase, a definitive screening design (DSD) will likely be used, as a DSD serves as an efficient screening design while also providing some attractive correlation properties and the ability to fit an adequate statistical model to find efficiencies in the second phase of experimentation. Depending on the outcome of the screening phase either an augmented DSD or a traditional response surface design such as a central composite design will be used.

Software is required to reliably analyze the images acquired from the VFI membranes 3. Existing software algorithms (CK Point #2.4) will examine the image, locate the test pattern, orient the image as required, then analyze the dot pattern to determine the values of the signal spots 79 compared to background values to determine if the target is detected. This software will monitor a selected Cloud location for any incoming images. When they arrive, the program opens the image, analyzes it, then moves it to a secure location for archiving, and reports the results. This configuration will be re-programmed for accommodating its conversion onto a mobile handheld device platform (e.g. smartphone 51 or equivalent electronic appliance) within the data security and communications protocols and requirements (e.g., as established by the defense community).

Application for Electronic Appliance (e.g. Smartphone 51)

Software can facilitate a reliable and easy-to-use end user interface. An app designed for the military approved smartphones 51 (e.g. Nett Warrior network with iPhone and Galaxy devices) can obtain the required 48-bit image of the test membrane 3 using the CCD phone 51 camera 53. The app can then send the image to a military-approved network location to be analyzed by the existing software, or the app can be written so that the analysis would occur directly on the smartphone 51, with the results being sent to the military approved network location.

The sample size for each of the primary five pathogens categories will be determined based on the table below, which shows the relationship between sample size and 95% confidence interval for a number of estimated sensitivities and specificities.

| Number of infected (non-infected) subjects required* | Estimated test sensitivity (or specificity)** | | | | | |
|---|---|---|---|---|---|---|
| | 50% | 60% | 70% | 80% | 90% | 95% |
| 50 | 13.9% | 13.6% | 12.7% | 11.1% | 8.3% | 6.0% |
| 100 | 9.8% | 9.6% | 9.0% | 7.8% | 5.9% | 4.3% |
| 150 | 8.0% | 7.8% | 7.3% | 6.4% | 4.8% | 3.5% |
| 200 | 6.9% | 6.8% | 6.4% | 5.5% | 4.2% | 3.0% |
| 500 | 4.4% | 4.3% | 4.0% | 3.5% | 2.6% | 1.9% |
| 1000 | 3.1% | 3.0% | 2.8% | 2.5% | 1.9% | 1.4% |

*As defined by the reference standard culture test
**95% confidence interval around the estimated sensitivity/specificity (+/− value in table)

The goal of field testing is to precisely establish the performance metric of the VERIFAST PON test. The larger the collected samples number, the better precision, or narrower the 95% CI width, will be obtained for both the sensitivity and specificity of the multiplex test.

As an example, if we would achieve a PON test sensitivity of 90%, with respect to the reference standard lab-grown culture test, by collecting 500 subjects then the 95% CI will be about +/−2.6%. Similarly, a specificity of 70% derived from recruiting 1000 uninfected samples will have a 95% CI of +/−2.8%. This metrics should provide a mean to estimate the number of patient or nonhuman primate (NHP) samples per category that will be needed after delivery of the devices to the sponsor for validation studies.

Example 10: Detection of Nucleic Acids and Biologics

Figure 49:
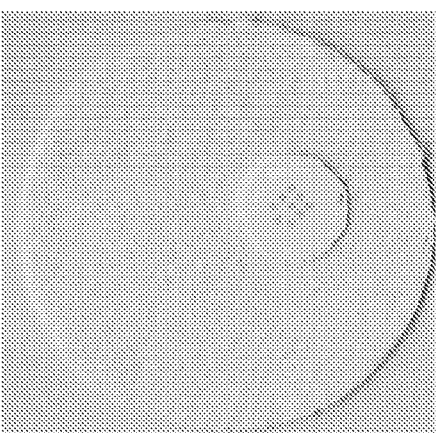
FIG. 49 is similar to FIG. 48, but for detection of LPS antigen associated with Tularemia.
Figure 50:
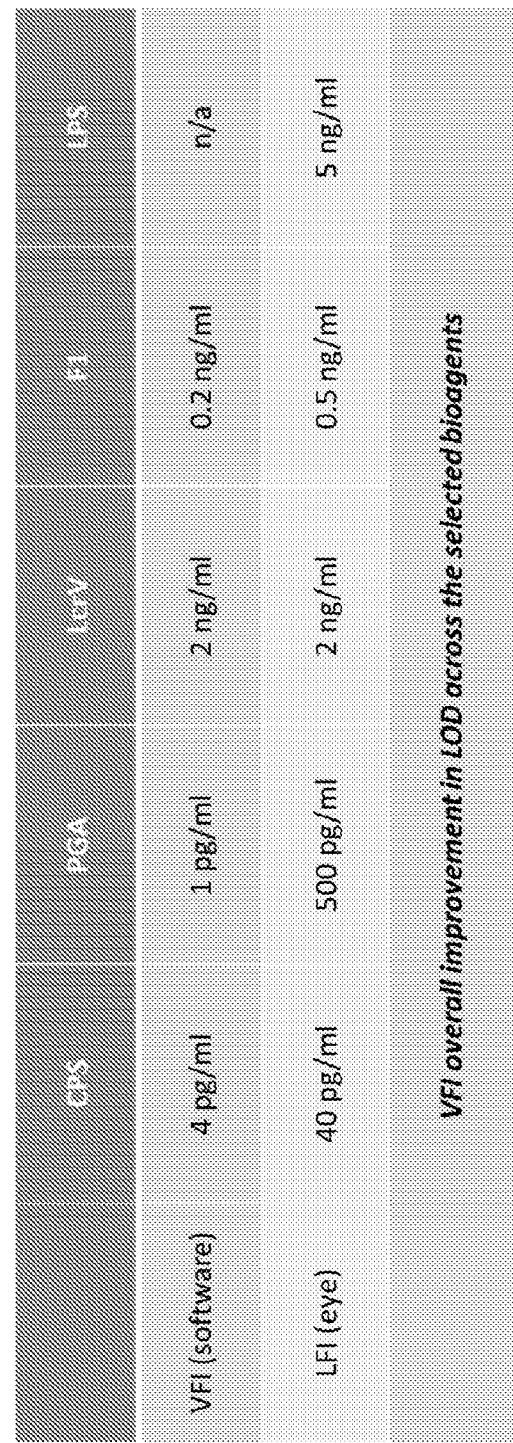
FIG. 50 is a table summary illustrating the instant VFI assays provide an improved or equivalent limit of detection (LOD) across various bioagents, for four Tier I biothreats: Melioidosis—*Burkholderia pseudomallei* (CPS); Anthrax—*Bacillus anthracis* (PGA); Plague—*Yersinia pesis* (F1); Tuleremia—*Francisella tularensis* (LPS).
Figures 51, 52:
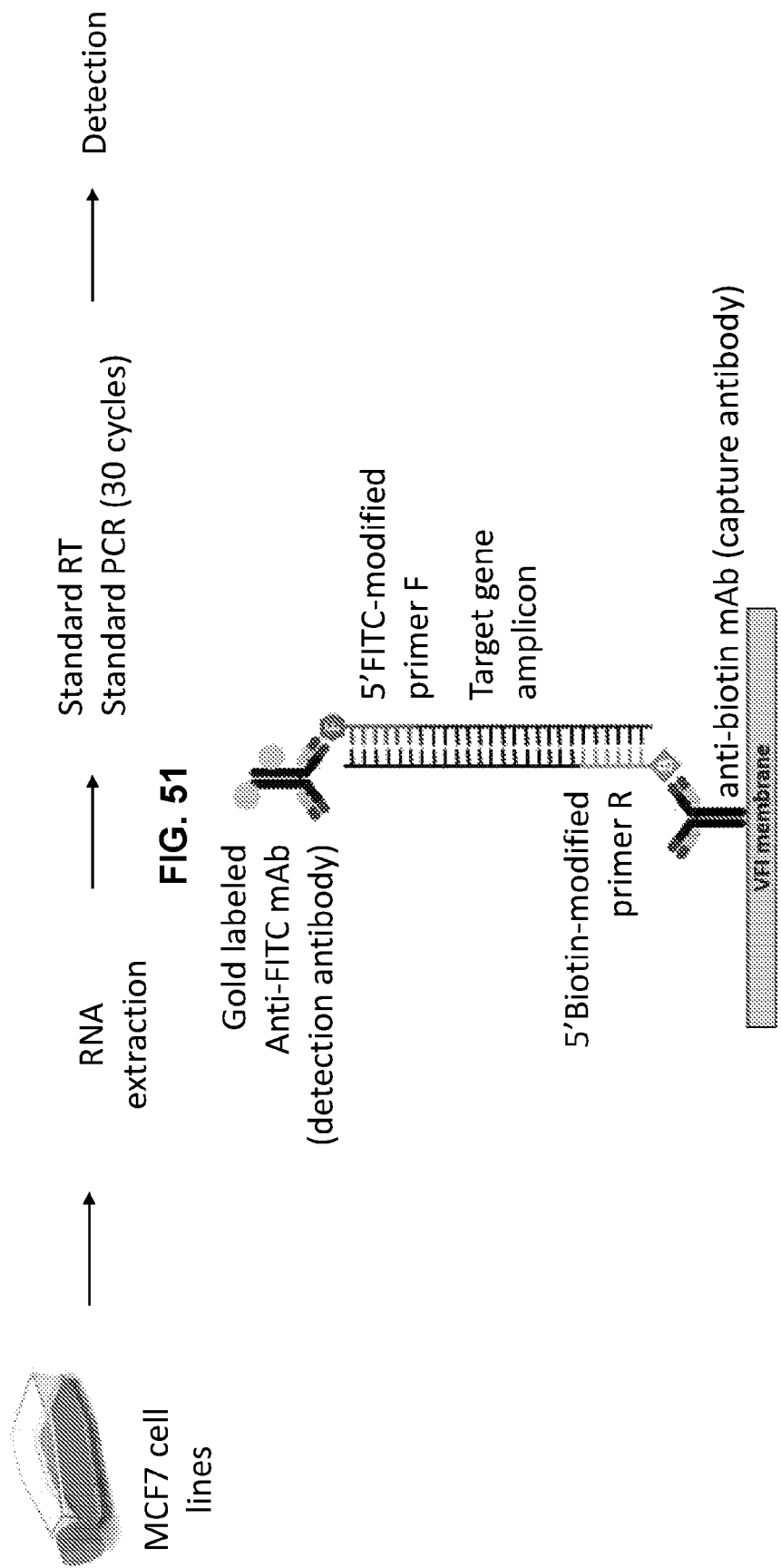
Figures 53, 54:
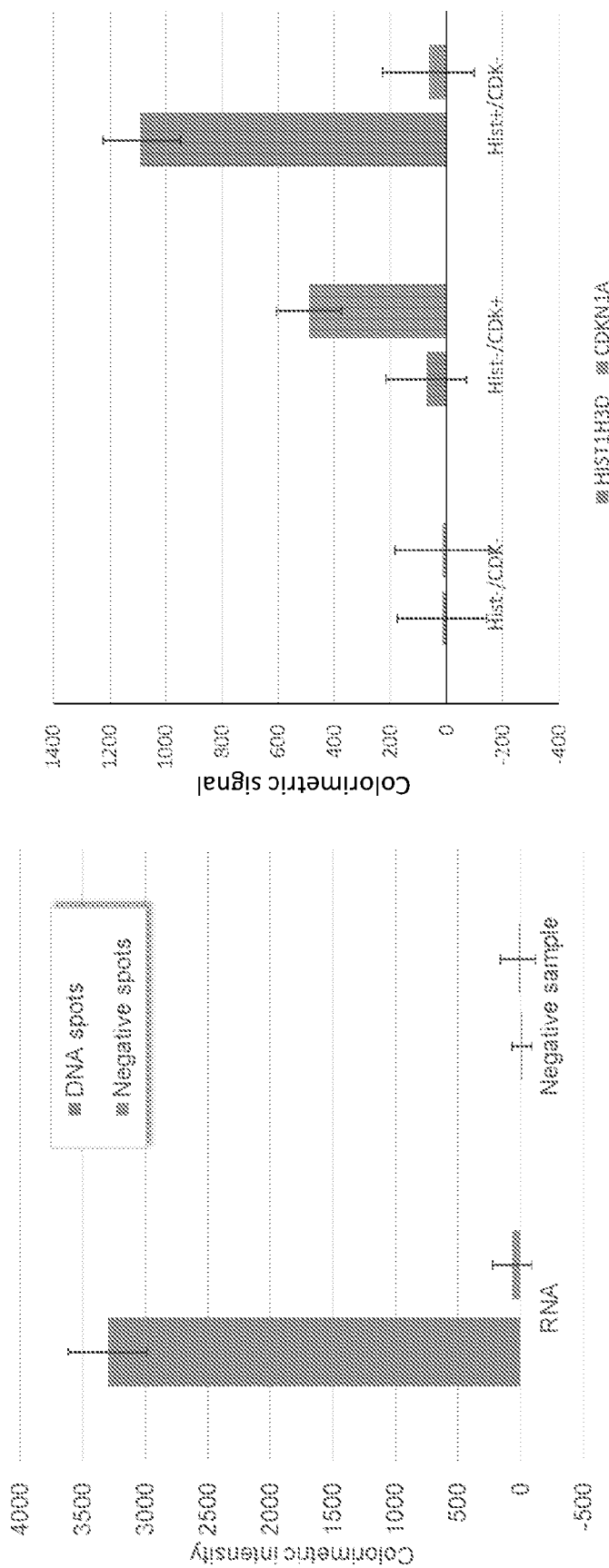
Figure 55:
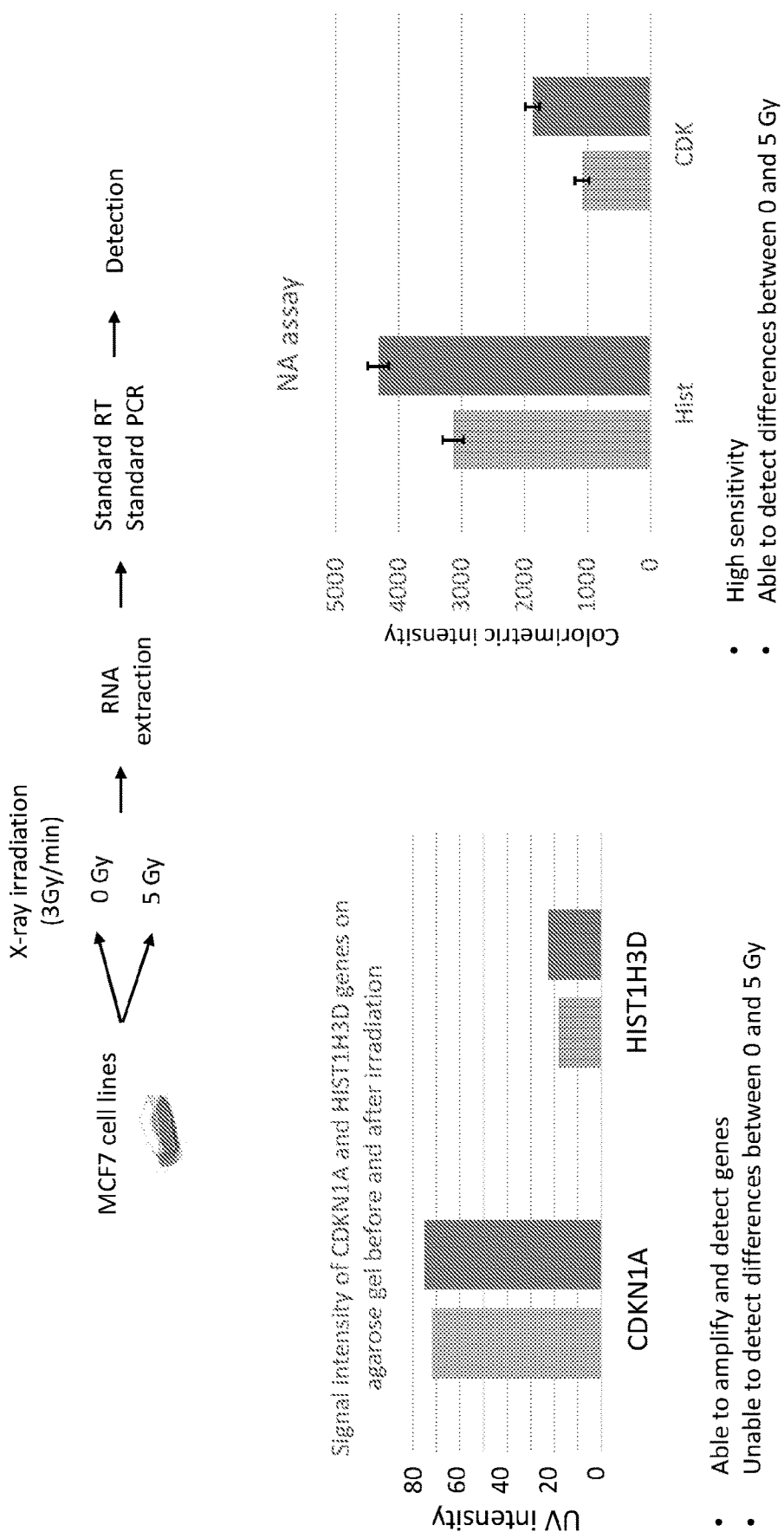

Any of the systems and processes described herein may be used to detect nucleic acids and, more generally, biologics. For example, FIGS. 48-50 demonstrate the usefulness of the vertical flow detection device to detect a range of biologics, including those corresponding to a biothreat. FIGS. 48 and 49 illustrate capture agents connected to the membrane that are antibodies specific to F1 (plague) and LPS. Photographs of the VFI membrane are provided on the right having control spots and detection spots. FIG. 50 summarizes detection results for four Tier I biothreats.

FIG. 51 is a summary of one process for obtaining nucleic acid from cells. RNA can be extracted from a cell line and, as desired, amplification of a target may occur, including by standard RT and standard PCR. Samples may then be introduced to any of the VF systems described herein. Although FIG. 51 illustrates a cell culture, the systems and methods provided herein are compatible with a range of sample starting materials, including but not limited to, a tissue biopsy or biological fluid. FIG. 52 is a schematic illustration of detection of nucleic acid using any of the systems described herein. A capture antibody is connected to the membrane that is specific for a target nucleic acid sequence. A detection antibody can be used to detect the presence of a target nucleic acid sequence bound to the capture antibody.

The systems and methods provided herein have high specificity. For example, FIG. 53 illustrates detection of CDKN1A using vertical flow for a positive sample (CDKN1A amplicon diluted in 1 mL buffer solution) at the nucleotide spot (left most bar) and at the negative spot (right bar). No statistically significant colorimetric signal is detected for the negative sample (1 mL buffer solution).

FIG. 54 summarizes results for detection of CDKN1A and HIST1H3D using a vertical flow device. The system has high specificity for the desired target as illustrated by the negative sample and the samples with only one of the two targets present.

The systems provided herein are useful for detection of cells exposed to radiation. FIG. 55 top panel summarizes an irradiation protocol, where cells are not exposed (0 Gy) or are exposed (5 Gy) to radiation at a dose of 3 Gy/min. RNA is extracted and amplified and the resultant amplicons run on an agarose gel (bottom left panel) or on a vertical flow device. No statistical difference is observed for the agarose gel, whereas as a meaningful difference with radiation is reliably detected by the vertical flow device and method. This indicates that the methods and devices provided herein are highly sensitivity and specificity, making them useful for a range of applications.

For example, the number of genes able to be detected by the membrane can be increased. Further quantification is achieved by using, for example, one or more housekeeping genes to facilitate normalization. One example using four genes is: (1) CDKN1A (reverse: biotin); (2) HIST1H3D (reverse: digoxigenin); (3) DDB2 (reverse: dinitophenyl); (4) housekeeping gene MRPS5 (reverse: Cy3). Similarly, multiplexing for protein detection is compatible by use of different capture antibodies, each specific for relevant protein or portions thereof. Examples of protein detection include detection of *B. pseudomallei* by targeting the capsular polysaccharide (CPS). Other intra-cellular protein biomarkers (e.g. lymphocyte proteins FDXR, BAX, DDB2 and ACTN1) can also be interrogated with a vertical flow device of the present invention. The vertical flow devices and systems are also compatible with a sample that is a blood sample.

Sample preparation, upstream of introduction to the membrane, can be simplified, such as by using isothermal recombinase polymerase amplification (RPA). The systems are compatible with various form factors, including in a fluidic cartridge and can be integrated into various systems. For example, fluidic pumps such as syringe pumps can be replaced with a small, light, self-powered system that is transportable. General requirements include a total volume of about 2 mL to 5 mL and constant flow in the range of 0.2-0.5 mL/min. Examples can include simple and robust systems that is non-powered and capable of applying a constant load, such as a constant force spring and/or ball slide to reduce friction and flow variability.

REFERENCES

AuCoin, D. P., 2012. In vivo microbial antigen discovery: finding the "needle in the haystack." Expert Rev. Mol. Diagn. 12, 219-221. doi:10.1586/erm.12.8

Berger, A. G., Restaino, S. M., White, I. M., 2016. Vertical—flow paper SERS system for therapeutic drug monitoring of flucytosine in serum. Anal. Chim. Acta 4-11. doi: 10.1016/j.aca.2016.10.035

Chen, P, Gates-Hollingsworth, M, Pandit, S, Park, A, Montgomery, D, Aucoin, D, Gu, J, and Zenhausern, F, Paper-based Vertical Flow Immunoassay (VFI) for Detection of Bio-threat Pathogens. Talanta, 191, 1, 81-88 (January 2019), doi.org: 10.1016/j.talanta.2018.08.043

Chinnasamy, T., Segerink, L. I., Nystrand, M., Gantelius, J., Svahn, H. A., 2014. Point-of-care vertical flow allergen microarray assay: Proof of concept. Clin. Chem. 60, 9, 1209-1216. doi:10.1373/clinchem.2014.223230

Clarke, O. J. R., Goodall, B. L., Hui, H. P., Vats, N., Brosseau, C. L., 2017. Development of a SERS-Based Rapid Vertical Flow Assay for Point-of-Care Diagnostics. Anal. Chem. doi:10.1021/acs.analchem.6b04710

Cook J, Caplan Y, LoDico C, Bush D. The characterization of human urine for specimen validity determination in workplace drug testing: A review. J. Anal.Toxicol. 2000; 24:579-88.

Cretich, M., Torrisi, M., Daminelli, S., Gagni, P., Plavisch, L., Chiari, M., 2015. Flow-through, viral co-infection assay for resource-limited settings. Talanta 132, 315-15320. doi:10.1016/j.talanta.2014.09.027

Currie, B. J., Ward, L., Cheng, A. C., 2010. The Epidemiology and Clinical Spectrum of Melioidosis: 540 Cases from the 20 Year Darwin Prospective Study. PLoS Negl. 18, Trop. Dis. 4. doi:10.1371/journal.pntd.0000900 de Jager W, Bourcier K, Rijkers G T, Prakken B J, Seyfert-Margolis V. Prerequisites for cytokine measurements in clinical trials with multiplex immunoassays. BMC Immunol. 2009; 10:52.

Desmet, C., Le Goff, G. C., Br6s, J.-C., Rigal, D., Blum, L. J., Marquette, C. a, 2011. Multiplexed immunoassay for the rapid detection of anti-tumor-associated antigens 21 antibodies. Analyst 136, 2918-2924. doi:10.1039/c1an15121e Dimov I K, Basabe-Desmonts L, Garcia-Cordero J L, Ross B M, Ricco A J, Lee L P. Stand-alone self powered integrated microfluidic blood analysis system (SIMBAS). Lab Chip 2011; 11:845-50.

Eltzov, E., Marks, R. S., 2017. Colorimetric stack pad immunoassay for bacterial identi 23 fi cation. Biosens. Bioelectron. 87, 572-578. doi:10.1016/j.bios.2016.08.044

Galligan C, Nichols J, Kvam E, Spooner P, Gettings R, Zhu L, et al. Mesoscale blood cell sedimentation for processing millilitre sample volumes. Lab Chip 2015; 15:3274-7.

Gao, R., Ko, J., Cha, K., Ho Jeon, J., Rhie, G. E., Choi, J., deMello, A. J., Choo, J., 2015. Fast and sensitive detection of an anthrax biomarker using SERS-based solenoid microfluidic sensor. Biosens. Bioelectron. 72, 230-236. 27, doi:10.1016/j.bios.2015.05.005

Gong M M, MacDonald B D, Trung Vu Nguyen, Kinh Van Nguyen, Sinton D. Field tested milliliterscale blood filtration device for point-of-care applications. Biomicrofluidics 2013; 7:044111

Hárendarčiková, L., Baron, D., Šebestová, A., Rozsypal, J., Petr, J., 2017. True lab-in-a-syringe technology for bioassays. Talanta 174, 285-288. 30 doi:10.1016/j.talanta.2017.06.017

He, Y., Zeng, K., Zhang, S., Gurung, A. S., Baloda, M., Zhang, X., Liu, G., 2012. Visual detection of gene mutations based on isothermal strand-displacement polymerase reaction and lateral flow strip. Biosens. Bioelectron. 31, 310-315. 34, doi:10.1016/j.bios.2011.10.037

Helene, S., Svahn, A., 2014. A lateral flow paper microarray for rapid allergy point of care diagnostics. Analyst. doi: 10.1039/c3an01806g Henderson, K., Stewart, J., 2002. Factors influencing the measurement of oestrone sulphate by dipstick particle capture immunoassay. J. Immunol. Methods 270, 77-3, 84. doi:10.1016/S0022-1759(02)00280-6

Higgins, J. A., Ibrahim, M. S., Knauert, F. K., Ludwig, G. V, Kijek, T. M., Ezzell, J. W., Courtney, B. C., Henchal, E. a, 1999. Sensitive and rapid identification of biological threat agents. Ann. N. Y. Acad. Sci. 894, 130-148. doi: 10.1111/j.1749-76632.1999.tb08056.x Houghton, R. L., Reed, D. E., Hubbard, M. A., Dillon, M. J., Chen, H., Currie, B. J., Mayo, M., Sarovich, D. S., Theobald, V., Limmathurotsakul, D., Wongsuvan, G., Chantratita, N., Peacock, S. J., Hoffmaster, A. R., Duval, B., Brett, P. J., Burtnick, M. N., AuCoin, D. P., 2014. Development of a Prototype Lateral Flow Immunoassay (LFI) for the Rapid Diagnosis of Melioidosis. PLoS Trop. Dis. 8. 13, doi:10.1371/journal.pntd.0002727

Hu, J., Wang, S., Wang, L., Li, F., Pingguan-murphy, B., Jian, T., Xu, F., 2014. Advances in paper-based point-of-care diagnostics. Biosens. Bioelectron. 54, 585-16, 597. doi:10.1016/j.bios.2013.10.075

Indrasekara, A. S. D. S.; Johnson, S. F.; Odion, R. A.; Vo-Dinh, T. Manipulation of the Geometry and Modulation of the Optical Response of Surfactant-Free Gold Nanostars: A Systematic Bottom-Up Synthesis Indrasekara, A. S. D. S.; Meyers, S.; Shubeita, S.; Feldman, L. C.; Gustafsson, T.; Fabris, L. Gold Nanostar Substrates for SERS-Based Chemical Sensing in the Femtomolar Regime Nanoscale 2014, 6, 8891-8899 DOI: 10.1039/C4NR02513J Jansen, H. J., Breeveld, F. J., Stijnis, C., Grobusch, M. P., 2014. Biological warfare, bioterrorism, and biocrime. Clin. Microbiol. Infect. 20, 488-496. 19 doi:10.1111/1469-0691.12699

Jiang H, Weng X, Chon C H, Wu X, Li D. A microfluidic chip for blood plasma separation using electro-osmotic flow control. J Micromech Microengineering 2011; 21:085019.

Juncker, D., Bergeron, S., Laforte, V., Li, H., 2014. Cross-reactivity in antibody microarrays and multiplexed sandwich assays: Shedding light on the dark side of multiplexing. Curr. Opin. Chem. Biol. 18, 29-37. doi:10.1016/j.cbpa.2013.11.012

Kim B, Oh S, You D, Choi S. Microfluidic Pipette Tip for High-Purity and High-Throughput Blood Plasma Separation from Whole Blood. Anal. Chem. 2017; 89:1439-44.

Kuo J, Zhan Y. Microfluidic chip for rapid and automatic extraction of plasma from whole human blood. Microsyst. Technol. 2015; 21:255-61.

Lacombe J, Sima C, Amundson S A, Zenhausern F. Candidate gene bio dosimetry markers of exposure to external ionizing radiation in human blood: A systematic review. PLoS One. 2018 Jun. 7; 13(6):e0198851

Lafleur, L., Stevens, D., Mckenzie, K., Ramachandran, S., Spicar-Mihalic, P., Singhal, M., Arjyal, A., Osborn, J., Kauffman, P., Yager, P., Lutz, B., 2012. Progress toward multiplexed sample-to-result detection in low resource settings using microfluidic immunoassay cards. Lab Chip 12, 1119-1127. 27, doi:10.1039/c21c20751f Lakoff, A., 2008. The Generic Threat, or how we became unprepared. Cult. Anthropol. 29, 23, 399-428. doi: 10.1525/can.2008.23.3.399. C Lenshof A, Ahmad-Tajudin A, Jaras K, Sward-Nilsson A, Aberg L, Marko-Varga G, et al. Acoustic Whole Blood Plasmapheresis Chip for Prostate Specific Antigen Microarray Diagnostics. Anal. Chem. 2009; 81:6030-7.

Li, C. Z., Vandenberg, K., Prabhulkar, S., Zhu, X., Schneper, L., Methee, K., Rosser, C. J., Almeide, E., 2011. Paper based point-of-care testing disc for multiplex whole cell bacteria analysis. Biosens. Bioelectron. 26, 4342-4348. 33 doi:10.1016/j.bios.2011.04.035

Li, Z., Wang, Y., Wang, J., Tang, Z., Pounds, J. G., Lin, Y., 2010. Rapid and Sensitive Detection of Protein Biomarker Using a Portable Fluorescence Biosensor Based on Quantum Dots and a Lateral Flow Test Strip. Anal. Chem. 82, 7008-7014.

Limmathurotsakul, D., Golding, N., Dance, D. A. B., Messina, J. P., Pigott, D. M., Moyes, C. L., Rolim, D. B., Bertherat, E., Day, N. P. J., Peacock, S. J., Hay, S. I., 2016. Predicted global distribution of *Burkholderia pseudomallei* and burden of melioidosis. Nat. Microbiol. 1, 6-10. doi:10.1038/nmicrobiol.2015.8

Limmathurotsakul, D., Jamsen, K., Arayawichanont, A., Simpson, J. A., White, L. J., Lee, S. J., Wuthiekanun, V., Chantratita, N., Cheng, A., Day, N. P. J., Verzilli, C., Peacock, S. J., 2010a. Defining the True Sensitivity of Culture for the Diagnosis of Melioidosis Using Bayesian Latent Class Models. PLoS One 5. 6 doi:10.1371/journal.pone.0012485

Limmathurotsakul, D., Wongratanacheewin, S., Teerawattanasook, N., Wongsuvan, G., 2010b. Increasing Incidence of Human Melioidosis in Northeast Thailand. Am. J. 9 Trop. Med. Hyg. 82, 1113-1117. doi:10.4269/ajtmh.2010.10-0038

Liu C, Liao S, Song J, Mauk M G, Li X, Wu G, et al. A high-efficiency superhydrophobic plasma separator. Lab Chip 2016; 16:553-60.

Liu, G., Mao, X., Phillips, J. A., Xu, H., Tan, W., Zeng, L., 2009. Aptamer—Nanoparticle Strip Biosensor for Sensitive Detection of Cancer Cells. Anal. Chem. 12 81, 10013-10018.

Liu, Y.; Ashton, J. R.; Moding, E. J.; Yuan, H.; Register, J. K.; Fales, A. M.; Choi, J.; Whitley, M. J.; Zhao, X.; Qi, Y.; Ma, Y.; Vaidyanathan, G.; Zalutsky, M. R.; Kirsch, D. G.; Badea, C. T.; Vo-Dinh, T. A Plasmonic Gold Nanostar Theranostic Probe for In Vivo Tumor Imaging and Photothermal Therapy Theranostics 2015, 5,946-960 DOI: 10.7150/thno.11974

Lu, Y., Shi, W., Qin, J., Lin, B., 2010. Fabrication and characterization of paper-based microfluidics prepared in nitrocellulose membrane by Wax printing. Anal. Chem. 15, 82, 329-335. doi:10.1021/ac9020193

Lu et al. Sci Rep. 2014

Lucas, J, Dressman, H, Suchindran, S, Nakamura, M, Chao, N, Himburg, H, Minor, K, Phillips, G, Ross, J, Abedi, M, Terbrueggen, R, Chute, J, PlosOne, 9, 9 (September 2014) doi.org/10.1371/journal.pone.0107897

L W, C., LJ, C., JA, P., E M, E., Jr, 1997. Biological warfare: A historical perspective. 17 JAMA 278, 412-417.

Mu, X., Zhang, L., Chang, S., Cui, W., Zheng, Z., 2014. Multiplex microfluidic paper-based immunoassay for the diagnosis of hepatitis C virus infection. Anal. Chem. 2086, 5338-5344. doi:10.1021/ac500247f Nuti, D. E., Crump, R. B., Handayani, F. D., Chantratita, N., Peacock, S. J., Bowen, R., Felgner, P. L., Davies, D. H., Wu, T., Lyons, C. R., Brett, P. J., Burtnick, M. N., Kozel, T. R., AuCoina, D. P., 2011. Identification of circulating bacterial antigens by in vivo microbial antigen discovery. MBio 2, 1-8. doi:10.1128/mBio.00136-11

Oh, Y. K., Joung, H.-A., Kim, S., Kim, M.-G., 2013. Vertical flow immunoassay (VFA) biosensor for a rapid one-step immunoassay. Lab Chip 13, 768-72. 27 doi:10.1039/c21c41016h Park, J., Park, J. K., 2017. Pressed region integrated 3D paper-based microfluidic device that enables vertical flow multistep assays for the detection of C-reactive protein based on programmed reagent loading. Sensors Actuators, B Chem. 246, 1049-31 1055. doi:10.1016/j.snb.2017.02.150

Parolo, C., Arben Merkogi, 2013. Paper-based nanobiosensors for diagnostics. Chem 33 Soc Rev 450-457. doi: 10.1039/c2cs35255a Pauli, G. E. N., Escosura-muAiz, A. De, Parolo, C., Bechtold, I. H., Merkogi, A., 2015. Lab-in-a-syringe using gold nanoparticles for rapid immunosensing of protein 36 biomarkers. Lab Chip 15, 399-405. doi:10.1039/C4LC01123F Perry, M. B., Lean, M., Schollaardt, T., Bryan, L. E., Ho, M., 1995. Structural Characterization of the Lipopolysaccharide O Antigens of *Burkholderia pseudomallei*. Infect. Immun. 63, 3348-3352.

Posthuma-Trumpie, G. A., Korf, J., Van Amerongen, A., 2009. Lateral flow (immuno)assay: Its strengths, weaknesses, opportunities and threats. A literature 4 survey. Anal. Bioanal. Chem. 393, 569-582. doi:10.1007/s00216-008-2287-2

Ramachandran, S., Singhal, M., McKenzie, K., Osborn, J., Arjyal, A., Dongol, S., Baker, S., Basnyat, B., Farrar, J., Dolecek, C., Domingo, G., Yager, P., Lutz, B., 2013. A Rapid, Multiplexed, High-Throughput Flow-Through Membrane Immunoassay: A Convenient Alternative to ELISA. Diagnostics 3, 244-260. 9 doi:10.3390/diagnostics3020244

Reuterswärd, P., Gantelius, J., Andersson Svahn, H., 2015. An 8 minute colorimetric paper-based reverse phase vertical flow serum microarray for screening of hyper 12 IgE syndrome. Analyst 140, 7327-7334. doi:10.1039/C5AN01013F Rivas, L., De, E. A., Serrano, L., Altet, L., Francino, O., Sanchez, A., Merkoci, A., 2015. Triple lines gold nanoparticle-based lateral flow assay for enhanced and simultaneous detection of *Leishmania* DNA and endogenous control. Nano Res. 8, 16 3704-3714. doi:10.1007/s12274-015-0870-3

Robertson, G., Sorenson, A., Govan, B., Ketheesan, N., Houghton, R., Chen, H., Aucoin, D., Dillon, M., Norton, R., 2015. Rapid diagnostics for melioidosis: A comparative study of a novel lateral flow antigen detection assay. J. Med. Microbiol. 64, 845-848. doi:10.1099/jmm.0.000098

Rosenberg-Hasson Y, Hansmann L, Liedtke M, Herschmann I, Maecker H T. Effects of serum and plasma matrices on multiplex immunoassays. Immunol. Res. 2014; 58:224-33.

Safenkova, I. V, Pankratova, G. K., Zaitsev, I. A., Varitsev, Y. A., Vengerov, Y. Y., Zherdev, A. V, Dzantiev, B. B., 2016. Multiarray on a test strip (MATS): rapid multiplex immunodetection of priority potato pathogens. Anal. Bioanal. Chem. 24 6009-6017. doi:10.1007/s00216-016-9463-6

Schlappi, T. S., McCalla, S. E., Schoepp, N. G., Ismagilov, R. F., 2016. Flow-through Capture and in Situ Amplification Can Enable Rapid Detection of a Few Single Molecules of Nucleic Acids from Several Milliliters of Solution. Anal. Chem. 88, 7647-7653. doi:10.1021/acs.analchem.6b01485

Sirisinha, S., Anuntagool, N., Dharakul, T., 2000. Recent developments in laboratory diagnosis of melioidosis. Acta Trop. 74, 235-245.

Squires, T. M., Messinger, R. J., Manalis, S. R., 2008. Making it stick: convection, reaction and diffusion in surface-based biosensors. Nat. Biotechnol. 26, 417-426. doi:10.1038/nbt1388

Sviridov D, Hortin G L. Urine albumin measurement: Effects of urine matrix constituents. Clinica Chimica Acta 2009; 404:140-3.

Tate J, Ward G. Interferences in immunoassay. The Clinical biochemist. Reviews 2004; 25:105-20.

Wang, H.-N.; Crawford, B. M.; Fales, A. M.; Bowie, M. L.; Seewaldt, V. L.; Vo-Dinh, T. Multiplexed Detection of MicroRNA Biomarkers Using SERS-Based Inverse Molecular Sentinel (iMS) Nanoprobes J. Phys. Chem. C 2016, 120, 21047-21055 DOI: 10.1021/acs.jpcc.6b03299

Warren, A. D., Kwong, G. A., Wood, D. K., Lin, K. Y., Bhatia, S. N., 2014. Point-of-care diagnostics for non-communicable diseases using synthetic urinary biomarkers and paper microfluidics. Proc. Natl. Acad. Sci. 111. doi:10.1073/pnas.1314651111

Wiersinga, W. J., Currie, B. J., Peacock, S. J., 2012. Melioidosis. N. Engl. J. Med. 1035-1044. doi:10.1056/NEJMra1204699

Wood M W, Nordone S K, Vaden S L, Breitschwerdt E B. Assessment of urine solute and matrix effects on the performance of an enzyme-linked immunosorbent assay for measurement of interleukin-6 in dog urine. J. Vet. Diagn. Invest. 2011; 23:316-20.

Yetisen, A. K., Akram, M. S., Lowe, C. R., 2013. Paper-based microfluidic point-of-care diagnostic devices. Lab Chip 13, 2210-51. doi:10.1039/c3lc50169h Yuan, H.; Fales, A. M.; Vo-Dinh, T. TAT Peptide-Functionalized Gold Nanostars: Enhanced Intracellular Delivery and Efficient NIR Photothermal Therapy Using Ultralow Irradiance J. Am. Chem. Soc. 2012, 134, 11358-11361 DOI: 10.1021/ja304180y Yuan, H.; Khoury, C. G.; Hwang, H.; Wilson, C. M.; Grant, G. A.; Vo-Dinh, T. Gold Nanostars: Surfactant-Free Synthesis, 3D Modelling, and Two-Photon Photoluminescence Imaging Nanotechnology 2012, 23075102 DOI: 10.1088/0957-4484/23/7/075102

Zimmermann, M., Delamarche, E., Wolf, M., Hunziker, P., 2005. Modeling and optimization of high-sensitivity, low-volume microfluidic-based surface immunoassays. Biomed. Microdevices 7, 99-110. doi:10.1007/s10544-005-1587-y

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, a number range, a pore size range, a porosity range, a thickness range, LOD range, a temperature range, a time range, a flow-rate range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A vertical flow detection device comprising:
    a membrane having a first surface and a second surface, wherein the first surface opposibly faces the second surface and the first and second surfaces are separated by a membrane thickness;
    a plurality of porous structures extending between the first and second surfaces to form fluid conduits from a first fluid chamber formed by the first surface and a second fluid chamber formed by the second fluid surface;
    a capture agent immobilized on the membrane first surface and/or internally in the membrane between the first and second membrane surfaces;
    a silicon rigid porous membrane support positioned to mechanically support the membrane and to provide a relatively uniform flow across the membrane first surface exposed to said first fluid chamber during use;
    a gasket or fluid impermeable material positioned around an outer edge of the membrane;
    a holder to provide a tight-fit configuration with the membrane and gasket or fluid impermeable material to prevent fluid leakage around the membrane; and
    a flow device configured to force a fluid sample flow in a direction from the first fluid chamber to the second fluid chamber.

2. The vertical flow detection device of claim 1, further comprising a gasket positioned around an outer edge of the rigid support and between the rigid support and the holder.

3. The vertical flow detection device of claim 1, further comprising a detector to detect a target analyte in a fluid sample bound to the capture agent, the detector optionally comprising a scanner or imager configured to scan or image the membrane.

4. The vertical flow detection device of claim 1, wherein the holder comprises a fitting configured to mount to an imaging system for imaging the membrane without disassembly of the device to provide a complete sample to detection system in a point-of-care setting, wherein the imaging system is optionally selected from the group consisting of a portable imager, a scanner, and a smartphone.

5. The vertical flow detection device of claim 1, comprising a plurality of distinct capture agents provided as a spatially discrete array for multiplexed detection of two or more different target analytes.

6. The vertical flow detection device of claim 1 configured to accommodate bi-directional flow, the device further comprising:
    a top and a bottom diffuser membrane with the membrane provided between the top and bottom diffuser membrane;
    an additional rigid porous membrane to provide a first rigid porous membrane support and a second rigid porous membrane support, wherein the first rigid porous membrane is adjacent to an exposed surface of the top diffuser membrane and the second rigid porous membrane support is adjacent to an exposed surface of the second diffuser membrane;
    a first gasket integrated with the first rigid porous membrane support and a second gasket integrated with the second rigid porous membrane support to provide additional support and sealing, including two gaskets for each surface of the rigid supports to provide sealing with the membranes and holder to make sure all fluid passes the center area of the membranes, and, optionally, wherein the gaskets are integrated with the rigid supports;
    wherein the top and bottom diffuser membranes provide a relatively uniform flow through the membrane, including the membrane first surface having capture agent immobilized thereto.

7. The vertical flow detection device of claim 6, further comprising two o-rings, with a first o-ring supported by a top surface of the first rigid porous membrane support and the second o-ring supported by a bottom surface of the second rigid porous membrane support to ensure good sealing between the fluid chambers and the membrane support.

8. The vertical flow detection device of claim 1, wherein the capture agent comprises an antibody, the target analyte specifically binds to the antibody, and a detectable label is connected directly or indirectly to the target analyte.

9. The vertical flow detection device of claim 1, wherein the membrane comprises one or more porous solid state materials selected from the group consisting of paper, nitrocellulose, cellulose, PVDF, polycarbonate, ceramic, glass, and anodized aluminum.

10. The vertical flow detection device of claim 1, wherein the average pore size of the membrane is less than 10 µm, less than 1 µm, less than 0.5 µm, or less than or equal to 0.1 µm and has a porosity of between 10% and 95%, and optionally a porous structure that is interconnected or fibrous.

11. The vertical flow detection device of claim 1, wherein the membrane has a thickness that is greater than or equal to 1 µm and less than or equal to 1000 µm.

12. The vertical flow detection device of claim 1, wherein the porous membrane support has a pore size that is greater than or equal to 1 µm and less than or equal to 1000 µm and spatially arranged to provide a substantially uniform flow rate profile across the membrane.

13. The vertical flow detection device of claim 1, having a plurality of capture agent spots and a capture agent spot size of between 1 μm and 5 mm and a fluid sample flow is uniformly directed to said capture agent spots.

14. The vertical flow detection device of claim 1, having an exposed to flow membrane surface area to receive a fluid flow, further comprising means for adjusting an exposed to flow membrane surface area, wherein the exposed to flow membrane surface area is selected based on a desired flow-rate and sample volume, with surface area increasing for increasing sample volume, wherein the means for adjusting is selected from the group consisting of: an adjustable basket, an impermeable laver covering a portion of the membrane, and a mask layer Positioned over the membrane.

15. The vertical flow detection device of claim 1, wherein the flow device is selected from the group consisting of a syringe, a pump, and a passive capillary driven system.

16. The vertical flow detection device of claim 1, further comprising a positive control spot on the membrane.

17. A method of detecting an analyte in a fluid sample, the method comprising the steps of:
providing the vertical flow detection device of claim 1;
forcing a flow of fluid sample from the first fluid chamber to the second fluid chamber through the plurality of pores in the membrane;
binding a target analyte present in the fluid sample to a capture agent; and
detecting the target analyte bound to the capture agent with the detector.

18. The method of claim 17 wherein the vertical flow detection device accommodates bi-directional flow so that sample can be repeatedly directed in opposite flow directions to improve sample detection and sample usage.

19. The method of claim 17, wherein the forcing step comprises pumping of the fluid sample by generating a higher pressure in the first fluid chamber relative to a lower pressure in the second fluid chamber.

20. The method of claim 17, wherein the forcing step comprises pumping of the fluid sample by generating a higher pressure in the first fluid chamber relative to a lower pressure in the second fluid chamber and subsequently generating a higher pressure in the second fluid chamber relative to a lower pressure in the first fluid chamber, thereby providing controlled bi-directional flow.

21. The vertical flow detection device of claim 1, wherein the silicon rigid porous membrane support is selected from the group consisting of a silicon grid and silicon mesh.

22. The method of claim 17, wherein the silicon rigid porous membrane support is selected from the group consisting of a silicon grid and silicon mesh.

* * * * *